United States Patent
Delecluse et al.

(10) Patent No.: US 10,961,280 B2
(45) Date of Patent: Mar. 30, 2021

(54) B-CELL RECEPTOR COMPLEX BINDING PROTEINS CONTAINING T-CELL EPITOPES

(71) Applicant: Deutsches Krebsforschungszentrum, Heidelberg (DE)

(72) Inventors: Henri-Jacques Delecluse, Heidelberg (DE); Regina Feederle, Munich (DE); Emmalene Bartlett, Eppelheim (DE)

(73) Assignee: Deutsches Krebsforschungszentrum, Heidelberg (DE)

(*) Notice: Subject to any disclaimer, the term of this patent is extended or adjusted under 35 U.S.C. 154(b) by 0 days.

(21) Appl. No.: 16/030,663

(22) Filed: Jul. 9, 2018

(65) Prior Publication Data
US 2018/0312547 A1    Nov. 1, 2018

Related U.S. Application Data

(62) Division of application No. 14/386,275, filed as application No. PCT/EP2013/055690 on Mar. 19, 2013, now Pat. No. 10,040,827.

(30) Foreign Application Priority Data

Mar. 19, 2012 (EP) .................... 12160165

(51) Int. Cl.
| | |
|---|---|
| *A61K 39/12* | (2006.01) |
| *A61K 39/245* | (2006.01) |
| *C07K 14/005* | (2006.01) |
| *C07K 16/28* | (2006.01) |
| *C12N 7/00* | (2006.01) |
| *A61K 39/00* | (2006.01) |

(52) U.S. Cl.
CPC ............ *C07K 14/005* (2013.01); *A61K 39/12* (2013.01); *A61K 39/245* (2013.01); *C07K 16/2803* (2013.01); *C07K 16/2896* (2013.01); *C12N 7/00* (2013.01); *A61K 2039/55516* (2013.01); *A61K 2039/572* (2013.01); *A61K 2039/585* (2013.01); *A61K 2039/6056* (2013.01); *C07K 2317/569* (2013.01); *C07K 2319/33* (2013.01); *C12N 2710/16222* (2013.01); *C12N 2710/16234* (2013.01)

(58) Field of Classification Search
None
See application file for complete search history.

(56) References Cited

FOREIGN PATENT DOCUMENTS

| | | |
|---|---|---|
| WO | WO 90/04176 | 4/1990 |
| WO | WO 96/17625 | 6/1996 |
| WO | WO 97/23237 | 7/1997 |
| WO | WO 99/02550 | 1/1999 |
| WO | WO 2001/12215 A2 | 2/2001 |
| WO | WO 2005/030931 A2 | 5/2005 |
| WO | WO 2007/097820 A2 | 8/2007 |
| WO | WO 2007/103469 A2 | 9/2007 |
| WO | WO 2008/098145 A1 * | 8/2008 |

OTHER PUBLICATIONS

Ma et al. Targeting of Antigens to B Lymphocytes via CD19 as a Means for Tumor Vaccine Development. Journal of Immunology, 2013, 190: 5588-5599.*
Ho et al. Isolation of anti-CD22 Fv with high affinity by Fv display on human cells. PNAS Jun. 20, 2006 103 (25) 9637-9642.*
Onda et al. An immunotoxin with greatly reduced immunogenicity by identification and removal of B cell epitopes. P.N.A.S. 2008, 105:11311-11316.*
Vallera et al. A Bispecific Recombinant Immunotoxin, DT2219,Targeting Human CD19 andCD22 Receptors inaMouseXenograftModel of B-Cell Leukemia/Lymphoma. Clin Cancer Res 2005;11(10): 3879-3888.*
Diethelm-Okita et al. Universal Epitopes for Human CD4+ Cells on Tetanus and Diphtheria Toxins. The Journal of Infectious Diseases 2000;181:1001-9.*
Matheson et al. Diphtheria-Tetanus-Acellular Pertussis Vaccine Adsorbed (Triacelluvax™; DTaP3-CB) . Paediatr Drugs Mar.-Apr. 2000; 2 (2): 139-159.*
Kaech et al. (2002), "Effector and Memory T-Cell Differentiation: Implications for Vaccine Development," Nature Reviews Immunology 2(4):251-62.

(Continued)

*Primary Examiner* — Nianxiang Zou
(74) *Attorney, Agent, or Firm* — Foley & Lardner LLP

(57) ABSTRACT

The present invention relates to a polypeptide comprising a) a binding peptide binding to at least one protein selected from the group consisting of CD22, CD19, CD20, and CD21, and b) an immunogenic peptide comprising at least one T-cell epitope for use in vaccination of a subject against B-cell hyperproliferation or for use in the modulation of the immune response in a subject. The present invention further relates to a polynucleotide and a vector encoding said polypeptide and a host cell comprising the same. It also relates to a method for the stimulation of antigen-specific T-cells, comprising a) contacting antigen presenting cells (APC) with a polypeptide, the polynucleotide, or the vector of the invention, b) contacting said APC with T-cells, and c) thereby stimulating antigen-specific T-cells specific for said at least one T-cell epitope; to a method for immunizing a subject against B-cell hyperproliferation, to a method for immunizing a subject against an infectious agent, and to a method for inducing tolerance in a subject.

18 Claims, 5 Drawing Sheets

Figure 1:
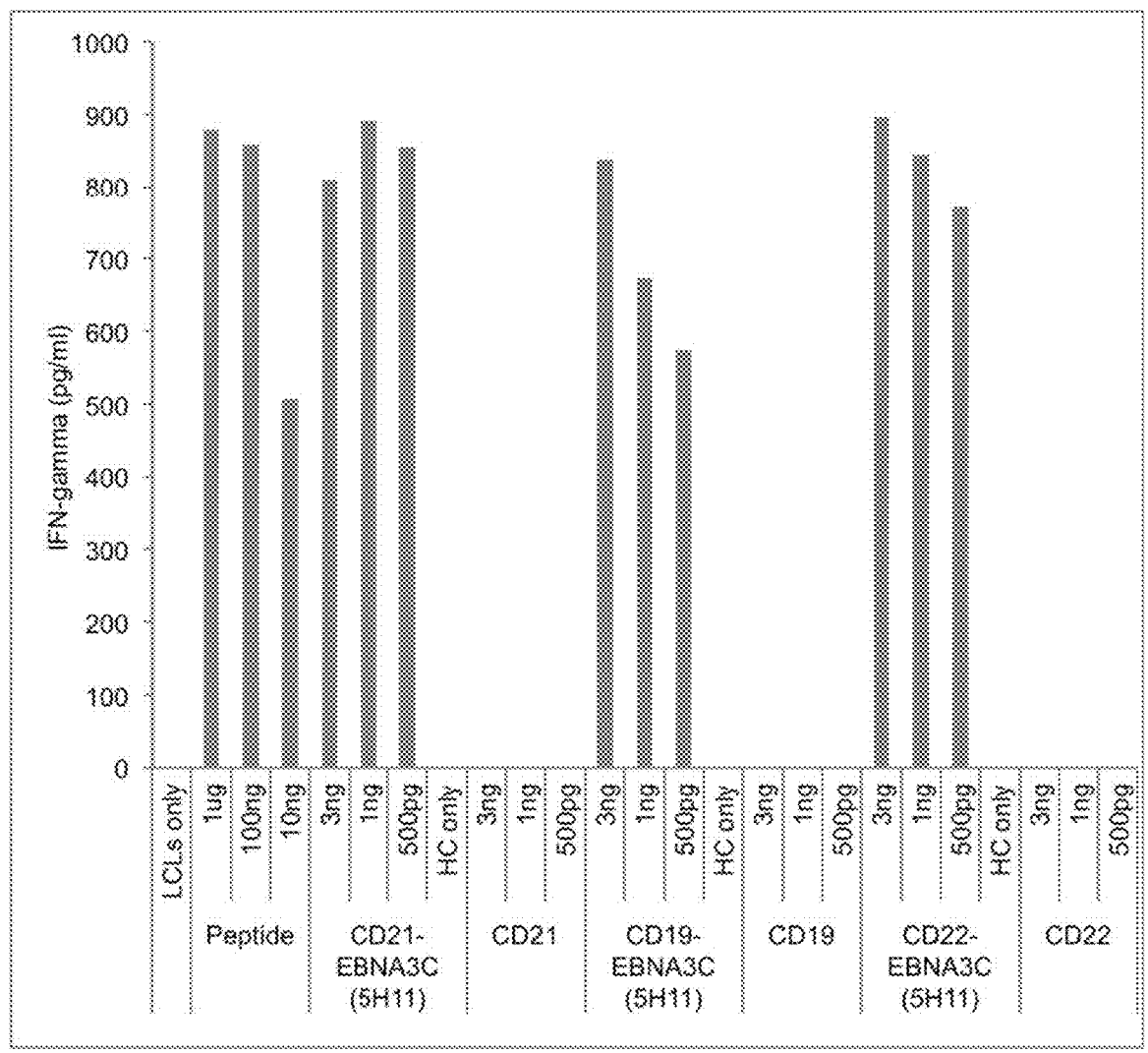

Specification includes a Sequence Listing.

(56) References Cited

OTHER PUBLICATIONS

Pulendran et al., "Translating Innate Immunity into Immunological Memory: Implicants for Vaccine Development," (2006), Cell 124(4):849-63).
Fearon et al., Regulation of B Lymphocyte Responses to Foreign and Self-Antigens by the CD19/CD21 Complex, (2000), Ann. Rev. Immunol., vol. 18, pp. 393-422.
Nielsen et al., "Improved Prediction of MHC class I and class II epitopes using a novel Gibbs sampling approach," (2004), Bioinformatics, 20 (9), 1388-1397.
Bordner, "Towards Universal Structure-Based Prediction of Class II MHC Epitopes for Diverse Allotypes," (2010), PLoS ONE 5(12): e14383, 12 pages.
Bernardeau et al., "A simple competitive assay to determine peptide affinity for HLA class II molecules: A useful tool for epitope prediction," (2011), J. Immunol. Methods, 371(1-2):97-105.
Busse et al. "Epstein-Barr Viruses that Express a CD21 Antibody Provide Evidence that gp350's Functions Extend beyond B-Cell Surface Binding," (2010), J. Virology 84(2):1139-1147.
Long et al. "Immune defense against EBV and EBV-associated disease," (2011), Curr Opin Immunol 23(2):258-64.
Adhikary et al. "Control of Epstein-Barr virus infection in vitro by T helper cells specific for virion glycoproteins," (2006), J. Exp. Med. 203(4):995-1006.
Gurer et al., "Targeting the nuclear antigen 1 of Epstein-Barr virus to the human endocytic receptor DEC-205 stimulates protective T-cell responses," (2008), Blood 112 (4) : 1231-9.
Reineke, et al. "Identification of Distinct Antibody Epitopes and Mimotopes from a Peptide Array of 5520 Randomly Generated Sequences," (2002) J. Immunol. Methods. 267(1):37-51.
Milosevic, et al., "Identification of Major Histocompatibility Complex Class II-Restricted Antigens and Epitopes of the Epstein-Barr Virus by a Novel Bacterial Expression Cloning Approach," (2006), J. Virol. 80(21):10357-10364.
Pedroza-Roldan, et al., "Variable epitope library-based vaccines: Shooting moving targets," (2009), 47:270-282.
Moir et al., "B Cells in HIV Infection and Disease," (2009), Nat Rev Immunol., vol. 9, pp. 235-245.
Sugalski, et al., "Peripheral Blood B Cell Subset Skewing is Associated with Altered Cell Cycling and Intrinsic Resistance to Apoptosis and Reflects a State of Immune Activation in Chronic Hepatitis C Virus Infection," (2010), J. Immunology, vol. 185, pp. 3019-3027.
Ivanovska, et al: "Immunization with a DNA chimeric molecule encoding a hemagglutinin peptide and a scFv CD21-specific antibody fragment induces long-lasting IgM and CTL responses to influenza virus", Vaccine, vol. 24, No. 11, (2006), pp. 1830-1837.
Molnar et al: "Targeting with SCFV: Immune Modulation by Complement Receptor Specific Constructs", Journal of Molecular Recognition, vol. 16, No. 5, (2003), pp. 318-323.
Zhang et al, "Fusion to chicken C3d enhances the immunogenicity of the M2 protein of avian influenza virus", Virology Journal, Biomed Central, vol. 7, No. 1, (2010), 11 pages.

Whipple et al, "Low doses of antigen coupled to anti-CR2 mAbs induce rapid and enduring IgG immune responses in mice and in cynomolgus monkeys", Molecular Immunology, Pergamon, vol. 44, No. 4, (2007), pp. 377-388.
Alexander Riedel: "Untersuchungen zur endogenen MHC-Klasse-II-restringierten Präsentation nukleärer Antigene", (2007), pp. 1-116 [English Abstract at p. VI].
Leen, et al., "Differential Immunogenicity of Epstein-Barr Virus Latent-Cycle Proteins for Human CD4+ T-helper 1 Responses," Journal of Virology, vol. 75, No. 18, pp. 8649-8659 (Sep. 2001).
Thesis of Alexander Riedel, 116 pages (2007)—English Abstract at p. 9.
Eberl et al., "An anti-CD19 antibody coupled to a tetanus toxin peptide induces efficient Fas ligand (FasL)-mediated cytotoxicity of a transformed human B cell line by specific CD4+ T cells," Clin. Exp. Immunol., vol. 114, pp. 173-178 (Jul. 1998).
Busse et al., Epstein-Barr Viruses that Express a CD21 Antibody Provide Evidence that gp350's Functions Extend beyond B-Cell Surface Binding, J. of Virolology, vol. 84, pp. 1139-1147 (2010).
Khanna et al., "EBV Structural Antigens, gp350 and gp85, as Targets for Ex Vivo Virus-Spcific CTL During Acute Infectious Mononucleosis: Potential Use of gp350/gp85 CTL Epitopes for Vaccine," Design J. Immunol., vol. 162, pp. 3063-3069 (1999).
GenBank: M10593.1 Epstein Barr Virus Major Outer Envelope Glycoprotein Genes gp350 and gp220, complete cds. Aug. 2, 1993.
Yong et al., "Molecular Basis of the Interaction between Complement Receptor Type 2 (CR2CD21) and Epstein-Barr Virus Glycoprotein gp350," J. Virol., vol. 82, pp. 11217-11227 (2008).
Ivanovska et al., "Immunization with a DNA chimeric molecule encoding a hemagglutinin peptide and a scFv CD21-specific antibody fragment induces long-lasting IgM and CTL responses to influenza virus," Vaccine, vol. 24, No. 11 pp. 830-837 (Mar. 2006).
Lalonde et al., "Rescue of the Immunotherapeutic potential of a novel T cell epitope in the Epstein-Barr virus latent membrane protein 2", Virology, vol. 361, No. 2, pp. 253-262 (Jan. 2007).
Gahn et al., "Adenoviral gene ransfer into dendritic cells efficiently amplifies the immune response to LMP2A antigen: a potential treatment strategy for Epstein-Barr virus-positive Hodgkin's lymphoma," Int. J.Cancer, vol. 93, No. 5, pp. 706-713 (2001).
Kobayashi, et al., "Induction of EBV-Latent Membrane Protein 1-Specific MHC Class II-Restricted T-Cell Responses Against Natural Killer Lymphoma Cells," Cancer Research, vol. 68, No. 3, pp. 901-908 (2008).
Murray et al., Identification of Target Antigens for the Human Cytotoxic T Cell Response to Epstein-Barr virus (EBV): Implications for the Immune Control of EBV-positive malignancies, J. Exp. Med., vol. 176, No. 1, pp. 157-168 (1992).
International Preliminary Report on Patentability issued in related International Patent Application No. PCT/EP2013/055690, dated Oct. 2, 2014.
Decision on Refusal issued in co-pending Japanese Patent Application No. 2018-072812, dated Nov. 10, 2020.
Nishimura, "Structure and Function of Major Histocompatibility Antigens that Allow T Cells to Recognize Antigens," Protein, Nucleic Acid and Enzyme, vol. 45, No. 7, pp. 1205-1218 (2000).

* cited by examiner

SEQUENCE LISTING

```
<160> NUMBER OF SEQ ID NOS: 43

<210> SEQ ID NO 1
<211> LENGTH: 2661
<212> TYPE: DNA
<213> ORGANISM: Human herpesvirus 4

<400> SEQUENCE: 1
atggaggcag ccttgcttgt gtgtcagtac accatccaga gccttatcca actcacgcgt     60
gatgatcctg gttttttcaa tgttgagatt ctggaattcc cattttaccc agcgtgcaat    120
gtttgcacgg cagatgtcaa tgcaactatc aatttcgatg tcgggggcaa aaagcataaa    180
cttaatcttg actttggcct gctgacaccc catacaaagg ctgtctacca acctcgaggt    240
gcatttggtg gctcagaaaa tgccaccaat ctctttctac tggagctcct tggtgcagga    300
gaattggctc taactatgcg gtctaagaag cttccaatta acatcaccac cggagaggag    360
caacaagtaa gcctggaatc tgtagatgtc tactttcaag atgtgtttgg caccatgtgg    420
tgccaccatg cagaaatgca aaacccagta tacctaatac cagaaacagt gccatacata    480
aagtgggata actgtaattc taccaatata acggcagtag taagggcaca ggggctggat    540
gtcacgctac ccttaagttt gccaacatca gctcaagact cgaatttcag cgtaaaaaca    600
gaaatgctcg gtaatgagat agatattgag tgtattatgg aggatggcga aatttcacaa    660
gttctgcccg gagacaacaa atttaacatc acctgcagtg gatacgagag ccatgttccc    720
agcggcggaa ttctcacatc aacgagtccc gtggccaccc caatacctgg tacagggtat    780
gcatacagcc tgcgtctgac accacgtcca gtgtcacgat ttcttggcaa taacagtata    840
ctgtacgtgt tttactctgg gaatggaccg aaggcgagcg ggggagatta ctgcattcag    900
tccaacattg tgttctctga tgagattcca gcttcacagg acatgccgac aaacaccaca    960
gacatcacat atgtgggtga caatgctacc tattcagtgc caatggtcac ttctgaggac   1020
gcaaactcgc caaatgttac agtgactgcc ttttgggcct ggccaaacaa cactgaaact   1080
gactttaagt gcaaatggac tctcacctcg gggacacctt cgggttgtga aaatatttct   1140
ggtgcatttg cgagcaatcg gacatttgac attactgtct cgggtcttgg cacggccccc   1200
```

```
aagacactca ttatcacacg aacggctacc aatgccacca caacaaccca caaggttata    1260
ttctccaagg cacccgagag caccaccacc tcccctacct tgaatacaac tggatttgct    1320
gctcccaata caacgacagg tctacccagc tctactcacg tgcctaccaa cctcaccgca    1380
cctgcaagca caggccccac tgtatccacc gcggatgtca ccagcccaac ccagccggc     1440 acaacgtcag gcgcatcacc ggtgacacca gtccatctc cacgggacaa cggcacagaa     1500
agtaaggccc ccgacatgac cagcccccacc tcagcagtga ctaccccaac ccaaatgcc    1560 accagcccca cccagcagt gactacccca accccaaatg ccaccagccc caccttggga     1620
aaaacaagtc ccacctcagc agtgactacc caaccccaa atgccaccag ccccacccca     1680
gcagtgacta ccccaacccc aaatgccacc atccccacct tgggaaaaac aagtcccacc    1740
tcagcagtga ctacccccaac cccaaatgcc accagcccta ccgtgggaga acaagtcca    1800 caggcaaata ccaccaacca cacattagga ggaacaagtt ccaccccagt agttaccagc    1860
ccaccaaaaa atgcaaccag tgctgttacc acaggccaac ataacataac ttcaagttca    1920
acctcttcca tgtcactgag acccagttca atctcagaga cactcagccc ctccaccagt    1980
gacaattcaa cgtcacatat gcctttacta acctccgctc acccaacagg tggtgaaaat    2040
ataacacagg tgacaccagc ctctaccagc acacatcatg tgtccaccag ttcgccagcg    2100
ccccgcccag gcaccaccag ccaagcgtca ggccctggaa acagttccac atccacaaaa    2160 ccggggggagg ttaatgtcac caaaggcacg ccccccaaaa atgcaacgtc gccccaggcc    2220
cccagtggcc aaaagacggc ggttcccacg gtcacctcaa caggtggaaa ggccaattct    2280
accaccggtg gaaagcacac cacaggacat ggagcccgga caagtacaga gcccaccaca    2340
gattacggcg gtgattcaac tacgccaaga acgagataca atgcgaccac ctatctacct    2400
cccagcactt ctagcaaact gcggccccgc tggacttta cgagcccacc ggttaccaca     2460
gcccaagcca ccgtgcctgt cccgccaacg tcccagccca gattctcaaa cctctccatg    2520
ctagtactgc agtgggcctc tctggctgtg ctgacccttc tgctgctgct ggtcatggcg    2580
gactgcgcct tcaggcgtaa cttgtcgaca tcccatacct acaccaccc accatatgat     2640 gacgccgaga cctatgtata a                                              2661
```

<210> SEQ ID NO 2
<211> LENGTH: 886
<212> TYPE: PRT
<213> ORGANISM: Human herpesvirus 4

<400> SEQUENCE: 2

```
Met Glu Ala Ala Leu Val Cys Gln Tyr Thr Ile Gln Ser Leu Ile
1               5                   10                  15

Gln Leu Thr Arg Asp Asp Pro Gly Phe Phe Asn Val Glu Ile Leu Glu
            20                  25                  30

Phe Pro Phe Tyr Pro Ala Cys Asn Val Cys Thr Ala Asp Val Asn Ala
        35                  40                  45

Thr Ile Asn Phe Asp Val Gly Gly Lys Lys His Lys Leu Asn Leu Asp
    50                  55                  60

Phe Gly Leu Leu Thr Pro His Thr Lys Ala Val Tyr Gln Pro Arg Gly
65                  70                  75                  80

Ala Phe Gly Gly Ser Glu Asn Ala Thr Asn Leu Phe Leu Leu Glu Leu
                85                  90                  95

Leu Gly Ala Gly Glu Leu Ala Leu Thr Met Arg Ser Lys Lys Leu Pro
            100                 105                 110
```

```
Ile Asn Ile Thr Thr Gly Glu Glu Gln Gln Val Ser Leu Glu Ser Val
            115                 120                 125

Asp Val Tyr Phe Gln Asp Val Phe Gly Thr Met Trp Cys His His Ala
    130                 135                 140

Glu Met Gln Asn Pro Val Tyr Leu Ile Pro Glu Thr Val Pro Tyr Ile
145                 150                 155                 160

Lys Trp Asp Asn Cys Asn Ser Thr Asn Ile Thr Ala Val Val Arg Ala
                165                 170                 175

Gln Gly Leu Asp Val Thr Leu Pro Leu Ser Leu Pro Thr Ser Ala Gln
                180                 185                 190

Asp Ser Asn Phe Ser Val Lys Thr Glu Met Leu Gly Asn Glu Ile Asp
            195                 200                 205

Ile Glu Cys Ile Met Glu Asp Gly Glu Ile Ser Gln Val Leu Pro Gly
        210                 215                 220

Asp Asn Lys Phe Asn Ile Thr Cys Ser Gly Tyr Glu Ser His Val Pro
225                 230                 235                 240

Ser Gly Gly Ile Leu Thr Ser Thr Ser Pro Val Ala Thr Pro Ile Pro
                245                 250                 255

Gly Thr Gly Tyr Ala Tyr Ser Leu Arg Leu Thr Pro Arg Pro Val Ser
            260                 265                 270

Arg Phe Leu Gly Asn Asn Ser Ile Leu Tyr Val Phe Tyr Ser Gly Asn
        275                 280                 285

Gly Pro Lys Ala Ser Gly Gly Asp Tyr Cys Ile Gln Ser Asn Ile Val
        290                 295                 300

Phe Ser Asp Glu Ile Pro Ala Ser Gln Asp Met Pro Thr Asn Thr Thr
305                 310                 315                 320

Asp Ile Thr Tyr Val Gly Asp Asn Ala Thr Tyr Ser Val Pro Met Val
                325                 330                 335

Thr Ser Glu Asp Ala Asn Ser Pro Asn Val Thr Val Thr Ala Phe Trp
            340                 345                 350

Ala Trp Pro Asn Asn Thr Glu Thr Asp Phe Lys Cys Lys Trp Thr Leu
        355                 360                 365

Thr Ser Gly Thr Pro Ser Gly Cys Glu Asn Ile Ser Gly Ala Phe Ala
        370                 375                 380

Ser Asn Arg Thr Phe Asp Ile Thr Val Ser Gly Leu Gly Thr Ala Pro
385                 390                 395                 400

Lys Thr Leu Ile Ile Thr Arg Thr Ala Thr Asn Ala Thr Thr Thr Thr
                405                 410                 415

His Lys Val Ile Phe Ser Lys Ala Pro Glu Ser Thr Thr Ser Pro
            420                 425                 430

Thr Leu Asn Thr Thr Gly Phe Ala Ala Pro Asn Thr Thr Thr Gly Leu
        435                 440                 445

Pro Ser Ser Thr His Val Pro Thr Asn Leu Thr Ala Pro Ala Ser Thr
    450                 455                 460

Gly Pro Thr Val Ser Thr Ala Asp Val Thr Ser Pro Thr Pro Ala Gly
465                 470                 475                 480

Thr Thr Ser Gly Ala Ser Pro Val Thr Pro Ser Pro Ser Pro Arg Asp
                485                 490                 495

Asn Gly Thr Glu Ser Lys Ala Pro Asp Met Thr Ser Pro Thr Ser Ala
                500                 505                 510

Val Thr Thr Pro Thr Pro Asn Ala Thr Ser Pro Thr Pro Ala Val Thr
            515                 520                 525
```

-continued

Thr Pro Thr Pro Asn Ala Thr Ser Pro Thr Leu Gly Lys Thr Ser Pro
        530                 535                 540

Thr Ser Ala Val Thr Thr Pro Thr Pro Asn Ala Thr Ser Pro Thr Pro
545                 550                 555                 560

Ala Val Thr Thr Pro Thr Pro Asn Ala Thr Ile Pro Thr Leu Gly Lys
                565                 570                 575

Thr Ser Pro Thr Ser Ala Val Thr Thr Pro Thr Pro Asn Ala Thr Ser
            580                 585                 590

Pro Thr Val Gly Glu Thr Ser Pro Gln Ala Asn Thr Thr Asn His Thr
                595                 600                 605

Leu Gly Gly Thr Ser Ser Thr Pro Val Val Thr Ser Pro Pro Lys Asn
610                 615                 620

Ala Thr Ser Ala Val Thr Thr Gly Gln His Asn Ile Thr Ser Ser Ser
625                 630                 635                 640

Thr Ser Ser Met Ser Leu Arg Pro Ser Ser Ile Ser Glu Thr Leu Ser
                645                 650                 655

Pro Ser Thr Ser Asp Asn Ser Thr Ser His Met Pro Leu Leu Thr Ser
            660                 665                 670

Ala His Pro Thr Gly Gly Glu Asn Ile Thr Gln Val Thr Pro Ala Ser
            675                 680                 685

Thr Ser Thr His His Val Ser Thr Ser Ser Pro Ala Pro Arg Pro Gly
690                 695                 700

Thr Thr Ser Gln Ala Ser Gly Pro Gly Asn Ser Ser Thr Ser Thr Lys
705                 710                 715                 720

Pro Gly Glu Val Asn Val Thr Lys Gly Thr Pro Pro Lys Asn Ala Thr
                725                 730                 735

Ser Pro Gln Ala Pro Ser Gly Gln Lys Thr Ala Val Pro Thr Val Thr
            740                 745                 750

Ser Thr Gly Gly Lys Ala Asn Ser Thr Thr Gly Gly Lys His Thr Thr
            755                 760                 765

Gly His Gly Ala Arg Thr Ser Thr Glu Pro Thr Thr Asp Tyr Gly Gly
            770                 775                 780

Asp Ser Thr Thr Pro Arg Thr Arg Tyr Asn Ala Thr Thr Tyr Leu Pro
785                 790                 795                 800

Pro Ser Thr Ser Ser Lys Leu Arg Pro Arg Trp Thr Phe Thr Ser Pro
                805                 810                 815

Pro Val Thr Thr Ala Gln Ala Thr Val Pro Val Pro Pro Thr Ser Gln
                820                 825                 830

Pro Arg Phe Ser Asn Leu Ser Met Leu Val Leu Gln Trp Ala Ser Leu
            835                 840                 845

Ala Val Leu Thr Leu Leu Leu Leu Val Met Ala Asp Cys Ala Phe
850                 855                 860

Arg Arg Asn Leu Ser Thr Ser His Thr Tyr Thr Thr Pro Pro Tyr Asp
865                 870                 875                 880

Asp Ala Glu Thr Tyr Val
                885

<210> SEQ ID NO 3
<211> LENGTH: 4184
<212> TYPE: DNA
<213> ORGANISM: Homo sapiens

<400> SEQUENCE: 3
atttaagggc cgcctctcc tggctcacag ctgcttgctg ctccagcctt gccctcccag    60

| | |
|---|---|
| agctgccgga cgctcgcggg tctcggaacg catcccgccg cggggggcttc ggccgtggca | 120 |
| tgggcgccgc gggcctgctc ggggttttct tggctctcgt cgcaccgggg gtcctcggga | 180 |
| tttcttgtgg ctctcctccg cctatcctaa atggccggat tagttattat tctacccca | 240 |
| ttgctgttgg taccgtgata aggtacagtt gttcaggtac cttccgcctc attggagaaa | 300 |
| aaagtctatt atgcataact aaagacaaag tggatggaac ctgggataaa cctgctccta | 360 |
| aatgtgaata tttcaataaa tattcttctt gccctgagcc catagtacca ggaggataca | 420 |
| aaattagagg ctctacaccc tacagacatg gtgattctgt gcatttgcc tgtaaaacca | 480 |
| acttctccat gaacggaaac aagtctgttt ggtgtcaagc aaataatatg tggggccga | 540 |
| cacgactacc aacctgtgta agtgttttcc ctctcgagtg tccagcactt cctatgatcc | 600 |
| acaatggaca tcacacaagt gagaatgttg gctccattgc tccaggattg tctgtgactt | 660 |
| acagctgtga atctggttac ttgcttgttg gagaaaagat cattaactgt ttgtcttcgg | 720 |
| gaaaatggag tgctgtcccc cccacatgtg aagaggcacg ctgtaaatct ctaggacgat | 780 |
| ttcccaatgg gaaggtaaag gagcctcaa ttctccgggt tggtgtaact gcaaactttt | 840 |
| tctgtgatga agggtatcga ctgcaaggcc caccttctag tcggtgtgta attgctggac | 900 |
| agggagttgc ttggaccaaa atgccagtat gtgaagaaat tttttgccca tcacctcccc | 960 |
| ctattctcaa tggaagacat ataggcaact cactagcaaa tgtctcatat ggaagcatag | 1020 |
| tcacttacac ttgtgacccg gacccagagg aaggagtgaa cttcatcctt attggagaga | 1080 |
| gcactctccg ttgtacagtt gatagtcaga agactgggac ctggagtggc cctgccccac | 1140 |
| gctgtgaact ttctacttct gcggttcagt gtccacatcc ccagatccta agaggccgaa | 1200 |
| tggtatctgg gcagaaagat cgatatacct ataacgacac tgtgatattt gcttgcatgt | 1260 |
| ttggcttcac cttgaagggc agcaagcaaa tccgatgcaa tgcccaaggc acatgggagc | 1320 |
| catctgcacc agtctgtgaa aaggaatgcc aggcccctcc taacatcctc aatgggcaaa | 1380 |
| aggaagatag acacatggtc cgctttgacc ctggaacatc tataaaatat agctgtaacc | 1440 |
| ctggctatgt gctggtggga gaagaatcca tacagtgtac ctctgagggg gtgtggacac | 1500 |
| cccctgtacc ccaatgcaaa gtggcagcgt gtgaagctac aggaaggcaa ctcttgacaa | 1560 |
| aaccccagca ccaatttgtt agaccagatg tcaactcttc ttgtggtgaa gggtacaagt | 1620 |
| taagtgggag tgtttatcag gagtgtcaag gcacaattcc ttggtttatg gagattcgtc | 1680 |
| tttgtaaaga aatcacctgc ccaccacccc ctgttatcta caatggggca cacaccggga | 1740 |
| gttccttaga agattttcca tatggaacca cggtcactta cacatgtaac cctgggccag | 1800 |
| aaagaggagt ggaattcagc ctcattggag agagcaccat ccgttgtaca agcaatgatc | 1860 |
| aagaagagg cacctggagt ggccctgctc ccctgtgtaa actttccctc cttgctgtcc | 1920 |
| agtgctcaca tgtccatatt gcaaatggat acaagatatc tggcaaggaa gccccatatt | 1980 |
| tctacaatga cactgtgaca ttcaagtgtt atagtggatt tactttgaag gcagtagtc | 2040 |
| agattcgttg caaagctgat aacacctggg atcctgaaat accagtttgt gaaaaaggct | 2100 |
| gccagtcacc tcctgggctc accatggtc gtcatacagg tggaaatacg gtcttctttg | 2160 |
| tctctgggat gactgtagac tacacttgtg accctggcta tttgcttgtg ggaaacaaat | 2220 |
| ccattcactg tatgccttca ggaaattgga gtccttctgc cccacggtgt gaagaaacat | 2280 |
| gccagcatgt gagacagagt cttcaagaac ttccagctgg ttcacgtgtg gagctagtta | 2340 |
| atacgtcctg ccaagatggg taccagttga ctggacatgc ttatcagatg tgtcaagatg | 2400 |
| ctgaaaatgg aatttggttc aaaaagattc cactttgtaa agttattcac tgtcaccctc | 2460 |

-continued

```
caccagtgat tgtcaatggg aagcacacag gcatgatggc agaaaacttt ctatatggaa    2520
atgaagtctc ttatgaatgt gaccaaggat tctatctcct gggagagaaa aaattgcagt    2580
gcagaagtga ttctaaagga catggatctt ggagcgggcc ttccccacag tgcttacgat    2640
ctcctcctgt gactcgctgc cctaatccag aagtcaaaca tgggtacaag ctcaataaaa    2700
cacattctgc atattcccac aatgacatag tgtatgttga ctgcaatcct ggcttcatca    2760
tgaatggtag tcgcgtgatt aggtgtcata ctgataacac atgggtgcca ggtgtgccaa    2820
cttgtatcaa aaagccttc ataggtgtc cacctccgcc taagacccct aacgggaacc    2880
atactggtgg aaacatagct cgattttctc ctggaatgtc aatcctgtac agctgtgacc    2940
aaggctacct gctggtggga gaggcactcc ttctttgcac acatgaggga acctggagcc    3000
aacctgcccc tcattgtaaa gaggtaaact gtagctcacc agcagatatg gatgaatcc    3060 agaaagggct ggaaccaagg aaaatgtatc agtatggagc tgttgtaact ctggagtgtg    3120
aagatgggta tgctggaag gcagtcccc agagccagtg ccaatcggat caccaatgga    3180
accctcccct ggcggtttgc agatcccgtt cacttgctcc tgtcctttgt ggtattgctg    3240
caggtttgat acttcttacc ttcttgattg tcattacctt atacgtgata tcaaaacaca    3300
gagcacgcaa ttattataca gatacaagcc agaaagaagc ttttcattta gaagcacgag    3360
aagtatattc tgttgatcca tacaacccag ccagctgatc agaagacaaa ctggtgtgtg    3420
cctcattgct tggaattcag cggaatattg attagaaaga aactgctcta atatcagcaa    3480
gtctctttat atggcctcaa gatcaatgaa atgatgtcat aagcgatcac ttcctatatg    3540
cacttattct caagaagaac atctttatgg taaagatggg agcccagttt cactgccata    3600
tactcttcaa ggactttctg aagcctcact tatgagatgc ctgaagccag gccatggcta    3660
taaacaatta catggctcta aaagttttg ccctttttaa ggaaggcact aaaaagagct    3720
gtcctggtat ctagacccat cttcttttg aaatcagcat actcaatgtt actatctgct    3780
tttggttata atgtgttttt aattatctaa agtatgaagc attttctggg gttatgatgg    3840 ctttacccttt attaggaagt atggttttat tttgatagta gcttcctcct ctggtggtgt    3900
taatcatttc atttttaccc ttacttggtt tgagtttctc tcacattact gtatatactt    3960
tgcctttcca taatcactca gtgattgcaa tttgcacaag ttttttttaaa ttatgggaat    4020 caagatttaa tcctagagat ttggtgtaca attcaggctt tggatgtttc tttagcagtt    4080
ttgtgataag ttctagttgc ttgtaaaatt tcacttaata atgtgtacat tagtcattca    4140
ataaattgta attgtaaaga aaacatacaa aaaaaaaaa aaaa                      4184
```

<210> SEQ ID NO 4
<211> LENGTH: 1092
<212> TYPE: PRT
<213> ORGANISM: Homo sapiens

<400> SEQUENCE: 4

Met Gly Ala Ala Gly Leu Leu Gly Val Phe Leu Ala Leu Val Ala Pro
1               5                   10                  15

Gly Val Leu Gly Ile Ser Cys Gly Ser Pro Pro Pro Ile Leu Asn Gly
                20                  25                  30

Arg Ile Ser Tyr Tyr Ser Thr Pro Ile Ala Val Gly Thr Val Ile Arg
            35                  40                  45

Tyr Ser Cys Ser Gly Thr Phe Arg Leu Ile Gly Glu Lys Ser Leu Leu
        50                  55                  60

```
Cys Ile Thr Lys Asp Lys Val Asp Gly Thr Trp Asp Lys Pro Ala Pro
 65                  70                  75                  80

Lys Cys Glu Tyr Phe Asn Lys Tyr Ser Ser Cys Pro Glu Pro Ile Val
                 85                  90                  95

Pro Gly Gly Tyr Lys Ile Arg Gly Ser Thr Pro Tyr Arg His Gly Asp
            100                 105                 110

Ser Val Thr Phe Ala Cys Lys Thr Asn Phe Ser Met Asn Gly Asn Lys
            115                 120                 125

Ser Val Trp Cys Gln Ala Asn Asn Met Trp Gly Pro Thr Arg Leu Pro
            130                 135                 140

Thr Cys Val Ser Val Phe Pro Leu Glu Cys Pro Ala Leu Pro Met Ile
145                 150                 155                 160

His Asn Gly His His Thr Ser Glu Asn Val Gly Ser Ile Ala Pro Gly
                165                 170                 175

Leu Ser Val Thr Tyr Ser Cys Glu Ser Gly Tyr Leu Leu Val Gly Glu
            180                 185                 190

Lys Ile Ile Asn Cys Leu Ser Ser Gly Lys Trp Ser Ala Val Pro Pro
            195                 200                 205

Thr Cys Glu Glu Ala Arg Cys Lys Ser Leu Gly Arg Phe Pro Asn Gly
210                 215                 220

Lys Val Lys Glu Pro Pro Ile Leu Arg Val Gly Val Thr Ala Asn Phe
225                 230                 235                 240

Phe Cys Asp Glu Gly Tyr Arg Leu Gln Gly Pro Pro Ser Ser Arg Cys
                245                 250                 255

Val Ile Ala Gly Gln Gly Val Ala Trp Thr Lys Met Pro Val Cys Glu
            260                 265                 270

Glu Ile Phe Cys Pro Ser Pro Pro Ile Leu Asn Gly Arg His Ile
            275                 280                 285

Gly Asn Ser Leu Ala Asn Val Ser Tyr Gly Ser Ile Val Thr Tyr Thr
            290                 295                 300

Cys Asp Pro Asp Pro Glu Glu Gly Val Asn Phe Ile Leu Ile Gly Glu
305                 310                 315                 320

Ser Thr Leu Arg Cys Thr Val Asp Ser Gln Lys Thr Gly Thr Trp Ser
                325                 330                 335

Gly Pro Ala Pro Arg Cys Glu Leu Ser Thr Ser Ala Val Gln Cys Pro
            340                 345                 350

His Pro Gln Ile Leu Arg Gly Arg Met Val Ser Gly Gln Lys Asp Arg
            355                 360                 365

Tyr Thr Tyr Asn Asp Thr Val Ile Phe Ala Cys Met Phe Gly Phe Thr
            370                 375                 380

Leu Lys Gly Ser Lys Gln Ile Arg Cys Asn Ala Gln Gly Thr Trp Glu
385                 390                 395                 400

Pro Ser Ala Pro Val Cys Glu Lys Glu Cys Gln Ala Pro Pro Asn Ile
                405                 410                 415

Leu Asn Gly Gln Lys Glu Asp Arg His Met Val Arg Phe Asp Pro Gly
            420                 425                 430

Thr Ser Ile Lys Tyr Ser Cys Asn Pro Gly Tyr Val Leu Val Gly Glu
            435                 440                 445

Glu Ser Ile Gln Cys Thr Ser Glu Gly Val Trp Thr Pro Pro Val Pro
            450                 455                 460

Gln Cys Lys Val Ala Ala Cys Glu Ala Thr Gly Arg Gln Leu Leu Thr
465                 470                 475                 480

Lys Pro Gln His Gln Phe Val Arg Pro Asp Val Asn Ser Ser Cys Gly
```

```
                485                 490                 495
Glu Gly Tyr Lys Leu Ser Gly Ser Val Tyr Gln Glu Cys Gln Gly Thr
            500                 505                 510
Ile Pro Trp Phe Met Glu Ile Arg Leu Cys Lys Glu Ile Thr Cys Pro
            515                 520                 525
Pro Pro Pro Val Ile Tyr Asn Gly Ala His Thr Gly Ser Ser Leu Glu
530                 535                 540
Asp Phe Pro Tyr Gly Thr Thr Val Thr Tyr Thr Cys Asn Pro Gly Pro
545                 550                 555                 560
Glu Arg Gly Val Glu Phe Ser Leu Ile Gly Glu Ser Thr Ile Arg Cys
                565                 570                 575
Thr Ser Asn Asp Gln Glu Arg Gly Thr Trp Ser Gly Pro Ala Pro Leu
            580                 585                 590
Cys Lys Leu Ser Leu Leu Ala Val Gln Cys Ser His Val His Ile Ala
            595                 600                 605
Asn Gly Tyr Lys Ile Ser Gly Lys Glu Ala Pro Tyr Phe Tyr Asn Asp
            610                 615                 620
Thr Val Thr Phe Lys Cys Tyr Ser Gly Phe Thr Leu Lys Gly Ser Ser
625                 630                 635                 640
Gln Ile Arg Cys Lys Ala Asp Asn Thr Trp Asp Pro Glu Ile Pro Val
                645                 650                 655
Cys Glu Lys Gly Cys Gln Ser Pro Pro Gly Leu His His Gly Arg His
            660                 665                 670
Thr Gly Gly Asn Thr Val Phe Phe Val Ser Gly Met Thr Val Asp Tyr
            675                 680                 685
Thr Cys Asp Pro Gly Tyr Leu Leu Val Gly Asn Lys Ser Ile His Cys
690                 695                 700
Met Pro Ser Gly Asn Trp Ser Pro Ser Ala Pro Arg Cys Glu Glu Thr
705                 710                 715                 720
Cys Gln His Val Arg Gln Ser Leu Gln Glu Leu Pro Ala Gly Ser Arg
                725                 730                 735
Val Glu Leu Val Asn Thr Ser Cys Gln Asp Gly Tyr Gln Leu Thr Gly
            740                 745                 750
His Ala Tyr Gln Met Cys Gln Asp Ala Glu Asn Gly Ile Trp Phe Lys
            755                 760                 765
Lys Ile Pro Leu Cys Lys Val Ile His Cys His Pro Pro Pro Val Ile
            770                 775                 780
Val Asn Gly Lys His Thr Gly Met Met Ala Glu Asn Phe Leu Tyr Gly
785                 790                 795                 800
Asn Glu Val Ser Tyr Glu Cys Asp Gln Gly Phe Tyr Leu Leu Gly Glu
                805                 810                 815
Lys Lys Leu Gln Cys Arg Ser Asp Ser Lys Gly His Gly Ser Trp Ser
            820                 825                 830
Gly Pro Ser Pro Gln Cys Leu Arg Ser Pro Pro Val Thr Arg Cys Pro
            835                 840                 845
Asn Pro Glu Val Lys His Gly Tyr Lys Leu Asn Lys Thr His Ser Ala
            850                 855                 860
Tyr Ser His Asn Asp Ile Val Tyr Val Asp Cys Asn Pro Gly Phe Ile
865                 870                 875                 880
Met Asn Gly Ser Arg Val Ile Arg Cys His Thr Asp Asn Thr Trp Val
                885                 890                 895
Pro Gly Val Pro Thr Cys Ile Lys Lys Ala Phe Ile Gly Cys Pro Pro
            900                 905                 910
```

```
Pro Pro Lys Thr Pro Asn Gly Asn His Thr Gly Gly Asn Ile Ala Arg
        915                 920                 925

Phe Ser Pro Gly Met Ser Ile Leu Tyr Ser Cys Asp Gln Gly Tyr Leu
        930                 935                 940

Leu Val Gly Glu Ala Leu Leu Leu Cys Thr His Glu Gly Thr Trp Ser
945                 950                 955                 960

Gln Pro Ala Pro His Cys Lys Glu Val Asn Cys Ser Ser Pro Ala Asp
                965                 970                 975

Met Asp Gly Ile Gln Lys Gly Leu Glu Pro Arg Lys Met Tyr Gln Tyr
            980                 985                 990

Gly Ala Val Val Thr Leu Glu Cys Glu Asp Gly Tyr Met Leu Glu Gly
        995                 1000                1005

Ser Pro Gln Ser Gln Cys Gln Ser Asp His Gln Trp Asn Pro Pro
    1010                1015                1020

Leu Ala Val Cys Arg Ser Arg Ser Leu Ala Pro Val Leu Cys Gly
    1025                1030                1035

Ile Ala Ala Gly Leu Ile Leu Leu Thr Phe Leu Ile Val Ile Thr
    1040                1045                1050

Leu Tyr Val Ile Ser Lys His Arg Ala Arg Asn Tyr Tyr Thr Asp
    1055                1060                1065

Thr Ser Gln Lys Glu Ala Phe His Leu Glu Ala Arg Glu Val Tyr
    1070                1075                1080

Ser Val Asp Pro Tyr Asn Pro Ala Ser
    1085                1090
```

<210> SEQ ID NO 5
<211> LENGTH: 4007
<212> TYPE: DNA
<213> ORGANISM: Homo sapiens

<400> SEQUENCE: 5

```
atttaagggc cgcctctcc  tggctcacag ctgcttgctg ctccagcctt gccctcccag    60
agctgccgga cgctcgcggg tctcggaacg catcccgccg cggggctta  ggccgtggca   120
tgggcgccgc gggcctgctc gggttttct  tggctctcgt cgcaccgggg gtcctcggga   180
tttcttgtgg ctctcctccg cctatcctaa atggccggat tagttattat tctacccca   240
ttgctgttgg taccgtgata aggtacagtt gttcaggtac cttccgcctc attggagaaa   300
aaagtctatt atgcataact aaagacaaag tggatggaac ctgggataaa cctgctccta   360
aatgtgaata tttcaataaa tattcttctt gccctgagcc catagtacca ggaggataca   420
aaattagagg ctctacaccc tacagacatg gtgattctgt gcatttgcc  tgtaaaacca   480
acttctccat gaacggaaac aagtctgttt ggtgtcaagc aaataatatg tgggggccga   540
cacgactacc aacctgtgta agtgttttcc ctctcgagtg tccagcactt cctatgatcc   600
acaatggaca tcacacaagt gagaatgttg gctccattgc tccaggattg tctgtgactt   660
acagctgtga atctggttac ttgcttgttg agaaaagat  cattaactgt ttgtcttcgg   720
gaaaatggag tgctgtcccc cccacatgtg aagaggcacg ctgtaaatct ctaggacgat   780
ttcccaatgg gaaggtaaag gagcctccaa ttctccgggt tggtgtaact gcaaactttt   840
tctgtgatga agggtatcga ctgcaaggcc  accttctag tcggtgtgta attgctggac   900
agggagttgc ttggaccaaa atgccagtat gtgaagaaat ttttgccca tcacctcccc   960
ctattctcaa tggaagacat ataggcaact cactagcaaa tgtctcatat ggaagcatag  1020
```

```
tcacttacac ttgtgacccg gacccagagg aaggagtgaa cttcatcctt attggagaga    1080
gcactctccg ttgtacagtt gatagtcaga agactgggac ctggagtggc cctgccccac    1140
gctgtgaact ttctacttct gcggttcagt gtccacatcc ccagatccta agaggccgaa    1200
tggtatctgg gcagaaagat cgatatacct ataacgacac tgtgatattt gcttgcatgt    1260
ttggcttcac cttgaagggc agcaagcaaa tccgatgcaa tgcccaaggc acatgggagc    1320
catctgcacc agtctgtgaa aaggaatgcc aggcccctcc taacatcctc aatgggcaaa    1380
aggaagatag acacatggtc cgctttgacc ctggaacatc tataaaatat agctgtaacc    1440
ctggctatgt gctggtggga gaagaatcca tacagtgtac ctctgagggg gtgtggacac    1500
cccctgtacc ccaatgcaaa gtggcagcgt gtgaagctac aggaaggcaa ctcttgacaa    1560
aaccccagca ccaatttgtt agaccagatg tcaactcttc ttgtggtgaa gggtacaagt    1620
taagtgggag tgtttatcag gagtgtcaag gcacaattcc ttggtttatg gagattcgtc    1680
tttgtaaaga aatcacctgc ccaccacccc ctgttatcta caatgggggca cacaccggga    1740
gttccttaga agattttcca tatggaacca cggtcactta cacatgtaac cctgggccag    1800
aaagaggagt ggaattcagc ctcattggag agagcaccat ccgttgtaca agcaatgatc    1860
aagaaagagg cacctggagt ggccctgctc ccctgtgtaa actttccctc cttgctgtcc    1920
agtgctcaca tgtccatatt gcaaatggat acaagatatc tggcaaggaa gccccatatt    1980
tctacaatga cactgtgaca ttcaagtgtt atagtggatt tactttgaag ggcagtagtc    2040
agattcgttg caaagctgat aacacctggg atcctgaaat accagtttgt gaaaaagaaa    2100
catgccagca tgtgagacag agtcttcaag aacttccagc tggttcacgt gtggagctag    2160
ttaatacgtc ctgccaagat gggtaccagt tgactggaca tgcttatcag atgtgtcaag    2220
atgctgaaaa tggaatttgg ttcaaaaaga ttccactttg taaagttatt cactgtcacc    2280
ctccaccagt gattgtcaat gggaagcaca caggcatgat ggcagaaaac tttctatatg    2340
gaaatgaagt ctcttatgaa tgtgaccaag gattctatct cctgggagag aaaaaattgc    2400
agtgcagaag tgattctaaa ggacatggat cttggagcgg gccttcccca cagtgcttac    2460
gatctcctcc tgtgactcgc tgccctaatc cagaagtcaa acatgggtac aagctcaata    2520
aaacacattc tgcatattcc cacaatgaca tagtgtatgt tgactgcaat cctggcttca    2580
tcatgaatgg tagtcgcgtg attaggtgtc atactgataa cacatgggtg ccaggtgtgc    2640
caacttgtat caaaaaagcc ttcatagggt gtccacctcc gcctaagacc cctaacggga    2700
accatactgg tggaaacata gctcgatttt ctcctggaat gtcaatcctg tacagctgtg    2760
accaaggcta cctgctggtg ggagaggcac tccttctttg cacacatgag ggaacctgga    2820
gccaacctgc ccctcattgt aaagaggtaa actgtagctc accagcagat atggatggaa    2880
tccagaaagg gctggaacca aggaaaatgt atcagtatgg agctgttgta actctggagt    2940
gtgaagatgg gtatatgctg gaaggcagtc cccagagcca gtgccaatcg gatcaccaat    3000
ggaaccctcc cctggcggtt tgcagatccc gttcacttgc cctgtccttt gtggtattg    3060
ctgcaggttt gatacttctt accttcttga ttgtcattac cttatacgtg atatcaaaac    3120
acagagcacg caattattat acagatacaa gccagaaaga agcttttcat ttagaagcac    3180
gagaagtata ttctgttgat ccatacaacc cagccagctg atcagaagac aaactggtgt    3240
gtgcctcatt gcttggaatt cagcggaata ttgattagaa agaaactgct ctaatatcag    3300
caagtctctt tatatggcct caagatcaat gaaatgatgt cataagcgat cacttcctat    3360
atgcacttat tctcaagaag aacatctttta tggtaaagat gggagcccag tttcactgcc    3420
```

-continued

```
atatactctt caaggacttt ctgaagcctc acttatgaga tgcctgaagc caggccatgg   3480
ctataaacaa ttcatggct ctaaaaagtt ttgccctttt taaggaaggc actaaaaaga    3540
gctgtcctgg tatctagacc catcttcttt ttgaaatcag catactcaat gttactatct   3600
gcttttggtt ataatgtgtt tttaattatc taaagtatga agcattttct ggggttatga   3660
tggctttacc tttattagga agtatggttt tattttgata gtagcttcct cctctggtgg   3720
tgttaatcat ttcatttta cccttacttg gtttgagttt ctctcacatt actgtatata    3780
ctttgccttt ccataatcac tcagtgattg caatttgcac aagttttttt aaattatggg   3840
aatcaagatt taatcctaga gatttggtgt acaattcagg ctttggatgt ttctttagca   3900
gttttgtgat aagttctagt tgcttgtaaa atttcactta ataatgtgta cattagtcat   3960
tcaataaatt gtaattgtaa agaaaacata caaaaaaaaa aaaaaaa              4007
```

<210> SEQ ID NO 6
<211> LENGTH: 1033
<212> TYPE: PRT
<213> ORGANISM: Homo sapiens

<400> SEQUENCE: 6

```
Met Gly Ala Ala Gly Leu Leu Gly Val Phe Leu Ala Leu Val Ala Pro
1               5                   10                  15

Gly Val Leu Gly Ile Ser Cys Gly Ser Pro Pro Pro Ile Leu Asn Gly
            20                  25                  30

Arg Ile Ser Tyr Tyr Ser Thr Pro Ile Ala Val Gly Thr Val Ile Arg
        35                  40                  45

Tyr Ser Cys Ser Gly Thr Phe Arg Leu Ile Gly Glu Lys Ser Leu Leu
    50                  55                  60

Cys Ile Thr Lys Asp Lys Val Asp Gly Thr Trp Asp Lys Pro Ala Pro
65                  70                  75                  80

Lys Cys Glu Tyr Phe Asn Lys Tyr Ser Ser Cys Pro Glu Pro Ile Val
                85                  90                  95

Pro Gly Gly Tyr Lys Ile Arg Gly Ser Thr Pro Tyr Arg His Gly Asp
            100                 105                 110

Ser Val Thr Phe Ala Cys Lys Thr Asn Phe Ser Met Asn Gly Asn Lys
        115                 120                 125

Ser Val Trp Cys Gln Ala Asn Asn Met Trp Gly Pro Thr Arg Leu Pro
    130                 135                 140

Thr Cys Val Ser Val Phe Pro Leu Glu Cys Pro Ala Leu Pro Met Ile
145                 150                 155                 160

His Asn Gly His His Thr Ser Glu Asn Val Gly Ser Ile Ala Pro Gly
                165                 170                 175

Leu Ser Val Thr Tyr Ser Cys Glu Ser Gly Tyr Leu Leu Val Gly Glu
            180                 185                 190

Lys Ile Ile Asn Cys Leu Ser Ser Gly Lys Trp Ser Ala Val Pro Pro
        195                 200                 205

Thr Cys Glu Glu Ala Arg Cys Lys Ser Leu Gly Arg Phe Pro Asn Gly
    210                 215                 220

Lys Val Lys Glu Pro Pro Ile Leu Arg Val Gly Val Thr Ala Asn Phe
225                 230                 235                 240

Phe Cys Asp Glu Gly Tyr Arg Leu Gln Gly Pro Pro Ser Ser Arg Cys
                245                 250                 255

Val Ile Ala Gly Gln Gly Val Ala Trp Thr Lys Met Pro Val Cys Glu
            260                 265                 270
```

```
Glu Ile Phe Cys Pro Ser Pro Pro Ile Leu Asn Gly Arg His Ile
        275                 280                 285

Gly Asn Ser Leu Ala Asn Val Ser Tyr Gly Ser Ile Val Thr Tyr Thr
        290                 295                 300

Cys Asp Pro Asp Pro Glu Glu Gly Val Asn Phe Ile Leu Ile Gly Glu
305                 310                 315                 320

Ser Thr Leu Arg Cys Thr Val Asp Ser Gln Lys Thr Gly Thr Trp Ser
                325                 330                 335

Gly Pro Ala Pro Arg Cys Glu Leu Ser Thr Ser Ala Val Gln Cys Pro
                340                 345                 350

His Pro Gln Ile Leu Arg Gly Arg Met Val Ser Gly Gln Lys Asp Arg
        355                 360                 365

Tyr Thr Tyr Asn Asp Thr Val Ile Phe Ala Cys Met Phe Gly Phe Thr
        370                 375                 380

Leu Lys Gly Ser Lys Gln Ile Arg Cys Asn Ala Gln Gly Thr Trp Glu
385                 390                 395                 400

Pro Ser Ala Pro Val Cys Glu Lys Glu Cys Gln Ala Pro Pro Asn Ile
                405                 410                 415

Leu Asn Gly Gln Lys Glu Asp Arg His Met Val Arg Phe Asp Pro Gly
        420                 425                 430

Thr Ser Ile Lys Tyr Ser Cys Asn Pro Gly Tyr Val Leu Val Gly Glu
        435                 440                 445

Glu Ser Ile Gln Cys Thr Ser Glu Gly Val Trp Thr Pro Pro Val Pro
450                 455                 460

Gln Cys Lys Val Ala Ala Cys Glu Ala Thr Gly Arg Gln Leu Leu Thr
465                 470                 475                 480

Lys Pro Gln His Gln Phe Val Arg Pro Asp Val Asn Ser Ser Cys Gly
                485                 490                 495

Glu Gly Tyr Lys Leu Ser Gly Ser Val Tyr Gln Glu Cys Gln Gly Thr
                500                 505                 510

Ile Pro Trp Phe Met Glu Ile Arg Leu Cys Lys Glu Ile Thr Cys Pro
        515                 520                 525

Pro Pro Pro Val Ile Tyr Asn Gly Ala His Thr Gly Ser Ser Leu Glu
        530                 535                 540

Asp Phe Pro Tyr Gly Thr Thr Val Thr Tyr Thr Cys Asn Pro Gly Pro
545                 550                 555                 560

Glu Arg Gly Val Glu Phe Ser Leu Ile Gly Glu Ser Thr Ile Arg Cys
                565                 570                 575

Thr Ser Asn Asp Gln Glu Arg Gly Thr Trp Ser Gly Pro Ala Pro Leu
                580                 585                 590

Cys Lys Leu Ser Leu Leu Ala Val Gln Cys Ser His Val His Ile Ala
        595                 600                 605

Asn Gly Tyr Lys Ile Ser Gly Lys Glu Ala Pro Tyr Phe Tyr Asn Asp
        610                 615                 620

Thr Val Thr Phe Lys Cys Tyr Ser Gly Phe Thr Leu Lys Gly Ser Ser
625                 630                 635                 640

Gln Ile Arg Cys Lys Ala Asp Asn Thr Trp Asp Pro Glu Ile Pro Val
                645                 650                 655

Cys Glu Lys Glu Thr Cys Gln His Val Arg Gln Ser Leu Gln Glu Leu
                660                 665                 670

Pro Ala Gly Ser Arg Val Glu Leu Val Asn Thr Ser Cys Gln Asp Gly
        675                 680                 685
```

```
Tyr Gln Leu Thr Gly His Ala Tyr Gln Met Cys Gln Asp Ala Glu Asn
690                 695                 700

Gly Ile Trp Phe Lys Lys Ile Pro Leu Cys Lys Val Ile His Cys His
705                 710                 715                 720

Pro Pro Pro Val Ile Val Asn Gly Lys His Thr Gly Met Met Ala Glu
                725                 730                 735

Asn Phe Leu Tyr Gly Asn Glu Val Ser Tyr Glu Cys Asp Gln Gly Phe
                740                 745                 750

Tyr Leu Leu Gly Glu Lys Lys Leu Gln Cys Arg Ser Asp Ser Lys Gly
            755                 760                 765

His Gly Ser Trp Ser Gly Pro Ser Pro Gln Cys Leu Arg Ser Pro Pro
770                 775                 780

Val Thr Arg Cys Pro Asn Pro Glu Val Lys His Gly Tyr Lys Leu Asn
785                 790                 795                 800

Lys Thr His Ser Ala Tyr Ser His Asn Asp Ile Val Tyr Val Asp Cys
                805                 810                 815

Asn Pro Gly Phe Ile Met Asn Gly Ser Arg Val Ile Arg Cys His Thr
            820                 825                 830

Asp Asn Thr Trp Val Pro Gly Val Pro Thr Cys Ile Lys Lys Ala Phe
835                 840                 845

Ile Gly Cys Pro Pro Pro Lys Thr Pro Asn Gly Asn His Thr Gly
850                 855                 860

Gly Asn Ile Ala Arg Phe Ser Pro Gly Met Ser Ile Leu Tyr Ser Cys
865                 870                 875                 880

Asp Gln Gly Tyr Leu Leu Val Gly Glu Ala Leu Leu Leu Cys Thr His
                885                 890                 895

Glu Gly Thr Trp Ser Gln Pro Ala Pro His Cys Lys Glu Val Asn Cys
            900                 905                 910

Ser Ser Pro Ala Asp Met Asp Gly Ile Gln Lys Gly Leu Glu Pro Arg
            915                 920                 925

Lys Met Tyr Gln Tyr Gly Ala Val Val Thr Leu Glu Cys Glu Asp Gly
930                 935                 940

Tyr Met Leu Glu Gly Ser Pro Gln Ser Gln Cys Gln Ser Asp His Gln
945                 950                 955                 960

Trp Asn Pro Pro Leu Ala Val Cys Arg Ser Arg Ser Leu Ala Pro Val
                965                 970                 975

Leu Cys Gly Ile Ala Ala Gly Leu Ile Leu Leu Thr Phe Leu Ile Val
            980                 985                 990

Ile Thr Leu Tyr Val Ile Ser Lys His Arg Ala Arg Asn Tyr Tyr Thr
        995                 1000                1005

Asp Thr Ser Gln Lys Glu Ala Phe His Leu Glu Ala Arg Glu Val
    1010                1015                1020

Tyr Ser Val Asp Pro Tyr Asn Pro Ala Ser
    1025                1030

<210> SEQ ID NO 7
<211> LENGTH: 7409
<212> TYPE: DNA
<213> ORGANISM: Homo sapiens

<400> SEQUENCE: 7
aggcccctgc ctgccccagc atccctgcg cgaagctggg tgccccggag agtctgacca       60
ccatgccacc tcctcgcctc ctcttcttcc tcctcttcct caccccatg gaagtcaggc      120 ccgaggaacc tctagtggtg aaggtggaag gtatgtccaa aggcagaaa gggaagggat      180
```

```
tgaggctgga aacttgagtt gtggctgggt gtccttggct gagtaactta ccctctctga    240
gcctccattt tcttatttgt aaaattcagg aaagggttgg aaggactctg ccggctcctc    300
cactcccagc ttttggagtc ctctgctcta taacctggtg tgaggagtcg ggggcttgg     360
aggtcccccc cacccatgcc cacacctctc tccctctctc tccacagagg gagataacgc    420
tgtgctgcag tgcctcaagg ggacctcaga tggccccact cagcagctga cctggtctcg    480
ggagtccccg cttaaaccct tcttaaaact cagcctgggg ctgccaggcc tgggaatcca    540
catgaggccc ctggccatct ggcttttcat cttcaacgtc tctcaacaga tggggggctt    600
ctacctgtgc cagccggggc cccctctga aaggcctgg cagcctggct ggacagtcaa     660
tgtggagggc agcggtgagg gccgggctgg ggcaggggca ggaggagaga agggaggcca    720
ccatggacag aagaggtccg cggccacaat ggagctggag agaggggctg gagggattga    780
gggcgaaact cggagctagg tgggcagact cctggggctt cgtggcttca gtatgagctg    840
cttcctgtcc ctctacctct cactgtcttc tctctctctg cgggtctttg tctctattta    900
tctctgtctt tgagtctcta tctctctccc tctcctgggt gtctctgcat ttggttctgg    960
gtctcttccc aggggagctg ttccggtgga atgtttcgga cctaggtggc ctgggctgtg   1020
gcctgaagaa caggtcctca gagggcccca gctccccttc cgggaagctc atgagcccca   1080
agctgtatgt gtgggccaaa gaccgccctg agatctggga gggagagcct ccgtgtctcc   1140
caccgaggga cagcctgaac cagagcctca gccagggtat ggtgatgact ggggagatgc   1200
cgggaagcgg gggtccagag acagagggga ggggaaactg aagaggtgaa accctgagga   1260
tcaggctttc cttgtcttat ctctccctgt cccagacctc accatggccc ctggctccac   1320
actctggctg tcctgtgggg tacccctga ctctgtgtcc aggggccccc tctcctggac    1380
ccatgtgcac cccaaggggc ctaagtcatt gctgagccta gagctgaagg acgatcgccc   1440
ggccagagat atgtgggtaa tggagacggg tctgttgttg ccccgggcca cagctcaaga   1500
cgctggaaag tattattgtc accgtggcaa cctgaccatg tcattccacc tggagatcac   1560
tgctcggcca ggtagagttt ctctcaactg ggaggcatct gtgtggggt actgggaaga   1620
agtggaagcc agtcaatctt agattccccc aacccgaggg ctactcccag cctcacccca   1680
aaccccaact tccacacaga acactgactc caagtctttc ttttttttga cagagtctcg   1740
ctctgttgcc taggctggag tgcagtggtg ccatcttgtc ttggctcact gcaacctccg   1800
cctcccaggt tcaagtgatt cccctgcctc agcctcctga gtagctggga ttacaggtgc   1860
ccaccaccac gcctggctaa ttttttttttt tttttgaga cggagtcttg cactgtcacc   1920
caggctggag tgcagtggca cgatctcagc tcactgcaac ctccaccttc caggttcaag   1980
tgattctcct gcctcagcct cccgagtagc tgggattaaa gcctggctaa tttttttgt    2040
atttttagta gagatggggt ttcattatgt tggccaggct ggtctcaaac tcctgacctc    2100
gtgatccacc cgcctcggcc tcccaaagtg ctgggattac agacatgagc cacagggccg   2160
ggccaagcct aattttgtat ttttagtaga gatgggtttt ctccctgttg gaccaggctg   2220
gtcttgaact cctgacttca ggtgatctgc ctgccttggc ctcccaaagt actgggatta   2280
caggcataag ccaccgcacc tggcctagac ttcaagtctt cttccctcg cttccaagac    2340
actactttc tgggtcttca cctaccattg cttgcgcctg ccaccagct tgggtggagt     2400
cttccttcct cccaactcc tcactcttgg agccctgggc cctcttctta tccctgtctg    2460
cacactttcc tatttgaact tgactctcaa tggcttcttg ggtcaccatg ccttggtgac   2520
```

-continued

```
tctattccag gctccatact cagccatctc ctgtgccatt tgatatccca tggacacctc      2580
aggctcaaca gatacaaaat caaactcaat gtcttcccca agtatagtct tcttggtggc      2640
ccagtgtaag cagagggcac caccacctgc tccctcgccc aggctaagaa cctgggcatc      2700
cttcttttc ctcaccccgt ccaacaaact ggtcacagtg ttctgccaat tctctctcca       2760
tgcaatccta tcatgctatc ctaactgcaa ttcacaaacc caaccccaac tttcactcca      2820
aacttgatcc aagcaatgtg ctggatccca actgtaacct tgcaaactca actctgccct      2880
tcactttgac cgtgactatc cttaattgca gcaggaaact gatcattatg ctcccctcaa      2940
tccacacatt gcctctgagt acagccatgg tttgtccacg atttgctcaa agacactgcc      3000
ccatgtcctg tgccagggtc tgtgacaatc cctgacctcc tgggacatgg ctccttagag      3060
agaggagagc ctttctcaca gcttgggact ttgagtctgt gtcttttttt ttttcttgag      3120
acggagtttt gctgtggttg cccaggctgg agtgcagtga tctcggctca ctgaaacctc      3180
cgcctcccgg gttcaaacga ttctcctgcc tcagcctccc aagtagctgg gattacaggc      3240
acccaccacc atgcccagct aatttttttg tatttttagt agagatgggg tttcaccatg      3300
ttggccaggc tggtctcgaa ctcctgacct caggtgatcc accgcctttt gcctcccaaa      3360
gtgctgggat tacaggcgtc aaccaccgcg cccggccgag tctgtgtctt gcctctgtgc      3420
ctcagacttg cggttccttg agatctcagg attgggacgt aagatgccag cctggggtcc      3480
tcgtctcata gccccttccc cctagtacta tggcactggc tgctgaggac tggtggctgg      3540
aaggtctcag ctgtgacttt ggcttatctg atcttctgcc tgtgttccct tgtgggcatt      3600
cttcatcttc aaagaggtga gtcatgtccc cagtgggtct gtccaaaccc tactccatct      3660
tccccaggat aagccggctc tggccagtct gacaaccatc tttctttcct cccatccctc      3720
ccttcaagac cccagaatcc tgttctcccc agtcttcctc tagcctccct caaacttccc      3780
aagcctcttg caattttttt tttttttttg agacagggtc tcattctgtc accccagctg      3840
gagtgcagtg gcacaatctg agctcactgt aacctctgcc tcccaggctt aagtgattct      3900
tgtgcttcag cctcccgagt acctgggact acaagtgtat gccaccacac ccggccaatt      3960
ttttatattt ttagtagaga cgaggtttca ccatgttggc cagactggtc tcgaactctt      4020
gacctcaaat gatccgccca cctcggcctc ccaaagtgct gggattacag cacgagcca     4080
ccgcgcccgt ccgcctcgca atttgaactc ctgtctcctt tgttgaacca agtgacctcc     4140
ccagcacctg gccccacaaa tcctcaccct gccaagcagc cctcctctg atcacgccct      4200
ttaactccca ccagccctgg tcctgaggag gaaaagaaag cgaatgactg accccaccag     4260
gaggtaatgc aaccagtgca ccccgcggta acaccctcca ccttcacttt atgccttgca     4320
cttactgttt cctctgccca ggggttcttt gctccgtctc tactgtttca atactgccc      4380
aacctcaaag cccagctcca agctacctc ctctgtgaag aactccttgg aaatgatcat      4440
ctcagactcc tctattggct gtcccagcac aagtgatcac gtttaacttc tgaaggcctg      4500
gacagaatct tgagtgggtc cgccattcca ttccaagtcg ccctcaccg tgcacttcct      4560
cttctcccgc cagattcttc aaagtgacgc ctcccccagg aagcgggccc cagaaccagt     4620
acgggaacgt gctgtctctc cccacaccca cctcaggcct cggtaagagg caccgcccct    4680
ccagcctata gctccgcccc agatccgggg ctccaccccc actctcctca tccctccaat    4740
ccgctgtgcg ccaagccttc tggagctcgg aactccgccc ccggggcggg gagtccgcc    4800
cagctatgag cccgcctct agaaccgac cccgcctcca gggctcagag ccacgccccc     4860
aggacccaga gcctgaagtc gtaatcaaga gcagaacttc gccccagaac tgaaggcctc    4920
```

```
ggccctagat ttagattccg ccccagggtt caaggccggg ttcctagacc cagagtccat    4980
tcgcagagcc caaaacatcc tcttcccgtg ccccgccgcg cggaccctta gccttgaccg    5040 ccccatctc ttctgacccc gtcttacaat gccctctca ccaggacgcg cccagcgttg      5100
ggccgcaggc ctgggggca ctgccccgtc ttatggaaac ccgagcagcg acgtccaggc     5160
ggatggagcc ttggggtccc ggagcccgcc gggagtgggt gaatgactgg gagagggaag    5220
ggtcgttccc cacatggagg gggttggagc ggtctgtggc ccgaatagtg gactgggccc    5280
tggaggagag ggggcatgac tcggttcccc atccccatcc ccaaaccccc aggcccagaa    5340
gaagaggaag gggagggcta tgaggaacct gacagtgagg aggactccga gttctatgag    5400
aacgactcca accttgggca ggaccagctc tcccagggta aggctgccct ccccgtggc    5460 ccccacctc tgcggtggcc tgtggactcc catggacacc cctccttctc caccagatgg    5520
cagcggctac gagaaccctg aggatgagcc cctgggtcct gaggatgaag actccttctc    5580
caacggtaac ttggggcctt tgtgggacct cagagactta ggtgtaattg cagcgctgtg    5640
acactcctag aaggggtccc tggagttctc tctcttctgc cacagctgag tcttatgaga    5700
acgaggatga gagctgacc cagccggtcg ccaggacaat gggtgtgtgt gaggatggca    5760
acagtccagg ggggaggcgg aggacacctg gaggccagga ggaatagtaa cctccctctt    5820 cccttttccag acttcctgag ccctcatggg tcagcctggg accccagccg gaagcaacc    5880 tccctgggtg agagatgctt tcaatcagac tgccttgccc agcttgggtg acctggcctc    5940
agctctgaca ccagatccaa ctttgacctg accctgaccc caaacccgaa cccaatcctg    6000
tgactcctct cacctcaaca ctgagcccca tcccccatcc tgagcccat ccccatcct     6060 gacccccaat atttaccccc tccctaactg tgaatatcaa caccgatccc aatgcagtat    6120
cagcctggac ttgatctcca cctcacctca gccccagtgc agacctcaac ttggaccca    6180 gcttactctg cagcttcttc atgactctga ctccgactcc ctccagtttc ttctttttct    6240
ttttcttttt tttgagacgg agtctccctc tgttgcccag gctggagtgc agttgccacc    6300
tctgcctcct aggttcaagc gattctcatg cctcagcctc ctgagtagct gggattatag    6360
acgtttgcca ccacacctgg ctaattttg tattttcagt agagacaggg tttcgccatg     6420
ttggccagac tggtctccaa ctcctggcct ctagtgatct gcccgccttg gcttcccaaa    6480
gtgctgggat tacaggcatg agccaccacg cccagcccag ttctgttctt gaccccttcc   6540
ttagccataa tctaacccat atctaaccct gaccctacag ctaactgggg ccccaaactc    6600
aatgctaacc aaatcacccc ttcccagcac agcatgggta atgctcctca ccttcctctg    6660 ccctcagtc ttcctcctta ccgtaggctg tacttcccat gccctagcct ccaattctcc     6720 atccccgcc caagcagggt cccagtccta tgaggatatg agaggaatcc tgtatgcagc    6780
cccccagctc cgctccattc ggggccagcc tggacccaat catgaggaag gtgggtgctt    6840
ctgccgctgt cccctgctgt ccctgggct gactttgcct tccagcctac ttccagtgcc     6900
acccatgttc tcctcctccc tggtcctatc cagatgcaga ctcttatgag aacatggata    6960
atcccgatgg gccagaccca gcctggggag gaggggccg catgggcacc tggagcacca    7020
ggtgatcctc aggtggccag gtgagctggg actgcccta gggaaagcgg ggaggggagg    7080
agataggcac ggatggcagt ggctgctggc tttcagggag ggagagggaa cagggttcct    7140
agggcctggt gggcagggg aggactgctg gaccctccc catcaccgtt tcttctgcat     7200
agcctggatc tcctcaagtc cccaagattc acacctgact ctgaaatctg aagacctcga    7260
```

```
gcagatgatg ccaacctctg gagcaatgtt gcttaggatg tgtgcatgtg tgtaagtgtg    7320
tgtgtgtgtg tgtgtgtgta tacatgccag tgacacttcc agtccccttt gtattcctta    7380
aataaactca atgagctctt ccaatccta                                       7409
```

<210> SEQ ID NO 8
<211> LENGTH: 557
<212> TYPE: PRT
<213> ORGANISM: Homo sapiens

<400> SEQUENCE: 8

```
Met Pro Pro Pro Arg Leu Leu Phe Phe Leu Leu Phe Leu Thr Pro Met
1               5                   10                  15

Glu Val Arg Pro Glu Glu Pro Leu Val Val Lys Val Glu Glu Gly Asp
            20                  25                  30

Asn Ala Val Leu Gln Cys Leu Lys Gly Thr Ser Asp Gly Pro Thr Gln
        35                  40                  45

Gln Leu Thr Trp Ser Arg Glu Ser Pro Leu Lys Pro Phe Leu Lys Leu
    50                  55                  60

Ser Leu Gly Leu Pro Gly Leu Gly Ile His Met Arg Pro Leu Ala Ile
65                  70                  75                  80

Trp Leu Phe Ile Phe Asn Val Ser Gln Gln Met Gly Gly Phe Tyr Leu
                85                  90                  95

Cys Gln Pro Gly Pro Pro Ser Glu Lys Ala Trp Gln Pro Gly Trp Thr
            100                 105                 110

Val Asn Val Glu Gly Ser Gly Glu Leu Phe Arg Trp Asn Val Ser Asp
        115                 120                 125

Leu Gly Gly Leu Gly Cys Gly Leu Lys Asn Arg Ser Ser Glu Gly Pro
    130                 135                 140

Ser Ser Pro Ser Gly Lys Leu Met Ser Pro Lys Leu Tyr Val Trp Ala
145                 150                 155                 160

Lys Asp Arg Pro Glu Ile Trp Glu Gly Glu Pro Pro Cys Leu Pro Pro
                165                 170                 175

Arg Asp Ser Leu Asn Gln Ser Leu Ser Gln Asp Leu Thr Met Ala Pro
            180                 185                 190

Gly Ser Thr Leu Trp Leu Ser Cys Gly Val Pro Pro Asp Ser Val Ser
        195                 200                 205

Arg Gly Pro Leu Ser Trp Thr His Val His Pro Lys Gly Pro Lys Ser
    210                 215                 220

Leu Leu Ser Leu Glu Leu Lys Asp Asp Arg Pro Ala Arg Asp Met Trp
225                 230                 235                 240

Val Met Glu Thr Gly Leu Leu Leu Pro Arg Ala Thr Ala Gln Asp Ala
                245                 250                 255

Gly Lys Tyr Tyr Cys His Arg Gly Asn Leu Thr Met Ser Phe His Leu
            260                 265                 270

Glu Ile Thr Ala Arg Pro Val Leu Trp His Trp Leu Leu Arg Thr Gly
        275                 280                 285

Gly Trp Lys Val Ser Ala Val Thr Leu Ala Tyr Leu Ile Phe Cys Leu
    290                 295                 300

Cys Ser Leu Val Gly Ile Leu His Leu Gln Arg Ala Leu Val Leu Arg
305                 310                 315                 320

Arg Lys Arg Lys Arg Met Thr Asp Pro Thr Arg Arg Phe Phe Lys Val
                325                 330                 335

Thr Pro Pro Pro Gly Ser Gly Pro Gln Asn Gln Tyr Gly Asn Val Leu
            340                 345                 350
```

```
Ser Leu Pro Thr Pro Thr Ser Gly Leu Gly Arg Ala Gln Arg Trp Ala
        355                 360                 365
Ala Gly Leu Gly Gly Thr Ala Pro Ser Tyr Gly Asn Pro Ser Ser Asp
    370                 375                 380
Val Gln Ala Asp Gly Ala Leu Gly Ser Arg Ser Pro Pro Gly Val Gly
385                 390                 395                 400
Pro Glu Glu Glu Gly Glu Gly Tyr Glu Glu Pro Asp Ser Glu Glu
                405                 410                 415
Asp Ser Glu Phe Tyr Glu Asn Asp Ser Asn Leu Gly Gln Asp Gln Leu
                420                 425                 430
Ser Gln Asp Gly Ser Gly Tyr Glu Asn Pro Glu Asp Glu Pro Leu Gly
        435                 440                 445
Pro Glu Asp Glu Asp Ser Phe Ser Asn Ala Glu Ser Tyr Glu Asn Glu
    450                 455                 460
Asp Glu Glu Leu Thr Gln Pro Val Ala Arg Thr Met Asp Phe Leu Ser
465                 470                 475                 480
Pro His Gly Ser Ala Trp Asp Pro Ser Arg Glu Ala Thr Ser Leu Ala
                485                 490                 495
Gly Ser Gln Ser Tyr Glu Asp Met Arg Gly Ile Leu Tyr Ala Ala Pro
            500                 505                 510
Gln Leu Arg Ser Ile Arg Gly Gln Pro Gly Pro Asn His Glu Glu Asp
        515                 520                 525
Ala Asp Ser Tyr Glu Asn Met Asp Asn Pro Asp Gly Pro Asp Pro Ala
    530                 535                 540
Trp Gly Gly Gly Gly Arg Met Gly Thr Trp Ser Thr Arg
545                 550                 555

<210> SEQ ID NO 9
<211> LENGTH: 3594
<212> TYPE: DNA
<213> ORGANISM: Homo sapiens

<400> SEQUENCE: 9
gtctatcagc gatttcatct tcaggcctgg actacaccac tcaccctccc agtgtgcttg      60
agaaacaaac tgcacccact gaactccgca gctagcatcc aaatcagccc ttgagatttg     120
aggccttgga gactcagatc ctgaacaaga gagaacaaaa tctctacttt gatgaacttc     180
ccattctgtg gggaagagac tgacaataag caattaaata aataagaact cagcagtagg     240
ccttgcctca gatccaaggt cactcggaag aggccatgtc taccctcaat gacactcatg     300
gaggaaatgc tgagagaagc attcagatgc atgacacaag gtaagactgc caaaaatctt     360
gttcttgctc tcctcatttt gttatttgtt ttatttttag gagttttgag agcaaaatga     420
caacacccag aaattcagta atgggacttt cccggcagag ccaatgaaag gccctattg      480
ctatgcaatc tggtccaaaa ccactcttca ggaggatgtc ttcactggtg gccccacgc      540
aaagcttctt catgagggaa tctaagactt tgggggctgt ccagattatg aatgggctct     600
tccacattgc cctgggggt cttctgatga tcccagcagg gatctatgca cccatctgtg      660
tgactgtgtg gtaccctctc tggggaggca ttatgtatat tatttccgga tcactcctgg     720
cagcaacgga gaaaaactcc aggaagtgtt tggtcaaagg aaaaatgata atgaattcat     780
tgagcctctt tgctgccatt tctggaatga ttctttcaat catggacata cttaatatta     840
aaatttccca ttttttaaaa atggagagtc tgaattttat tagagctcac acaccatata     900
ttaacatata caactgtgaa ccagctaatc cctctgagaa aaactcccca tctacccaat     960
```

```
actgttacag catacaatct ctgttcttgg gcattttgtc agtgatgctg atctttgcct    1020
tcttccagga acttgtaata gctggcatcg ttgagaatga atggaaaaga acgtgctcca    1080
gacccaaatc taacatagtt ctcctgtcag cagaagaaaa aaaagaacag actattgaaa    1140
taaaagaaga agtggttggg ctaactgaaa catcttccca accaaagaat gaagaagaca    1200
ttgaaattat tccaatccaa gaagaggaag aagaagaaac agagacgaac tttccagaac    1260
ctccccaaga tcaggaatcc tcaccaatag aaaatgacag ctctccttaa gtgatttctt    1320
ctgttttctg tttccttttt taaacattag tgttcatagc ttccaagaga catgctgact    1380
ttcatttctt gaggtactct gcacatacgc accacatctc tatctggcct ttgcatggag    1440
tgaccatagc tccttctctc ttacattgaa tgtagagaat gtagccattg tagcagcttg    1500
tgttgtcacg cttcttcttt tgagcaactt tcttacactg aagaaaggca gaatgagtgc    1560
ttcagaatgt gatttcctac taacctgttc cttggatagg cttttagta tagtatttt    1620 ttttgtcatt ttctccatca acaaccaggg agactgcacc tgatggaaaa gatatatgac    1680
tgcttcatga cattcctaaa ctatctttt tttattccac atctacgttt tggtggagt     1740 ccctttttgca tcattgtttt aaggatgata aaaaaaaata caactaggg acaatacaga    1800 acccattcca tttatctttc tacagggctg acattgtggc acattcttag agttaccaca    1860
ccccatgagg gaagctctaa atagccaaca cccatctgtt ttttgtaaaa acagcatagc    1920
ttatacatgg acatgtctct gccttaactt ttcctaactc ccactctagg ctattgtttg    1980
catgtctacc tacttttagc cattatgcga gaaaagaaaa aaatgaccat agaaaatgcc    2040
accatgaggt gcccaaattt caaataataa ttaacattta gttatattta aatttccag    2100 atgacaaagt atttcatcaa ataacttcat ttgatgttcc atgatcaaga aagaatccct    2160
atctctattt tacaagtaat tcaaagaggc caaataactt gtaaacaaga aaaggtaact    2220
tgtcaacagt cataactagt aattatgaga gccttgtttc ataaccaggt cttcttactc    2280
aaatcctgtg atgtttgaaa taaccaaatt gtctctccaa tgtctgcata aactgtgaga    2340
gccaagtcaa cagcttttat caagaattta ctctctgacc agcaataaac aagcactgag    2400
agacacagag agccagattc agattttacc catggggata aaaagactca gactttcacc    2460
acatttggaa aactcttgc atcataaata tataataact ggtagtttat atgaagcaga    2520
cactaagtgc tatagacact ctcagaatat catacttgga acaatgtaa ttaaaatgcc     2580 gaatctgagt caacagctgc cctacttttc aattcagata tactagtacc ttacctagaa    2640
ataatgttaa cctagggtga agtcactata atctgtagtc tattatttgg gcatttgcta    2700
catgatgagt gctgccagat tgtggcaggt aaagagacaa tgtaatttgc actccctatg    2760
atatttctac attttagcg accactagtg aagacattc cccaaaatta gaaaaaagg      2820 agatagaaga tttctgtcta tgtaaagttc tcaaatttg ttctaaatta ataaaactat     2880
ctttgtgttc ttttctgcaa cagatgattc caacatgggt gtttgtctat tcttctttac    2940
tcttgaaaca ttagaccatg ggaggctctt acagccttga gttgatattt atacaaccca    3000
aatctaggtt tgaacggtga ggtgtcaggt catcaaatat tcatgtctat atagtcttac    3060
acaggttctc aaaaaaaatg ttcatgggat aggtcattga taatgattc cttattctga     3120 gaactccaga cgactgaaat atatgagaga aggaaaagga catagtagga gcaggcctga    3180
gaaaaaaatg aaagtcagaa atcttttaaa aaatacaaga tcttatttct atcttatttt    3240
ttctcctctt ctgaaatata tatgaggatt cctctccaaa cccatggttt ctctaagaat    3300
```

| | | | | | | |
|---|---|---|---|---|---|---|
| tttgagtcat | ttgtatgacc | tcaaataatt | agttttagct | gacctcacat | aactccttat | 3360 |
| aataggagac | atctttaatg | tctgctatta | agaaggatg | aaaattccta | tgaccttctc | 3420 |
| cccgattatc | cctttggcaa | tatagagtca | ataataaca | ttgaccaata | gtaaacatgc | 3480 |
| tttgccaaga | agtagaagat | atattctcta | gccttagttt | ttcctcccaa | tttgcatttt | 3540 |
| tgtaaaaata | atgttgtatc | cacaaaggaa | ataaacttta | aaaacccaag | tgca | 3594 |

<210> SEQ ID NO 10
<211> LENGTH: 297
<212> TYPE: PRT
<213> ORGANISM: Homo sapiens

<400> SEQUENCE: 10

Met Thr Thr Pro Arg Asn Ser Val Asn Gly Thr Phe Pro Ala Glu Pro
1               5                   10                  15

Met Lys Gly Pro Ile Ala Met Gln Ser Gly Pro Lys Pro Leu Phe Arg
            20                  25                  30

Arg Met Ser Ser Leu Val Gly Pro Thr Gln Ser Phe Phe Met Arg Glu
        35                  40                  45

Ser Lys Thr Leu Gly Ala Val Gln Ile Met Asn Gly Leu Phe His Ile
    50                  55                  60

Ala Leu Gly Gly Leu Leu Met Ile Pro Ala Gly Ile Tyr Ala Pro Ile
65                  70                  75                  80

Cys Val Thr Val Trp Tyr Pro Leu Trp Gly Gly Ile Met Tyr Ile Ile
                85                  90                  95

Ser Gly Ser Leu Leu Ala Ala Thr Glu Lys Asn Ser Arg Lys Cys Leu
            100                 105                 110

Val Lys Gly Lys Met Ile Met Asn Ser Leu Ser Leu Phe Ala Ala Ile
        115                 120                 125

Ser Gly Met Ile Leu Ser Ile Met Asp Ile Leu Asn Ile Lys Ile Ser
    130                 135                 140

His Phe Leu Lys Met Glu Ser Leu Asn Phe Ile Arg Ala His Thr Pro
145                 150                 155                 160

Tyr Ile Asn Ile Tyr Asn Cys Glu Pro Ala Asn Pro Ser Glu Lys Asn
                165                 170                 175

Ser Pro Ser Thr Gln Tyr Cys Tyr Ser Ile Gln Ser Leu Phe Leu Gly
            180                 185                 190

Ile Leu Ser Val Met Leu Ile Phe Ala Phe Phe Gln Glu Leu Val Ile
        195                 200                 205

Ala Gly Ile Val Glu Asn Glu Trp Lys Arg Thr Cys Ser Arg Pro Lys
    210                 215                 220

Ser Asn Ile Val Leu Leu Ser Ala Glu Glu Lys Lys Glu Gln Thr Ile
225                 230                 235                 240

Glu Ile Lys Glu Glu Val Val Gly Leu Thr Glu Thr Ser Ser Gln Pro
                245                 250                 255

Lys Asn Glu Glu Asp Ile Glu Ile Ile Pro Ile Gln Glu Glu Glu Glu
            260                 265                 270

Glu Glu Thr Glu Thr Asn Phe Pro Glu Pro Pro Gln Asp Gln Glu Ser
        275                 280                 285

Ser Pro Ile Glu Asn Asp Ser Ser Pro
    290                 295

<210> SEQ ID NO 11
<211> LENGTH: 3300
<212> TYPE: DNA

<213> ORGANISM: Homo sapiens

<400> SEQUENCE: 11

| | | | | | |
|---|---|---|---|---|---|
| acttctccttt | ttgctctcag | atgctgccag | ggtccctgaa | gagggaagac | acgcggaaac | 60 |
| aggcttgcac | ccagacacga | caccatgcat | ctcctcggcc | cctggctcct | gctcctggtt | 120 |
| ctagaatact | tggctttctc | tgactcaagt | aaatgggttt | ttgagcaccc | tgaaaccctc | 180 |
| tacgcctggg | aggggggcctg | cgtctggatc | ccctgcacct | acagagccct | agatggtgac | 240 |
| ctggaaagct | tcatcctgtt | ccacaatcct | gagtataaca | agaacacctc | gaagtttgat | 300 |
| gggacaagac | tctatgaaag | cacaaaggat | gggaaggttc | cttctgagca | gaaaaggggtg | 360 |
| caattcctgg | gagacaagaa | taagaactgc | acactgagta | tccacccggt | gcacctcaat | 420 |
| gacagtggtc | agctggggct | gaggatggag | tccaagactg | agaaatggat | ggaacgaata | 480 |
| cacctcaatg | tctctgaaag | gccttttcca | cctcatatcc | agctccctcc | agaaattcaa | 540 |
| gagtcccagg | aagtcactct | gacctgcttg | ctgaatttct | cctgctatgg | gtatccgatc | 600 |
| caattgcagt | ggctcctaga | ggggggttcca | atgaggcagg | ctgctgtcac | ctcgacctcc | 660 |
| ttgaccatca | agtctgtctt | cacccggagc | gagctcaagt | ctcccccaca | gtggagtcac | 720 |
| catgggaaga | ttgtgacctg | ccagcttcag | gatgcagatg | ggaagttcct | ctccaatgac | 780 |
| acggtgcagc | tgaacgtgaa | gcacacccccg | aagttggaga | tcaaggtcac | tcccagtgat | 840 |
| gccatagtga | gggaggggga | ctctgtgacc | atgacctgcg | aggtcagcag | cagcaacccg | 900 |
| gagtacacga | cggtatcctg | gctcaaggat | gggacctcgc | tgaagaagca | gaatacattc | 960 |
| acgctaaacc | tgcgcgaagt | gaccaaggac | cagagtggga | agtactgctg | tcaggtctcc | 1020 |
| aatgacgtgg | gcccgggaag | gtcggaagaa | gtgttcctgc | aagtgcagta | tgccccggaa | 1080 |
| ccttccacgg | ttcagatcct | ccactcaccg | gctgtgagg | gaagtcaagt | cgagtttctt | 1140 |
| tgcatgtcac | tggccaatcc | tcttccaaca | aattacacgt | ggtaccacaa | tgggaaagaa | 1200 |
| atgcagggaa | ggacagagga | gaaagtccac | atcccaaaga | tcctccccctg | gcacgctggg | 1260 |
| acttattcct | gtgtggcaga | aaacattctt | ggtactggac | agaggggccc | gggagctgag | 1320 |
| ctggatgtcc | agtatcctcc | caagaaggtg | accacagtga | ttcaaaaccc | catgccgatt | 1380 |
| cgagaaggag | acacagtgac | cctttcctgt | aactacaatt | ccagtaaccc | cagtgttacc | 1440 |
| cggtatgaat | ggaaaccccca | tggcgcctgg | gaggagccat | cgcttggggt | gctgaagatc | 1500 |
| caaaacgttg | gctgggacaa | cacaaccatc | gcctgcgcag | cttgtaatag | ttggtgctcg | 1560 |
| tgggcctccc | ctgtcgccct | gaatgtccag | tatgcccccc | gagacgtgag | ggtccggaaa | 1620 |
| atcaagcccc | tttccgagat | tcactctgga | aactcggtca | gcctccaatg | tgacttctca | 1680 |
| agcagccacc | ccaaagaagt | ccagttcttc | tgggagaaaa | atggcaggct | tctgggaaa | 1740 |
| gaaagccagc | tgaattttga | ctccatctcc | ccagaagatg | ctgggagtta | cagctgctgg | 1800 |
| gtgaacaact | ccataggaca | gacagcgtcc | aaggcctgga | cacttgaagt | gctgtatgca | 1860 |
| cccaggaggc | tgcgtgtgtc | catgagcccg | ggggaccaag | tgatgagggg | gaagagtgca | 1920 |
| accctgacct | gtgagagcga | cgccaaccct | cccgtctccc | actacacctg | gtttgactgg | 1980 |
| aataaccaaa | gcctccccta | ccacagccag | aagctgagat | ggagccggt | gaaggtccag | 2040 |
| cactcgggtg | cctactggtg | ccaggggacc | aacagtgtgg | gcaagggccg | ttcgcctctc | 2100 |
| agcacccctca | ccgtctacta | tagcccggag | accatcggca | ggcgagtggc | tgtgggactc | 2160 |
| gggtcctgcc | tcgccatcct | catcctggca | atctgtgggc | tcaagctcca | gcgacgttgg | 2220 |
| aagaggacac | agagccagca | ggggcttcag | gagaattcca | gcggccagag | cttctttgtg | 2280 |

```
aggaataaaa aaggttagaag ggccccctc tctgaaggcc cccactccct gggatgctac    2340
aatccaatga tggaagatgg cattagctac accaccctgc gctttcccga gatgaacata    2400
ccacgaactg gagatgcaga gtcctcagag atgcagagac ctcccccgga ctgcgatgac    2460
acggtcactt attcagcatt gcacaagcgc caagtgggcg actatgagaa cgtcattcca    2520
gattttccag aagatgaggg gattcattac tcagagctga tccagtttgg ggtcggggag    2580
cggcctcagg cacaagaaaa tgtggactat gtgatcctca acattgaca ctggatgggc    2640 tgcagcagag gcactggggg cagcgggggc cagggaagtc cccgagtttc cccagacacc    2700
gccacatggc ttcctcctgc gcgcatgtgc gcacacacac acacacacgc acacacacac    2760
acacacactc actgcggaga accttgtgcc tggctcagag ccagtctttt tggtgagggt    2820
aaccccaaac ctccaaaact cctgcccctg ttctcttcca ctctccttgc tacccagaaa    2880
tccatctaaa tacctgccct gacatgcaca cctcccctg ccccaccac ggccactggc    2940 catctccacc cccagctgct tgtgtccctc ctgggatctg ctcgtcatca ttttccttc    3000 ccttctccat ctctctggcc ctctacccct gatctgacat ccccactcac gaatattatg    3060
cccagtttct gcctctgagg gaaagcccag aaaaggacag aaacgaagta gaaaggggcc    3120
cagtcctggc ctggcttctc ctttggaagt gaggcattgc acggggagac gtacgtatca    3180 gcggccctt gactctgggg actccgggtt tgagatggac acactggtgt ggattaacct    3240
gccagggaga cagagctcac aataaaaatg gctcagatgc cacttcaaag aaaaaaaaaa    3300
```

<210> SEQ ID NO 12
<211> LENGTH: 847
<212> TYPE: PRT
<213> ORGANISM: Homo sapiens

<400> SEQUENCE: 12

```
Met His Leu Leu Gly Pro Trp Leu Leu Leu Val Leu Glu Tyr Leu
1               5                   10                  15

Ala Phe Ser Asp Ser Ser Lys Trp Val Phe Glu His Pro Glu Thr Leu
                20                  25                  30

Tyr Ala Trp Glu Gly Ala Cys Val Trp Ile Pro Cys Thr Tyr Arg Ala
            35                  40                  45

Leu Asp Gly Asp Leu Glu Ser Phe Ile Leu Phe His Asn Pro Glu Tyr
        50                  55                  60

Asn Lys Asn Thr Ser Lys Phe Asp Gly Thr Arg Leu Tyr Glu Ser Thr
65                  70                  75                  80

Lys Asp Gly Lys Val Pro Ser Glu Gln Lys Arg Val Gln Phe Leu Gly
                85                  90                  95

Asp Lys Asn Lys Asn Cys Thr Leu Ser Ile His Pro Val His Leu Asn
            100                 105                 110

Asp Ser Gly Gln Leu Gly Leu Arg Met Glu Ser Lys Thr Glu Lys Trp
        115                 120                 125

Met Glu Arg Ile His Leu Asn Val Ser Glu Arg Pro Phe Pro Pro His
    130                 135                 140

Ile Gln Leu Pro Pro Glu Ile Gln Glu Ser Gln Glu Val Thr Leu Thr
145                 150                 155                 160

Cys Leu Leu Asn Phe Ser Cys Tyr Gly Tyr Pro Ile Gln Leu Gln Trp
                165                 170                 175

Leu Leu Glu Gly Val Pro Met Arg Gln Ala Ala Val Thr Ser Thr Ser
            180                 185                 190
```

```
Leu Thr Ile Lys Ser Val Phe Thr Arg Ser Glu Leu Lys Phe Ser Pro
            195                 200                 205

Gln Trp Ser His His Gly Lys Ile Val Thr Cys Gln Leu Gln Asp Ala
210                 215                 220

Asp Gly Lys Phe Leu Ser Asn Asp Thr Val Gln Leu Asn Val Lys His
225                 230                 235                 240

Thr Pro Lys Leu Glu Ile Lys Val Thr Pro Ser Asp Ala Ile Val Arg
                245                 250                 255

Glu Gly Asp Ser Val Thr Met Thr Cys Glu Val Ser Ser Asn Pro
            260                 265                 270

Glu Tyr Thr Thr Val Ser Trp Leu Lys Asp Gly Thr Ser Leu Lys Lys
            275                 280                 285

Gln Asn Thr Phe Thr Leu Asn Leu Arg Glu Val Thr Lys Asp Gln Ser
290                 295                 300

Gly Lys Tyr Cys Cys Gln Val Ser Asn Asp Val Gly Pro Gly Arg Ser
305                 310                 315                 320

Glu Glu Val Phe Leu Gln Val Gln Tyr Ala Pro Glu Pro Ser Thr Val
                325                 330                 335

Gln Ile Leu His Ser Pro Ala Val Glu Gly Ser Gln Val Glu Phe Leu
                340                 345                 350

Cys Met Ser Leu Ala Asn Pro Leu Pro Thr Asn Tyr Thr Trp Tyr His
            355                 360                 365

Asn Gly Lys Glu Met Gln Gly Arg Thr Glu Glu Lys Val His Ile Pro
370                 375                 380

Lys Ile Leu Pro Trp His Ala Gly Thr Tyr Ser Cys Val Ala Glu Asn
385                 390                 395                 400

Ile Leu Gly Thr Gly Gln Arg Gly Pro Gly Ala Glu Leu Asp Val Gln
                405                 410                 415

Tyr Pro Pro Lys Lys Val Thr Thr Val Ile Gln Asn Pro Met Pro Ile
                420                 425                 430

Arg Glu Gly Asp Thr Val Thr Leu Ser Cys Asn Tyr Asn Ser Ser Asn
            435                 440                 445

Pro Ser Val Thr Arg Tyr Glu Trp Lys Pro His Gly Ala Trp Glu Glu
450                 455                 460

Pro Ser Leu Gly Val Leu Lys Ile Gln Asn Val Gly Trp Asp Asn Thr
465                 470                 475                 480

Thr Ile Ala Cys Ala Ala Cys Asn Ser Trp Cys Ser Trp Ala Ser Pro
                485                 490                 495

Val Ala Leu Asn Val Gln Tyr Ala Pro Arg Asp Val Arg Val Arg Lys
                500                 505                 510

Ile Lys Pro Leu Ser Glu Ile His Ser Gly Asn Ser Val Ser Leu Gln
515                 520                 525

Cys Asp Phe Ser Ser Ser His Pro Lys Glu Val Gln Phe Phe Trp Glu
530                 535                 540

Lys Asn Gly Arg Leu Leu Gly Lys Glu Ser Gln Leu Asn Phe Asp Ser
545                 550                 555                 560

Ile Ser Pro Glu Asp Ala Gly Ser Tyr Ser Cys Trp Val Asn Asn Ser
                565                 570                 575

Ile Gly Gln Thr Ala Ser Lys Ala Trp Thr Leu Glu Val Leu Tyr Ala
                580                 585                 590

Pro Arg Arg Leu Arg Val Ser Met Ser Pro Gly Asp Gln Val Met Glu
            595                 600                 605

Gly Lys Ser Ala Thr Leu Thr Cys Glu Ser Asp Ala Asn Pro Pro Val
```

```
                    610                615                620
Ser His Tyr Thr Trp Phe Asp Trp Asn Asn Gln Ser Leu Pro Tyr His
625                     630                635                640

Ser Gln Lys Leu Arg Leu Glu Pro Val Lys Val Gln His Ser Gly Ala
                    645                650                655

Tyr Trp Cys Gln Gly Thr Asn Ser Val Gly Lys Gly Arg Ser Pro Leu
                    660                665                670

Ser Thr Leu Thr Val Tyr Tyr Ser Pro Glu Thr Ile Gly Arg Arg Val
                    675                680                685

Ala Val Gly Leu Gly Ser Cys Leu Ala Ile Leu Ile Leu Ala Ile Cys
690                     695                700

Gly Leu Lys Leu Gln Arg Arg Trp Lys Arg Thr Gln Ser Gln Gln Gly
705                     710                715                720

Leu Gln Glu Asn Ser Ser Gly Gln Ser Phe Phe Val Arg Asn Lys Lys
                    725                730                735

Val Arg Arg Ala Pro Leu Ser Glu Gly Pro His Ser Leu Gly Cys Tyr
                    740                745                750

Asn Pro Met Met Glu Asp Gly Ile Ser Tyr Thr Thr Leu Arg Phe Pro
                    755                760                765

Glu Met Asn Ile Pro Arg Thr Gly Asp Ala Glu Ser Ser Glu Met Gln
770                     775                780

Arg Pro Pro Pro Asp Cys Asp Asp Thr Val Thr Tyr Ser Ala Leu His
785                     790                795                800

Lys Arg Gln Val Gly Asp Tyr Glu Asn Val Ile Pro Asp Phe Pro Glu
                    805                810                815

Asp Glu Gly Ile His Tyr Ser Glu Leu Ile Gln Phe Gly Val Gly Glu
                    820                825                830

Arg Pro Gln Ala Gln Glu Asn Val Asp Tyr Val Ile Leu Lys His
                    835                840                845

<210> SEQ ID NO 13
<211> LENGTH: 1413
<212> TYPE: DNA
<213> ORGANISM: Mus musculus

<400> SEQUENCE: 13
atggctgtcc tggtgctgtt cctctgcctg gttgcatttc caagctgtgt cctgtcccag    60
gtgcagctga aggagtcagg acctggcctg gtggcgccct cacagagcct gtccatcact   120
tgtactgtct ctggattttc attaaccaac tatggtgtac actgggttcg ccagcctcca   180
ggaaaaggtc tggagtggct gggaatgatt tgggctggtg aagcacaaa ttataattcg    240 gctctcatgt ccagactgaa catcaacaaa gacaactcca agagccaagt tttcttagaa   300
atgaacagtc tgcaaactga tgacactgcc ttgtacttct gtgccagaga agccacctcg   360
ggctacgtag actatgctgt ggactactgg ggtcaaggaa cgtcagtcac cgtctcctca   420
gccaaaacaa cagccccatc ggtctatcca ctggcccctg tgtgtggaga tacaactggc   480
tcctcggtga ctctaggatg cctggtcaag ggttatttcc ctgagccagt gaccttgacc   540
tggaactctg gatccctgtc cagtggtgtg cacaccttcc cagctgtcct gcagtctgac   600
ctctacaccc tcagcagctc agtgactgta acctcgagca cctggcccag ccagtccatc   660
acctgcaatg tggcccaccc ggcaagcagc accaaggtgg acaagaaaat tgagcccaga   720
gggcccacaa tcaagccctg tcctccatgc aaatgcccag cacctaacct cttgggtgga   780
ccatccgtct tcatcttccc tccaaagatc aaggatgtac tcatgatctc cctgagcccc   840
```

```
atagtcacat gtgtggtggt ggatgtgagc gaggatgacc cagatgtcca gatcagctgg    900
tttgtgaaca acgtggaagt acacacagct cagacacaaa cccatagaga ggattacaac    960
agtactctcc gggtggtcag tgccctcccc atccagcacc aggactggat gagtggcaag   1020
gagttcaaat gcaaggtcaa caacaaagac ctcccagcgc ccatcgagag aaccatctca   1080
aaacccaaag ggtcagtaag agctccacag gtatatgtct tgcctccacc agaagaagag   1140
atgactaaga aacaggtcac tctgacctgc atggtcacag acttcatgcc tgaagacatt   1200
tacgtggagt ggaccaacaa cgggaaaaca gagctaaact acaagaacac tgaaccagtc   1260
ctggactctg atggttctta cttcatgtac agcaagctga gagtgaaaaa gaagaactgg   1320
gtggaaagaa atagctactc ctgttcagtg gtccacgagg gtctgcacaa tcaccacacg   1380
actaagagct ctcccggac tccgggtaaa tga                                  1413

<210> SEQ ID NO 14
<211> LENGTH: 708
<212> TYPE: DNA
<213> ORGANISM: Mus musculus

<400> SEQUENCE: 14
atggattttc aagtgcagat tttcagcttc ctgctaatca gtgcctcagt cataatatcc     60
agaggacaaa ttattctcaa ccagtctcca gcaatcatgt ctgcatttcc aggggagaag    120
gtcaccatga cctgcagtgc cagctcaagt gtaagttaca tgcactggta ccagcagaag    180
tcaggcacct cccccaaaag atggatttat gacacatcca aattggcttc tggagtccct    240
gctcgcttca gtggcagtgg gtctgggacc tcttattctc tcacaatcag cagcatggag    300
gctgaagatg ctgccactta ttactgccag cagtggagta gtagcccgct cacgttcggt    360
gctgggacca agctggagct gaaacgggct gatgctgcac caactgtatc catcttccca    420
ccatccagtg agcagttaac atctggaggt gcctcagtcg tgtgcttctt gaacaacttc    480
taccccaaag acatcaatgt caagtggaag attgatggca gtgaacgaca aaatggcgtc    540
ctgaacagtt ggactgatca ggacagcaaa gacagcacct acagcatgag cagcaccctc    600
acgttgacca aggacgagta tgaacgacat aacagctata cctgtgaggc cactcacaag    660
acatcaactt cacccattgt caagagcttc aacaggaatg agtgttag                 708

<210> SEQ ID NO 15
<211> LENGTH: 1422
<212> TYPE: DNA
<213> ORGANISM: Mus musculus

<400> SEQUENCE: 15
atggctgtcc tggtgctgtt cctctgcctg gttgcatttc caagctgtgt cctgtcccag     60
gtgcagctgc agcagtctgg ggctgagctg gtgaggcctg gtcctcagt gaagatttcc    120 tgcaaggctt ctggctatgc attcagtagc tactggatga actgggtgaa gcagaggcct   180
ggacagggtc ttgagtggat tggacagatt tggcctggag atggtgatac taactacaat   240
ggaaagttca gggtaaagc cactctgact gcagacgaat cctccagcac agcctacatg   300
caactcagca gcctagcatc tgaggactct gcggtctatt tctgtgcaag acgggagact   360
acgacggtag gccgttatta ctatgctatg gactactggg gtcaaggaac ctcagtcacc   420
gtctcctcag ccaaaacaac agccccatcg gtctatccac tggcccctgt gtgtggagat   480
acaactggct cctcggtgac tctaggatgc ctggtcaagg gttatttccc tgagccagtg    540
```

```
accttgacct ggaactctgg atccctgtcc agtggtgtgc acaccttccc agctgtcctg      600
cagtctgacc tctacaccct cagcagctca gtgactgtaa cctcgagcac ctggcccagc      660
cagtccatca cctgcaatgt ggcccacccg gcaagcagca ccaaggtgga caagaaaatt      720
gagcccagag ggcccacaat caagcccgt cctccatgca atgcccagc acctaacctc       780 ttgggtggac catccgtctt catcttccct ccaaagatca aggatgtact catgatctcc      840
ctgagcccca tagtcacatg tgtggtggtg gatgtgagcg aggatgaccc agatgtccag      900
atcagctggt ttgtgaacaa cgtggaagta cacacagctc agacacaaac ccatagagag      960
gattacaaca gtactctccg ggtggtcagt gccctcccca tccagcacca ggactggatg     1020
agtggcaagg agttcaaatg caaggtcaac aacaaagacc tcccagcgcc catcgagaga     1080
accatctcaa acccaaagg gtcagtaaga gctccacagg tatatgtctt gcctccacca     1140
gaagaagaga tgactaagaa acaggtcact ctgacctgca tggtcacaga cttcatgcct     1200
gaagacattt acgtggagtg gaccaacaac gggaaaacag agctaaacta caagaacact     1260
gaaccagtcc tggactctga tggttcttac ttcatgtaca gcaagctgag agtggaaaag     1320
aagaactggg tggaaagaaa tagctactcc tgttcagtgg tccacgaggg tctgcacaat     1380
caccacgaga ctaagagctt ctcccggact ccgggtaaat ga                         1422

<210> SEQ ID NO 16
<211> LENGTH: 750
<212> TYPE: DNA
<213> ORGANISM: Mus musculus

<400> SEQUENCE: 16
atggattttc aagtgcagat tttcagcttc ctgctaatca gtgcctcagt cataatatcc       60
agaggagata tcttgctcac ccaaactcca gcttctttgg ctgtgtctct agggcagagg      120
gccaccatct cctgcaaggc cagccaaagt gttgattatg atggtgatag ttatttgaac      180
tggtaccaac agattccagg acagccaccc aaactcctca tctatgatgc atccaatcta      240
gtttctggga tcccacccag gtttagtggc agtgggtctg gacagacttc accctcaac       300 atccatcctg tggagaaggt ggatgctgca acctatcact gtcagcaaag tactgaggat      360
ccgtggacgt tcggtggagg caccaagctg gaaatcaaac gggctgatgc tgcggccgct      420
ggatcccggg ctgatgctgc accaactgta tccatcttcc caccatccag tgagcagtta      480
acatctggag gtgcctcagt cgtgtgcttc ttgaacaact ctaccccaa agacatcaat       540 gtcaagtgga gattgatgg cagtgaacga caaaatggcg tcctgaacag ttggactgat      600
caggacagca agacagcac ctacagcatg agcagcaccc tcacgttgac caaggacgag      660
tatgaacgac ataacagcta cacctgtgag gccactcaca gagacatcaac ttcacccatt     720 gtcaagagct tcaacaggaa tgagtgttag                                        750

<210> SEQ ID NO 17
<211> LENGTH: 1398
<212> TYPE: DNA
<213> ORGANISM: Mus musculus

<400> SEQUENCE: 17
atggctgtcc tggtgctgtt cctctgcctg gttgcatttc caagctgtgt cctgtcccag       60
gtccagctgc agcagtcagg ggctgaactg gtgaaacctg gggcctcagt gaagatgtcc      120
tgcaaggctt ctggctacac ctttactagc tactggctgc actggataaa acagaggcct      180
ggacagggtc tggaatggat tggatacatt aatcctagga tgattatac tgagtacaat      240
```

```
cagaaattca aggacaaggc cacattgact gcagacaaat cctccagcac agcctatatg      300
caactgagca gcctgacatc tgaggactct gcagtctatt actgcgcgcg aagggatatt      360
actacgttct actggggcca aggcaccact ctcacagtct cctcggccaa acaacagcc       420 ccatcggtct atccactggc ccctgtgtgt ggagatacaa ctggctcctc ggtgactcta      480
ggatgcctgg tcaagggtta tttccctgag ccagtgacct tgacctggaa ctctggatcc      540
ctgtccagtg gtgtgcacac cttcccagct gtcctgcagt ctgacctcta caccctcagc      600
agctcagtga ctgtaacctc gagcacctgg ccagccagt ccatcacctg caatgtggcc       660
cacccggcaa gcagcaccaa ggtggacaag aaaattgagc ccagagggcc cacaatcaag      720
ccctgtcctc catgcaaatg cccagcacct aacctcttgg gtggaccatc cgtcttcatc      780
ttccctccaa agatcaagga tgtactcatg atctccctga gccccatagt cacatgtgtg      840
gtggtggatg tgagcgagga tgacccagat gtccagatca gctggtttgt gaacaacgtg      900
gaagtacaca cagctcagac acaaacccat agagaggatt acaacagtac tctccgggtg      960
gtcagtgccc tccccatcca gcaccaggac tggatgagtg gcaaggagtt caaatgcaag     1020
gtcaacaaca agaccctccc agcgcccatc gagagaacca tctcaaaacc caagggtca     1080 gtaagagctc cacaggtata tgtcttgcct ccaccagaag aagagatgac taagaaacag     1140
gtcactctga cctgcatggt cacagacttc atgcctgaag acatttacgt ggagtggacc     1200
aacaacggga aaacagagct aaactacaag aacactgaac cagtcctgga ctctgatggt     1260
tcttacttca tgtacagcaa gctgagagtg gaaaagaaga ctgggtggaa agaaatagc      1320 tactcctgtt cagtggtcca cgagggtctg cacaatcacc acacgactaa gagcttctcc     1380
cggactccgg gtaaatga                                                   1398

<210> SEQ ID NO 18
<211> LENGTH: 729
<212> TYPE: DNA
<213> ORGANISM: Mus musculus

<400> SEQUENCE: 18
atggattttc aagtgcagat tttcagcttc ctgctaatca gtgcctcagt cataatatcc       60
agaggagata tccagctgac ccagtctcca tcatctctgg ctgtgtctgc aggagaaaac      120
gtcactatga gctgtaagtc cagtcaaagt gtttatca gtgcaaatca caagaactac        180
ttggcctggt accagcagaa accagggcag tctcctaaac tgctgatcta ctgggcatcc      240
actagggaat ctggtgtccc tgatcgcttc acaggcagcg gatctgggac agatttttact    300 cttaccatca gcagagtaca agttgaagac ctggcaattt attattgtca ccaataccctc    360 tcctcgtgga cgttcggtgg cgggaccaag ctggagatca aacgtcgggc tgatgctgca     420
ccaactgtat ccatcttccc accatccagt gagcagttaa catctggagg tgcctcagtc     480
gtgtgcttct tgaacaactt ctaccccaaa gacatcaatg tcaagtggaa gattgatggc     540
agtgaacgac aaaatggcgt cctgaacagt tggactgatc aggacagcaa agacagcacc     600
tacagcatga gcagcaccct cacgttgacc aaggacgagt atgaacgaca taacagctat     660
acctgtgagg ccactcacaa gacatcaact tcacccattg tcaagagctt caacaggaat     720
gagtgttag                                                              729

<210> SEQ ID NO 19
<211> LENGTH: 1416
<212> TYPE: DNA
```

<213> ORGANISM: Mus musculus

<400> SEQUENCE: 19

| | | | | | |
|---|---|---|---|---|---|
| atggctgtcc | tggtgctgtt | cctctgcctg | gttgcatttc | caagctgtgt | cctgtcccag | 60 |
| gtgcaactgc | ggcagcctgg | ggctgagctg | gtgaagcctg | gggcctcagt | gaagatgtcc | 120 |
| tgcaaggctt | ctggctacac | atttaccagt | tacaatatgc | actgggtaaa | gcagacacct | 180 |
| ggacagggcc | tggaatggat | tggagctatt | tatccaggaa | atggtgatac | ttcctacaat | 240 |
| cagaagttca | aggcaaggc | cacattgact | gcagacaaat | cctccagcac | agcctacatg | 300 |
| cagctcagca | gtctgacatc | tgaggactct | gcggtctatt | actgtgcaag | atcgcactac | 360 |
| ggtagtaact | acgtagacta | ctttgactac | tggggccaag | gcaccactct | cacagtctcc | 420 |
| tcagccaaaa | caacagcccc | atcggtctat | ccactggccc | ctgtgtgtgg | agatacaact | 480 |
| ggctcctcgg | tgactctagg | atgcctggtc | aagggttatt | ccctgagcc | agtgaccttg | 540 |
| acctggaact | ctggatccct | gtccagtggt | gtgcacacct | tcccagctgt | cctgcagtct | 600 |
| gacctctaca | ccctcagcag | ctcagtgact | gtaacctcga | gcacctggcc | cagccagtcc | 660 |
| atcacctgca | atgtgcccca | cccggcaagc | agcaccaagg | tggacaagaa | aattgagccc | 720 |
| agagggccca | caatcaagcc | ctgtcctcca | tgcaaatgcc | cagcacctaa | cctcttgggt | 780 |
| ggaccatccg | tcttcatctt | ccctccaaag | atcaaggatg | tactcatgat | ctccctgagc | 840 |
| cccatagtca | catgtgtggt | ggtggatgtg | agcgaggatg | acccagatgt | ccagatcagc | 900 |
| tggtttgtga | acaacgtgga | agtacacaca | gctcagacac | aaacccatag | agaggattac | 960 |
| aacagtactc | tccgggtggt | cagtgccctc | cccatccagc | accaggactg | gatgagtggc | 1020 |
| aaggagttca | aatgcaaggt | caacaacaaa | gacctcccag | cgcccatcga | gagaaccatc | 1080 |
| tcaaaaccca | aagggtcagt | aagagctcca | caggtatatg | tcttgcctcc | accagaagaa | 1140 |
| gagatgacta | agaaacaggt | cactctgacc | tgcatggtca | cagacttcat | gcctgaagac | 1200 |
| atttacgtgg | agtggaccaa | caacgggaaa | acagagctaa | actacaagaa | cactgaacca | 1260 |
| gtcctggact | ctgatggttc | ttacttcatg | tacagcaagc | tgagagtgga | aaagaagaac | 1320 |
| tgggtggaaa | gaaatagcta | ctcctgttca | gtggtccacg | agggtctgca | caatcaccac | 1380 |
| acgactaaga | gcttctcccg | gactccgggt | aaatga | | | 1416 |

<210> SEQ ID NO 20
<211> LENGTH: 711
<212> TYPE: DNA
<213> ORGANISM: Mus musculus

<400> SEQUENCE: 20

| | | | | | |
|---|---|---|---|---|---|
| atggattttc | aagtgcagat | tttcagcttc | ctgctaatca | gtgcctcagt | cataatatcc | 60 |
| agaggacaaa | ttgttctctc | ccagtctcca | gcaatccttt | ctgcatctcc | aggggagaag | 120 |
| gtcacaatga | cttgcagggc | cagctcaagt | ttaagtttca | tgcactggta | ccagcagaag | 180 |
| ccaggatcct | cccccaaacc | ctggatttat | gccacatcca | acctggcttc | tggagtccct | 240 |
| gctcgcttca | gtggcagtgg | gtctgggacc | tcttactctc | tcacaatcag | cagagtggag | 300 |
| gctgaagatg | ctgccactta | tttctgccat | cagtggagta | gtaacccgct | cacgttcggt | 360 |
| gctgggacaa | agctggaact | caaacgtcgg | gctgatgctg | caccaactgt | atccatcttc | 420 |
| ccaccatcca | gtgagcagtt | aacatctgga | ggtgcctcag | tcgtgtgctt | cttgaacaac | 480 |
| ttctacccca | aagacatcaa | tgtcaagtgg | aagattgatg | gcagtgaacg | acaaaatggc | 540 |
| gtcctgaaca | gttggactga | tcaggacagc | aaagacagca | cctacagcat | gagcagcacc | 600 |

| ctcacgttga ccaaggacga gtatgaacga cataacagct atacctgtga ggccactcac | 660 |
| aagacatcaa cttcacccat tgtcaagagc ttcaacagga atgagtgtta g | 711 |

<210> SEQ ID NO 21
<211> LENGTH: 1464
<212> TYPE: DNA
<213> ORGANISM: Artificial Sequence
<220> FEATURE:
<223> OTHER INFORMATION: anti-CD21 heavy chain fused to EBNA3C-5H11
      epitope

<400> SEQUENCE: 21

| atggctgtcc tggtgctgtt cctctgcctg gttgcatttc aagctgtgt cctgtcccag | 60 |
| gtgcagctga aggagtcagg acctggcctg gtggcgccct cacagagcct gtccatcact | 120 |
| tgtactgtct ctggattttc attaaccaac tatggtgtac actgggttcg ccagcctcca | 180 |
| ggaaaaggtc tggagtggct gggaatgatt tgggctggtg aagcacaaa ttataattcg | 240 |
| gctctcatgt ccagactgaa catcaacaaa gacaactcca gagccaagt tttcttagaa | 300 |
| atgaacagtc tgcaaactga tgacactgcc ttgtacttct gtgccagaga agccacctcg | 360 |
| ggctacgtag actatgctgt ggactactgg ggtcaaggaa cgtcagtcac cgtctcctca | 420 |
| gccaaaacaa cagccccatc ggtctatcca ctggcccctg tgtgtggaga tacaactggc | 480 |
| tcctcggtga ctctaggatg cctggtcaag ggttatttcc ctgagccagt gaccttgacc | 540 |
| tggaactctg gatccctgtc cagtggtgtg cacaccttcc cagctgtcct gcagtctgac | 600 |
| ctctacaccc tcagcagctc agtgactgta acctcgagca cctggcccag ccagtccatc | 660 |
| acctgcaatg tggcccaccc ggcaagcagc accaaggtgg acaagaaaat tgagcccaga | 720 |
| gggcccacaa tcaagccctg tcctccatgc aaatgcccag cacctaacct cttgggtgga | 780 |
| ccatccgtct tcatcttccc tccaaagatc aaggatgtac tcatgatctc cctgagcccc | 840 |
| atagtcacat gtgaaaatcc atatcacgcg cggagaggca taaagaaca cgtaatcaca | 900 |
| tgtgtggtgg tggatgtgag cgaggatgac ccagatgtcc agatcagctg gtttgtgaac | 960 |
| aacgtggaag tacacacagc tcagacacaa acccatagag aggattacaa cagtactctc | 1020 |
| cgggtggtca gtgccctccc catccagcac caggactgga tgagtggcaa ggagttcaaa | 1080 |
| tgcaaggtca caacaaaga cctcccagcg cccatcgaga gaaccatctc aaaacccaaa | 1140 |
| gggtcagtaa gagctccaca ggtatatgtc ttgcctccac cagaagaaga gatgactaag | 1200 |
| aaacaggtca ctctgacctg catggtcaca gacttcatgc ctgaagacat ttacgtggag | 1260 |
| tggaccaaca acgggaaaac agagctaaac tacaagaaca ctgaaccagt cctggactct | 1320 |
| gatggttctt acttcatgta cagcaagctg agagtggaaa agaagaactg ggtggaaaga | 1380 |
| aatagctact cctgttcagt ggtccacgag ggtctgcaca atcaccacac gactaagagc | 1440 |
| ttctcccgga ctccgggtaa atga | 1464 |

<210> SEQ ID NO 22
<211> LENGTH: 1473
<212> TYPE: DNA
<213> ORGANISM: Artificial Sequence
<220> FEATURE:
<223> OTHER INFORMATION: anti-CD19 heavy chain fused to EBNA3C-5H11
      epitope

<400> SEQUENCE: 22

| atggctgtcc tggtgctgtt cctctgcctg gttgcatttc aagctgtgt cctgtcccag | 60 |

```
gtgcagctgc agcagtctgg ggctgagctg gtgaggcctg ggtcctcagt gaagatttcc    120
tgcaaggctt ctggctatgc attcagtagc tactggatga actgggtgaa gcagaggcct    180
ggacagggtc ttgagtggat tggacagatt tggcctggag atggtgatac taactacaat    240
ggaaagttca agggtaaagc cactctgact gcagacgaat cctccagcac agcctacatg    300
caactcagca gcctagcatc tgaggactct gcggtctatt tctgtgcaag acgggagact    360
acgacggtag ccgttattac tatgctatg gactactggg gtcaaggaac ctcagtcacc    420
gtctcctcag ccaaaacaac agccccatcg gtctatccac tggcccctgt gtgtggagat    480
acaactggct cctcggtgac tctaggatgc ctggtcaagg gttatttccc tgagccagtg    540
accttgacct ggaactctgg atccctgtcc agtggtgtgc acaccttccc agctgtcctg    600
cagtctgacc tctacaccct cagcagctca gtgactgtaa cctcgagcac ctggcccagc    660
cagtccatca cctgcaatgt ggcccacccg gcaagcagca ccaaggtgga caagaaaatt    720
gagcccagag ggcccacaat caagcccgt cctccatgca aatgcccagc acctaacctc    780
ttgggtggac catccgtctt catcttccct ccaaagatca aggatgtact catgatctcc    840
ctgagcccca tagtcacatg tgtggtggt ggatgtgagc gaggatgacc cagatgtcca gatcagctgg    960
tttgtgaaca cgtggaagt acacacagct cagacacaaa cccatagaga ggattacaac   1020
agtactctcc gggtggtcag tgccctcccc atccagcacc aggactggat gagtggcaag   1080
gagttcaaat gcaaggtcaa caacaaagac ctcccagcgc ccatcgagag aaccatctca   1140
aaacccaaag ggtcagtaag agctccacag gtatatgtct tgcctccacc agaagaagag   1200
atgactaaga aacaggtcac tctgacctgc atggtcacag acttcatgcc tgaagacatt   1260
tacgtggagt ggaccaacaa cgggaaaaca gagctaaact acaagaacac tgaaccagtc   1320
ctggactctg atggttctta cttcatgtac agcaagctga gagtggaaaa gaagaactgg   1380
gtggaaagaa atagcactc ctgttcagtg gtccacgagg gtctgcacaa tcaccacacg   1440
actaagagct ctcccggac tccgggtaaa tga   1473

<210> SEQ ID NO 23
<211> LENGTH: 1449
<212> TYPE: DNA
<213> ORGANISM: Artificial Sequence
<220> FEATURE:
<223> OTHER INFORMATION: anti-CD22 heavy chain fused to EBNA3C-5H11
      epitope

<400> SEQUENCE: 23
atggctgtcc tggtgctgtt cctctgcctg gttgcatttc caagctgtgt cctgtcccag     60
gtccagctgc agcagtcagg ggctgaactg gtgaaacctg gggcctcagt gaagatgtcc    120
tgcaaggctt ctggctacac ctttactagc tactggctgc actggataaa acagaggcct    180
ggacagggtc tggaatggat tggatacatt aatcctagga tgattatac tgagtacaat    240 cagaaattca aggacaaggc cacattgact gcagacaaat cctccagcac agcctatatg    300
caactgagca gcctgacatc tgaggactct gcagtctatt actgcgcgcg aagggatatt    360
actacgttct actggggcca aggcaccact ctcacagtct cctcggccaa acaacagcc    420 ccatcggtct atccactggc cctgtgtgt ggagatacaa ctggctcctc ggtgactcta    480
ggatgcctgg tcaagggtta tttccctgag ccagtgacct tgacctggaa ctctggatcc    540
ctgtccagtg gtgtgcacac cttcccagct gtcctgcagt ctgacctcta caccctcagc    600
```

-continued

| | |
|---|---|
| agctcagtga ctgtaacctc gagcacctgg cccagccagt ccatcacctg caatgtggcc | 660 |
| cacccggcaa gcagcaccaa ggtggacaag aaaattgagc ccagagggcc cacaatcaag | 720 |
| ccctgtcctc catgcaaatg cccagcacct aacctcttgg gtggaccatc cgtcttcatc | 780 |
| ttccctccaa agatcaagga tgtactcatg atctccctga gccccatagt cacatgtgaa | 840 |
| aatccatatc acgcgcggag aggcataaaa gaacacgtaa tcacatgtgt ggtggtggat | 900 |
| gtgagcgagg atgacccaga tgtccagatc agctggtttg tgaacaacgt ggaagtacac | 960 |
| acagctcaga cacaaaccca tagagaggat tacaacagta ctctccgggt ggtcagtgcc | 1020 |
| ctccccatcc agcaccagga ctggatgagt ggcaaggagt tcaaatgcaa ggtcaacaac | 1080 |
| aaagacctcc cagcgcccat cgagagaacc atctcaaaac ccaagggtc agtaagagct | 1140 |
| ccacaggtat atgtcttgcc tccaccagaa gaagagatga ctaagaaaca ggtcactctg | 1200 |
| acctgcatgg tcacagactt catgcctgaa gacatttacg tggagtggac caacaacggg | 1260 |
| aaaacagagc taaactacaa gaacactgaa ccagtcctgg actctgatgg ttcttacttc | 1320 |
| atgtacagca agctgagagt ggaaaagaag aactgggtgg aaagaaatag ctactcctgt | 1380 |
| tcagtggtcc acgagggtct gcacaatcac cacacgacta gagcttctc ccggactccg | 1440 |
| ggtaaatga | 1449 |

<210> SEQ ID NO 24
<211> LENGTH: 1467
<212> TYPE: DNA
<213> ORGANISM: Artificial Sequence
<220> FEATURE:
<223> OTHER INFORMATION: anti-CD20 heavy chain fused to EBNA3C-5H11 epitope

<400> SEQUENCE: 24

| | |
|---|---|
| atggctgtcc tggtgctgtt cctctgcctg gttgcatttc caagctgtgt cctgtcccag | 60 |
| gtgcaactgc ggcagcctgg ggctgagctg gtgaagcctg gggcctcagt gaagatgtcc | 120 |
| tgcaaggctt ctggctacac atttaccagt tacaatatgc actgggtaaa gcagacacct | 180 |
| ggacagggcc tggaatggat tggagctatt tatccaggaa atggtgatac ttcctacaat | 240 |
| cagaagttca aggcaaggc cacattgact gcagacaaat cctccagcac agcctacatg | 300 |
| cagctcagca gtctgacatc tgaggactct gcggtctatt actgtgcaag atcgcactac | 360 |
| ggtagtaact acgtagacta ctttgactac tggggccaag gcaccactct cacagtctcc | 420 |
| tcagccaaaa caacagcccc atcggtctat ccactggccc ctgtgtgtgg agatacaact | 480 |
| ggctcctcgg tgactctagg atgcctggtc aagggttatt ccctgagcc agtgaccttg | 540 |
| acctggaact ctggatccct gtccagtggt gtgcacacct cccagctgt cctgcagtct | 600 |
| gacctctaca ccctcagcag ctcagtgact gtaacctcga gcacctggcc cagccagtcc | 660 |
| atcacctgca atgtggccca cccggcaagc agcaccaagg tggacaagaa aattgagccc | 720 |
| agagggccca aatcaagcc ctgtcctcca tgcaaatgcc cagcacctaa cctcttgggt | 780 |
| ggaccatccg tcttcatctt ccctccaaag atcaaggatg tactcatgat ctccctgagc | 840 |
| cccatagtca catgtgaaaa tccatatcac gcgcggagag gcataaaaga acacgtaatc | 900 |
| acatgtgtgg tggtggatgt gagcgaggat gacccagatg tccagatcag ctggtttgtg | 960 |
| aacaacgtgg aagtacacac agctcagaca caaacccata gagaggatta caacagtact | 1020 |
| ctccgggtgg tcagtgccct ccccatccag caccaggact ggatgagtgg caaggagttc | 1080 |
| aaatgcaagg tcaacaacaa agacctccca gcgcccatcg agagaaccat ctcaaaaccc | 1140 |

-continued

```
aaagggtcag taagagctcc acaggtatat gtcttgcctc caccagaaga agagatgact   1200
aagaaacagg tcactctgac ctgcatggtc acagacttca tgcctgaaga catttacgtg   1260
gagtggacca acaacgggaa aacagagcta aactacaaga acactgaacc agtcctggac   1320
tctgatggtt cttacttcat gtacagcaag ctgagagtgg aaaagaagaa ctgggtggaa   1380
agaaatagct actcctgttc agtggtccac gagggtctgc acaatcacca cacgactaag   1440
agcttctccc ggactccggg taaatga                                      1467
```

<210> SEQ ID NO 25
<211> LENGTH: 470
<212> TYPE: PRT
<213> ORGANISM: Mus musculus

<400> SEQUENCE: 25

```
Met Ala Val Leu Val Leu Phe Leu Cys Leu Val Ala Phe Pro Ser Cys
1               5                   10                  15

Val Leu Ser Gln Val Gln Leu Lys Glu Ser Gly Pro Gly Leu Val Ala
            20                  25                  30

Pro Ser Gln Ser Leu Ser Ile Thr Cys Thr Val Ser Gly Phe Ser Leu
        35                  40                  45

Thr Asn Tyr Gly Val His Trp Val Arg Gln Pro Pro Gly Lys Gly Leu
    50                  55                  60

Glu Trp Leu Gly Met Ile Trp Ala Gly Gly Ser Thr Asn Tyr Asn Ser
65                  70                  75                  80

Ala Leu Met Ser Arg Leu Asn Ile Asn Lys Asp Asn Ser Lys Ser Gln
                85                  90                  95

Val Phe Leu Glu Met Asn Ser Leu Gln Thr Asp Asp Thr Ala Leu Tyr
            100                 105                 110

Phe Cys Ala Arg Glu Ala Thr Ser Gly Tyr Val Asp Tyr Ala Val Asp
        115                 120                 125

Tyr Trp Gly Gln Gly Thr Ser Val Thr Val Ser Ser Ala Lys Thr Thr
    130                 135                 140

Ala Pro Ser Val Tyr Pro Leu Ala Pro Val Cys Gly Asp Thr Thr Gly
145                 150                 155                 160

Ser Ser Val Thr Leu Gly Cys Leu Val Lys Gly Tyr Phe Pro Glu Pro
                165                 170                 175

Val Thr Leu Thr Trp Asn Ser Gly Ser Leu Ser Ser Gly Val His Thr
            180                 185                 190

Phe Pro Ala Val Leu Gln Ser Asp Leu Tyr Thr Leu Ser Ser Ser Val
        195                 200                 205

Thr Val Thr Ser Ser Thr Trp Pro Ser Gln Ser Ile Thr Cys Asn Val
    210                 215                 220

Ala His Pro Ala Ser Ser Thr Lys Val Asp Lys Ile Glu Pro Arg
225                 230                 235                 240

Gly Pro Thr Ile Lys Pro Cys Pro Pro Cys Lys Cys Pro Ala Pro Asn
                245                 250                 255

Leu Leu Gly Gly Pro Ser Val Phe Ile Phe Pro Pro Lys Ile Lys Asp
            260                 265                 270

Val Leu Met Ile Ser Leu Ser Pro Ile Val Thr Cys Val Val Val Asp
        275                 280                 285

Val Ser Glu Asp Asp Pro Asp Val Gln Ile Ser Trp Phe Val Asn Asn
    290                 295                 300

Val Glu Val His Thr Ala Gln Thr Gln Thr His Arg Glu Asp Tyr Asn
305                 310                 315                 320
```

-continued

```
Ser Thr Leu Arg Val Val Ser Ala Leu Pro Ile Gln His Gln Asp Trp
            325                 330                 335

Met Ser Gly Lys Glu Phe Lys Cys Lys Val Asn Asn Lys Asp Leu Pro
        340                 345                 350

Ala Pro Ile Glu Arg Thr Ile Ser Lys Pro Lys Gly Ser Val Arg Ala
            355                 360                 365

Pro Gln Val Tyr Val Leu Pro Pro Pro Glu Glu Met Thr Lys Lys
370                 375                 380

Gln Val Thr Leu Thr Cys Met Val Thr Asp Phe Met Pro Glu Asp Ile
385                 390                 395                 400

Tyr Val Glu Trp Thr Asn Asn Gly Lys Thr Glu Leu Asn Tyr Lys Asn
                405                 410                 415

Thr Glu Pro Val Leu Asp Ser Asp Gly Ser Tyr Phe Met Tyr Ser Lys
            420                 425                 430

Leu Arg Val Glu Lys Lys Asn Trp Val Glu Arg Asn Ser Tyr Ser Cys
        435                 440                 445

Ser Val Val His Glu Gly Leu His Asn His His Thr Thr Lys Ser Phe
    450                 455                 460

Ser Arg Thr Pro Gly Lys
465                 470

<210> SEQ ID NO 26
<211> LENGTH: 235
<212> TYPE: PRT
<213> ORGANISM: Mus musculus

<400> SEQUENCE: 26

Met Asp Phe Gln Val Gln Ile Phe Ser Phe Leu Leu Ile Ser Ala Ser
1               5                   10                  15

Val Ile Ile Ser Arg Gly Gln Ile Ile Leu Asn Gln Ser Pro Ala Ile
            20                  25                  30

Met Ser Ala Phe Pro Gly Glu Lys Val Thr Met Thr Cys Ser Ala Ser
        35                  40                  45

Ser Ser Val Ser Tyr Met His Trp Tyr Gln Gln Lys Ser Gly Thr Ser
    50                  55                  60

Pro Lys Arg Trp Ile Tyr Asp Thr Ser Lys Leu Ala Ser Gly Val Pro
65                  70                  75                  80

Ala Arg Phe Ser Gly Ser Gly Ser Gly Thr Ser Tyr Ser Leu Thr Ile
                85                  90                  95

Ser Ser Met Glu Ala Glu Asp Ala Ala Thr Tyr Tyr Cys Gln Gln Trp
            100                 105                 110

Ser Ser Ser Pro Leu Thr Phe Gly Ala Gly Thr Lys Leu Glu Leu Lys
        115                 120                 125

Arg Ala Asp Ala Ala Pro Thr Val Ser Ile Phe Pro Pro Ser Ser Glu
    130                 135                 140

Gln Leu Thr Ser Gly Gly Ala Ser Val Val Cys Phe Leu Asn Asn Phe
145                 150                 155                 160

Tyr Pro Lys Asp Ile Asn Val Lys Trp Lys Ile Asp Gly Ser Glu Arg
                165                 170                 175

Gln Asn Gly Val Leu Asn Ser Trp Thr Asp Gln Asp Ser Lys Asp Ser
            180                 185                 190

Thr Tyr Ser Met Ser Ser Thr Leu Thr Leu Thr Lys Asp Glu Tyr Glu
        195                 200                 205

Arg His Asn Ser Tyr Thr Cys Glu Ala Thr His Lys Thr Ser Thr Ser
```

```
              210                 215                 220
Pro Ile Val Lys Ser Phe Asn Arg Asn Glu Cys
225                 230                 235

<210> SEQ ID NO 27
<211> LENGTH: 473
<212> TYPE: PRT
<213> ORGANISM: Mus musculus

<400> SEQUENCE: 27

Met Ala Val Leu Val Leu Phe Leu Cys Leu Ala Phe Pro Ser Cys
1                   5                   10                  15

Val Leu Ser Gln Val Gln Leu Gln Gln Ser Gly Ala Glu Leu Val Arg
                20                  25                  30

Pro Gly Ser Ser Val Lys Ile Ser Cys Lys Ala Ser Gly Tyr Ala Phe
            35                  40                  45

Ser Ser Tyr Trp Met Asn Trp Val Lys Gln Arg Pro Gly Gln Gly Leu
        50                  55                  60

Glu Trp Ile Gly Gln Ile Trp Pro Gly Asp Gly Asp Thr Asn Tyr Asn
65                  70                  75                  80

Gly Lys Phe Lys Gly Lys Ala Thr Leu Thr Ala Asp Glu Ser Ser Ser
                85                  90                  95

Thr Ala Tyr Met Gln Leu Ser Ser Leu Ala Ser Glu Asp Ser Ala Val
            100                 105                 110

Tyr Phe Cys Ala Arg Arg Glu Thr Thr Thr Val Gly Arg Tyr Tyr Tyr
        115                 120                 125

Ala Met Asp Tyr Trp Gly Gln Gly Thr Ser Val Thr Val Ser Ser Ala
        130                 135                 140

Lys Thr Thr Ala Pro Ser Val Tyr Pro Leu Ala Pro Val Cys Gly Asp
145                 150                 155                 160

Thr Thr Gly Ser Ser Val Thr Leu Gly Cys Leu Val Lys Gly Tyr Phe
                165                 170                 175

Pro Glu Pro Val Thr Leu Thr Trp Asn Ser Gly Ser Leu Ser Ser Gly
            180                 185                 190

Val His Thr Phe Pro Ala Val Leu Gln Ser Asp Leu Tyr Thr Leu Ser
        195                 200                 205

Ser Ser Val Thr Val Thr Ser Ser Thr Trp Pro Ser Gln Ser Ile Thr
        210                 215                 220

Cys Asn Val Ala His Pro Ala Ser Ser Thr Lys Val Asp Lys Lys Ile
225                 230                 235                 240

Glu Pro Arg Gly Pro Thr Ile Lys Pro Cys Pro Pro Cys Lys Cys Pro
                245                 250                 255

Ala Pro Asn Leu Leu Gly Gly Pro Ser Val Phe Ile Phe Pro Pro Lys
            260                 265                 270

Ile Lys Asp Val Leu Met Ile Ser Leu Ser Pro Ile Val Thr Cys Val
        275                 280                 285

Val Val Asp Val Ser Glu Asp Asp Pro Asp Val Gln Ile Ser Trp Phe
        290                 295                 300

Val Asn Asn Val Glu Val His Thr Ala Gln Thr Gln Thr His Arg Glu
305                 310                 315                 320

Asp Tyr Asn Ser Thr Leu Arg Val Val Ser Ala Leu Pro Ile Gln His
                325                 330                 335

Gln Asp Trp Met Ser Gly Lys Glu Phe Lys Cys Lys Val Asn Asn Lys
            340                 345                 350
```

```
Asp Leu Pro Ala Pro Ile Glu Arg Thr Ile Ser Lys Pro Lys Gly Ser
            355                 360                 365

Val Arg Ala Pro Gln Val Tyr Val Leu Pro Pro Glu Glu Glu Met
    370                 375                 380

Thr Lys Gln Val Thr Leu Thr Cys Met Val Thr Asp Phe Met Pro
385                 390                 395                 400

Glu Asp Ile Tyr Val Glu Trp Thr Asn Asn Gly Lys Thr Glu Leu Asn
                405                 410                 415

Tyr Lys Asn Thr Glu Pro Val Leu Asp Ser Asp Gly Ser Tyr Phe Met
            420                 425                 430

Tyr Ser Lys Leu Arg Val Glu Lys Lys Asn Trp Val Glu Arg Asn Ser
            435                 440                 445

Tyr Ser Cys Ser Val Val His Glu Gly Leu His Asn His His Thr Thr
            450                 455                 460

Lys Ser Phe Ser Arg Thr Pro Gly Lys
465                 470

<210> SEQ ID NO 28
<211> LENGTH: 249
<212> TYPE: PRT
<213> ORGANISM: Mus musculus

<400> SEQUENCE: 28

Met Asp Phe Gln Val Gln Ile Phe Ser Phe Leu Leu Ile Ser Ala Ser
1               5                   10                  15

Val Ile Ile Ser Arg Gly Asp Ile Leu Leu Thr Gln Thr Pro Ala Ser
                20                  25                  30

Leu Ala Val Ser Leu Gly Gln Arg Ala Thr Ile Ser Cys Lys Ala Ser
            35                  40                  45

Gln Ser Val Asp Tyr Asp Gly Asp Ser Tyr Leu Asn Trp Tyr Gln Gln
50                  55                  60

Ile Pro Gly Gln Pro Pro Lys Leu Leu Ile Tyr Asp Ala Ser Asn Leu
65                  70                  75                  80

Val Ser Gly Ile Pro Pro Arg Phe Ser Gly Ser Gly Ser Gly Thr Asp
                85                  90                  95

Phe Thr Leu Asn Ile His Pro Val Glu Lys Val Asp Ala Ala Thr Tyr
            100                 105                 110

His Cys Gln Gln Ser Thr Glu Asp Pro Trp Thr Phe Gly Gly Gly Thr
        115                 120                 125

Lys Leu Glu Ile Lys Arg Ala Asp Ala Ala Ala Gly Ser Arg Ala
    130                 135                 140

Asp Ala Ala Pro Thr Val Ser Ile Phe Pro Pro Ser Ser Glu Gln Leu
145                 150                 155                 160

Thr Ser Gly Gly Ala Ser Val Val Cys Phe Leu Asn Asn Phe Tyr Pro
                165                 170                 175

Lys Asp Ile Asn Val Lys Trp Lys Ile Asp Gly Ser Glu Arg Gln Asn
            180                 185                 190

Gly Val Leu Asn Ser Trp Thr Asp Gln Asp Ser Lys Asp Ser Thr Tyr
        195                 200                 205

Ser Met Ser Ser Thr Leu Thr Leu Thr Lys Asp Glu Tyr Glu Arg His
    210                 215                 220

Asn Ser Tyr Thr Cys Glu Ala Thr His Lys Thr Ser Thr Ser Pro Ile
225                 230                 235                 240

Val Lys Ser Phe Asn Arg Asn Glu Cys
                245
```

<210> SEQ ID NO 29
<211> LENGTH: 465
<212> TYPE: PRT
<213> ORGANISM: Mus musculus

<400> SEQUENCE: 29

Met Ala Val Leu Val Leu Phe Leu Cys Leu Ala Phe Pro Ser Cys
1               5                   10                  15

Val Leu Ser Gln Val Gln Leu Gln Gln Ser Gly Ala Glu Leu Val Lys
            20                  25                  30

Pro Gly Ala Ser Val Lys Met Ser Cys Lys Ala Ser Gly Tyr Thr Phe
        35                  40                  45

Thr Ser Tyr Trp Leu His Trp Ile Lys Gln Arg Pro Gly Gln Gly Leu
    50                  55                  60

Glu Trp Ile Gly Tyr Ile Asn Pro Arg Asn Asp Tyr Thr Glu Tyr Asn
65                  70                  75                  80

Gln Lys Phe Lys Asp Lys Ala Thr Leu Thr Ala Asp Lys Ser Ser Ser
                85                  90                  95

Thr Ala Tyr Met Gln Leu Ser Ser Leu Thr Ser Glu Asp Ser Ala Val
            100                 105                 110

Tyr Tyr Cys Ala Arg Arg Asp Ile Thr Thr Phe Tyr Trp Gly Gln Gly
        115                 120                 125

Thr Thr Leu Thr Val Ser Ser Ala Lys Thr Thr Ala Pro Ser Val Tyr
    130                 135                 140

Pro Leu Ala Pro Val Cys Gly Asp Thr Thr Gly Ser Ser Val Thr Leu
145                 150                 155                 160

Gly Cys Leu Val Lys Gly Tyr Phe Pro Glu Pro Val Thr Leu Thr Trp
                165                 170                 175

Asn Ser Gly Ser Leu Ser Ser Gly Val His Thr Phe Pro Ala Val Leu
            180                 185                 190

Gln Ser Asp Leu Tyr Thr Leu Ser Ser Ser Val Thr Val Thr Ser Ser
        195                 200                 205

Thr Trp Pro Ser Gln Ser Ile Thr Cys Asn Val Ala His Pro Ala Ser
    210                 215                 220

Ser Thr Lys Val Asp Lys Lys Ile Glu Pro Arg Gly Pro Thr Ile Lys
225                 230                 235                 240

Pro Cys Pro Pro Cys Lys Cys Pro Ala Pro Asn Leu Leu Gly Gly Pro
                245                 250                 255

Ser Val Phe Ile Phe Pro Pro Lys Ile Lys Asp Val Leu Met Ile Ser
            260                 265                 270

Leu Ser Pro Ile Val Thr Cys Val Val Val Asp Val Ser Glu Asp Asp
        275                 280                 285

Pro Asp Val Gln Ile Ser Trp Phe Val Asn Asn Val Glu Val His Thr
    290                 295                 300

Ala Gln Thr Gln Thr His Arg Glu Asp Tyr Asn Ser Thr Leu Arg Val
305                 310                 315                 320

Val Ser Ala Leu Pro Ile Gln His Gln Asp Trp Met Ser Gly Lys Glu
                325                 330                 335

Phe Lys Cys Lys Val Asn Asn Lys Asp Leu Pro Ala Pro Ile Glu Arg
            340                 345                 350

Thr Ile Ser Lys Pro Lys Gly Ser Val Arg Ala Pro Gln Val Tyr Val
        355                 360                 365

Leu Pro Pro Pro Glu Glu Glu Met Thr Lys Lys Gln Val Thr Leu Thr

```
              370                 375                 380
Cys Met Val Thr Asp Phe Met Pro Glu Asp Ile Tyr Val Glu Trp Thr
385                 390                 395                 400

Asn Asn Gly Lys Thr Glu Leu Asn Tyr Lys Asn Thr Glu Pro Val Leu
            405                 410                 415

Asp Ser Asp Gly Ser Tyr Phe Met Tyr Ser Lys Leu Arg Val Glu Lys
            420                 425                 430

Lys Asn Trp Val Glu Arg Asn Ser Tyr Ser Cys Ser Val Val His Glu
            435                 440                 445

Gly Leu His Asn His His Thr Thr Lys Ser Phe Ser Arg Thr Pro Gly
            450                 455                 460

Lys
465

<210> SEQ ID NO 30
<211> LENGTH: 242
<212> TYPE: PRT
<213> ORGANISM: Mus musculus

<400> SEQUENCE: 30

Met Asp Phe Gln Val Gln Ile Phe Ser Phe Leu Leu Ile Ser Ala Ser
1               5                   10                  15

Val Ile Ile Ser Arg Gly Asp Ile Gln Leu Thr Gln Ser Pro Ser Ser
            20                  25                  30

Leu Ala Val Ser Ala Gly Glu Asn Val Thr Met Ser Cys Lys Ser Ser
            35                  40                  45

Gln Ser Val Leu Tyr Ser Ala Asn His Lys Asn Tyr Leu Ala Trp Tyr
50                  55                  60

Gln Gln Lys Pro Gly Gln Ser Pro Lys Leu Leu Ile Tyr Trp Ala Ser
65                  70                  75                  80

Thr Arg Glu Ser Gly Val Pro Asp Arg Phe Thr Gly Ser Gly Ser Gly
            85                  90                  95

Thr Asp Phe Thr Leu Thr Ile Ser Arg Val Gln Val Glu Asp Leu Ala
            100                 105                 110

Ile Tyr Tyr Cys His Gln Tyr Leu Ser Ser Trp Thr Phe Gly Gly Gly
            115                 120                 125

Thr Lys Leu Glu Ile Lys Arg Ala Asp Ala Ala Pro Thr Val Ser
            130                 135                 140

Ile Phe Pro Pro Ser Ser Glu Gln Leu Thr Ser Gly Gly Ala Ser Val
145                 150                 155                 160

Val Cys Phe Leu Asn Asn Phe Tyr Pro Lys Asp Ile Asn Val Lys Trp
            165                 170                 175

Lys Ile Asp Gly Ser Glu Arg Gln Asn Gly Val Leu Asn Ser Trp Thr
            180                 185                 190

Asp Gln Asp Ser Lys Asp Ser Thr Tyr Ser Met Ser Ser Thr Leu Thr
            195                 200                 205

Leu Thr Lys Asp Glu Tyr Glu Arg His Asn Ser Tyr Thr Cys Glu Ala
            210                 215                 220

Thr His Lys Thr Ser Thr Ser Pro Ile Val Lys Ser Phe Asn Arg Asn
225                 230                 235                 240

Glu Cys

<210> SEQ ID NO 31
<211> LENGTH: 471
<212> TYPE: PRT
```

<213> ORGANISM: Mus musculus

<400> SEQUENCE: 31

Met Ala Val Leu Val Leu Phe Leu Cys Leu Val Ala Phe Pro Ser Cys
1               5                   10                  15

Val Leu Ser Gln Val Gln Leu Arg Gln Pro Gly Ala Glu Leu Val Lys
            20                  25                  30

Pro Gly Ala Ser Val Lys Met Ser Cys Lys Ala Ser Gly Tyr Thr Phe
        35                  40                  45

Thr Ser Tyr Asn Met His Trp Val Lys Gln Thr Pro Gly Gln Gly Leu
    50                  55                  60

Glu Trp Ile Gly Ala Ile Tyr Pro Gly Asn Gly Asp Thr Ser Tyr Asn
65                  70                  75                  80

Gln Lys Phe Lys Gly Lys Ala Thr Leu Thr Ala Asp Lys Ser Ser Ser
                85                  90                  95

Thr Ala Tyr Met Gln Leu Ser Ser Leu Thr Ser Glu Asp Ser Ala Val
            100                 105                 110

Tyr Tyr Cys Ala Arg Ser His Tyr Gly Ser Asn Tyr Val Asp Tyr Phe
        115                 120                 125

Asp Tyr Trp Gly Gln Gly Thr Thr Leu Thr Val Ser Ser Ala Lys Thr
130                 135                 140

Thr Ala Pro Ser Val Tyr Pro Leu Ala Pro Val Cys Gly Asp Thr Thr
145                 150                 155                 160

Gly Ser Ser Val Thr Leu Gly Cys Leu Val Lys Gly Tyr Phe Pro Glu
                165                 170                 175

Pro Val Thr Leu Thr Trp Asn Ser Gly Ser Leu Ser Ser Gly Val His
            180                 185                 190

Thr Phe Pro Ala Val Leu Gln Ser Asp Leu Tyr Thr Leu Ser Ser Ser
        195                 200                 205

Val Thr Val Thr Ser Ser Thr Trp Pro Ser Gln Ser Ile Thr Cys Asn
210                 215                 220

Val Ala His Pro Ala Ser Ser Thr Lys Val Asp Lys Lys Ile Glu Pro
225                 230                 235                 240

Arg Gly Pro Thr Ile Lys Pro Cys Pro Pro Cys Lys Cys Pro Ala Pro
                245                 250                 255

Asn Leu Leu Gly Gly Pro Ser Val Phe Ile Phe Pro Pro Lys Ile Lys
            260                 265                 270

Asp Val Leu Met Ile Ser Leu Ser Pro Ile Val Thr Cys Val Val Val
        275                 280                 285

Asp Val Ser Glu Asp Asp Pro Asp Val Gln Ile Ser Trp Phe Val Asn
290                 295                 300

Asn Val Glu Val His Thr Ala Gln Thr Gln Thr His Arg Glu Asp Tyr
305                 310                 315                 320

Asn Ser Thr Leu Arg Val Val Ser Ala Leu Pro Ile Gln His Gln Asp
                325                 330                 335

Trp Met Ser Gly Lys Glu Phe Lys Cys Lys Val Asn Asn Lys Asp Leu
            340                 345                 350

Pro Ala Pro Ile Glu Arg Thr Ile Ser Lys Pro Lys Gly Ser Val Arg
        355                 360                 365

Ala Pro Gln Val Tyr Val Leu Pro Pro Pro Glu Glu Glu Met Thr Lys
370                 375                 380

Lys Gln Val Thr Leu Thr Cys Met Val Thr Asp Phe Met Pro Glu Asp
385                 390                 395                 400

```
Ile Tyr Val Glu Trp Thr Asn Asn Gly Lys Thr Glu Leu Asn Tyr Lys
            405                 410                 415

Asn Thr Glu Pro Val Leu Asp Ser Asp Gly Ser Tyr Phe Met Tyr Ser
        420                 425                 430

Lys Leu Arg Val Glu Lys Lys Asn Trp Val Glu Arg Asn Ser Tyr Ser
    435                 440                 445

Cys Ser Val Val His Glu Gly Leu His Asn His His Thr Thr Lys Ser
450                 455                 460

Phe Ser Arg Thr Pro Gly Lys
465                 470
```

<210> SEQ ID NO 32
<211> LENGTH: 236
<212> TYPE: PRT
<213> ORGANISM: Mus musculus

<400> SEQUENCE: 32

```
Met Asp Phe Gln Val Gln Ile Phe Ser Phe Leu Leu Ile Ser Ala Ser
1               5                   10                  15

Val Ile Ile Ser Arg Gly Gln Ile Val Leu Ser Gln Ser Pro Ala Ile
            20                  25                  30

Leu Ser Ala Ser Pro Gly Glu Lys Val Thr Met Thr Cys Arg Ala Ser
        35                  40                  45

Ser Ser Leu Ser Phe Met His Trp Tyr Gln Gln Lys Pro Gly Ser Ser
    50                  55                  60

Pro Lys Pro Trp Ile Tyr Ala Thr Ser Asn Leu Ala Ser Gly Val Pro
65                  70                  75                  80

Ala Arg Phe Ser Gly Ser Gly Ser Gly Thr Ser Tyr Ser Leu Thr Ile
                85                  90                  95

Ser Arg Val Glu Ala Glu Asp Ala Ala Thr Tyr Phe Cys His Gln Trp
            100                 105                 110

Ser Ser Asn Pro Leu Thr Phe Gly Ala Gly Thr Lys Leu Glu Leu Lys
        115                 120                 125

Arg Arg Ala Asp Ala Ala Pro Thr Val Ser Ile Phe Pro Pro Ser Ser
130                 135                 140

Glu Gln Leu Thr Ser Gly Gly Ala Ser Val Val Cys Phe Leu Asn Asn
145                 150                 155                 160

Phe Tyr Pro Lys Asp Ile Asn Val Lys Trp Lys Ile Asp Gly Ser Glu
                165                 170                 175

Arg Gln Asn Gly Val Leu Asn Ser Trp Thr Asp Gln Asp Ser Lys Asp
            180                 185                 190

Ser Thr Tyr Ser Met Ser Ser Thr Leu Thr Leu Thr Lys Asp Glu Tyr
        195                 200                 205

Glu Arg His Asn Ser Tyr Thr Cys Glu Ala Thr His Lys Thr Ser Thr
210                 215                 220

Ser Pro Ile Val Lys Ser Phe Asn Arg Asn Glu Cys
225                 230                 235
```

<210> SEQ ID NO 33
<211> LENGTH: 487
<212> TYPE: PRT
<213> ORGANISM: Artificial Sequence
<220> FEATURE:
<223> OTHER INFORMATION: anti-CD21 heavy chain fused to EBNA3C-5H11 epitope

<400> SEQUENCE: 33

```
Met Ala Val Leu Val Leu Phe Leu Cys Leu Val Ala Phe Pro Ser Cys
1               5                   10                  15

Val Leu Ser Gln Val Gln Leu Lys Glu Ser Gly Pro Gly Leu Val Ala
            20                  25                  30

Pro Ser Gln Ser Leu Ser Ile Thr Cys Thr Val Ser Gly Phe Ser Leu
            35                  40                  45

Thr Asn Tyr Gly Val His Trp Val Arg Gln Pro Pro Gly Lys Gly Leu
    50                  55                  60

Glu Trp Leu Gly Met Ile Trp Ala Gly Gly Ser Thr Asn Tyr Asn Ser
65                  70                  75                  80

Ala Leu Met Ser Arg Leu Asn Ile Asn Lys Asp Asn Ser Lys Ser Gln
                85                  90                  95

Val Phe Leu Glu Met Asn Ser Leu Gln Thr Asp Asp Thr Ala Leu Tyr
            100                 105                 110

Phe Cys Ala Arg Glu Ala Thr Ser Gly Tyr Val Asp Tyr Ala Val Asp
            115                 120                 125

Tyr Trp Gly Gln Gly Thr Ser Val Thr Val Ser Ser Ala Lys Thr Thr
130                 135                 140

Ala Pro Ser Val Tyr Pro Leu Ala Pro Val Cys Gly Asp Thr Thr Gly
145                 150                 155                 160

Ser Ser Val Thr Leu Gly Cys Leu Val Lys Gly Tyr Phe Pro Glu Pro
            165                 170                 175

Val Thr Leu Thr Trp Asn Ser Gly Ser Leu Ser Ser Gly Val His Thr
            180                 185                 190

Phe Pro Ala Val Leu Gln Ser Asp Leu Tyr Thr Leu Ser Ser Ser Val
            195                 200                 205

Thr Val Thr Ser Ser Thr Trp Pro Ser Gln Ser Ile Thr Cys Asn Val
210                 215                 220

Ala His Pro Ala Ser Ser Thr Lys Val Asp Lys Lys Ile Glu Pro Arg
225                 230                 235                 240

Gly Pro Thr Ile Lys Pro Cys Pro Pro Cys Lys Cys Pro Ala Pro Asn
                245                 250                 255

Leu Leu Gly Gly Pro Ser Val Phe Ile Phe Pro Pro Lys Ile Lys Asp
            260                 265                 270

Val Leu Met Ile Ser Leu Ser Pro Ile Val Thr Cys Glu Asn Pro Tyr
            275                 280                 285

His Ala Arg Arg Gly Ile Lys Glu His Val Ile Thr Cys Val Val Val
            290                 295                 300

Asp Val Ser Glu Asp Asp Pro Asp Val Gln Ile Ser Trp Phe Val Asn
305                 310                 315                 320

Asn Val Glu Val His Thr Ala Gln Thr Gln Thr His Arg Glu Asp Tyr
                325                 330                 335

Asn Ser Thr Leu Arg Val Val Ser Ala Leu Pro Ile Gln His Gln Asp
            340                 345                 350

Trp Met Ser Gly Lys Glu Phe Lys Cys Lys Val Asn Asn Lys Asp Leu
            355                 360                 365

Pro Ala Pro Ile Glu Arg Thr Ile Ser Lys Pro Lys Gly Ser Val Arg
            370                 375                 380

Ala Pro Gln Val Tyr Val Leu Pro Pro Glu Glu Glu Met Thr Lys
385                 390                 395                 400

Lys Gln Val Thr Leu Thr Cys Met Val Thr Asp Phe Met Pro Glu Asp
                405                 410                 415

Ile Tyr Val Glu Trp Thr Asn Asn Gly Lys Thr Glu Leu Asn Tyr Lys
```

```
                    420              425              430
Asn Thr Glu Pro Val Leu Asp Ser Asp Gly Ser Tyr Phe Met Tyr Ser
            435              440              445

Lys Leu Arg Val Glu Lys Lys Asn Trp Val Glu Arg Asn Ser Tyr Ser
        450              455              460

Cys Ser Val Val His Glu Gly Leu His Asn His His Thr Thr Lys Ser
465             470              475              480

Phe Ser Arg Thr Pro Gly Lys
                485

<210> SEQ ID NO 34
<211> LENGTH: 490
<212> TYPE: PRT
<213> ORGANISM: Artificial Sequence
<220> FEATURE:
<223> OTHER INFORMATION: anti-CD19 heavy chain fused to EBNA3C-5H11
      epitope

<400> SEQUENCE: 34

Met Ala Val Leu Val Leu Phe Leu Cys Leu Val Ala Phe Pro Ser Cys
1               5                   10                  15

Val Leu Ser Gln Val Gln Leu Gln Gln Ser Gly Ala Glu Leu Val Arg
            20                  25                  30

Pro Gly Ser Ser Val Lys Ile Ser Cys Lys Ala Ser Gly Tyr Ala Phe
        35                  40                  45

Ser Ser Tyr Trp Met Asn Trp Val Lys Gln Arg Pro Gly Gln Gly Leu
    50                  55                  60

Glu Trp Ile Gly Gln Ile Trp Pro Gly Asp Gly Asp Thr Asn Tyr Asn
65                  70                  75                  80

Gly Lys Phe Lys Gly Lys Ala Thr Leu Thr Ala Asp Glu Ser Ser Ser
                85                  90                  95

Thr Ala Tyr Met Gln Leu Ser Ser Leu Ala Ser Glu Asp Ser Ala Val
            100                 105                 110

Tyr Phe Cys Ala Arg Arg Glu Thr Thr Thr Val Gly Arg Tyr Tyr Tyr
        115                 120                 125

Ala Met Asp Tyr Trp Gly Gln Gly Thr Ser Val Thr Val Ser Ser Ala
    130                 135                 140

Lys Thr Thr Ala Pro Ser Val Tyr Pro Leu Ala Pro Val Cys Gly Asp
145                 150                 155                 160

Thr Thr Gly Ser Ser Val Thr Leu Gly Cys Leu Val Lys Gly Tyr Phe
                165                 170                 175

Pro Glu Pro Val Thr Leu Thr Trp Asn Ser Gly Ser Leu Ser Ser Gly
            180                 185                 190

Val His Thr Phe Pro Ala Val Leu Gln Ser Asp Leu Tyr Thr Leu Ser
        195                 200                 205

Ser Ser Val Thr Val Thr Ser Ser Thr Trp Pro Ser Gln Ser Ile Thr
    210                 215                 220

Cys Asn Val Ala His Pro Ala Ser Ser Thr Lys Val Asp Lys Lys Ile
225                 230                 235                 240

Glu Pro Arg Gly Pro Thr Ile Lys Pro Cys Pro Pro Cys Lys Cys Pro
                245                 250                 255

Ala Pro Asn Leu Leu Gly Gly Pro Ser Val Phe Ile Phe Pro Pro Lys
            260                 265                 270

Ile Lys Asp Val Leu Met Ile Ser Leu Ser Pro Ile Val Thr Cys Glu
        275                 280                 285
```

```
Asn Pro Tyr His Ala Arg Arg Gly Ile Lys Glu His Val Ile Thr Cys
    290                 295                 300
Val Val Val Asp Val Ser Glu Asp Pro Asp Val Gln Ile Ser Trp
305                 310                 315                 320
Phe Val Asn Asn Val Glu Val His Thr Ala Gln Thr Gln Thr His Arg
                325                 330                 335
Glu Asp Tyr Asn Ser Thr Leu Arg Val Val Ser Ala Leu Pro Ile Gln
            340                 345                 350
His Gln Asp Trp Met Ser Gly Lys Glu Phe Lys Cys Lys Val Asn Asn
        355                 360                 365
Lys Asp Leu Pro Ala Pro Ile Glu Arg Thr Ile Ser Lys Pro Lys Gly
370                 375                 380
Ser Val Arg Ala Pro Gln Val Tyr Val Leu Pro Pro Glu Glu
385                 390                 395                 400
Met Thr Lys Lys Gln Val Thr Leu Thr Cys Met Val Thr Asp Phe Met
                405                 410                 415
Pro Glu Asp Ile Tyr Val Glu Trp Thr Asn Asn Gly Lys Thr Glu Leu
            420                 425                 430
Asn Tyr Lys Asn Thr Glu Pro Val Leu Asp Ser Asp Gly Ser Tyr Phe
        435                 440                 445
Met Tyr Ser Lys Leu Arg Val Glu Lys Lys Asn Trp Val Glu Arg Asn
450                 455                 460
Ser Tyr Ser Cys Ser Val His Glu Gly Leu His Asn His His Thr
465                 470                 475                 480
Thr Lys Ser Phe Ser Arg Thr Pro Gly Lys
                485                 490

<210> SEQ ID NO 35
<211> LENGTH: 482
<212> TYPE: PRT
<213> ORGANISM: Artificial Sequence
<220> FEATURE:
<223> OTHER INFORMATION: anti-CD22 heavy chain fused to EBNA3C-5H11
      epitope

<400> SEQUENCE: 35

Met Ala Val Leu Val Leu Phe Leu Cys Leu Val Ala Phe Pro Ser Cys
1               5                   10                  15
Val Leu Ser Gln Val Gln Leu Gln Gln Ser Gly Ala Glu Leu Val Lys
            20                  25                  30
Pro Gly Ala Ser Val Lys Met Ser Cys Lys Ala Ser Gly Tyr Thr Phe
        35                  40                  45
Thr Ser Tyr Trp Leu His Trp Ile Lys Gln Arg Pro Gly Gln Gly Leu
50                  55                  60
Glu Trp Ile Gly Tyr Ile Asn Pro Arg Asn Asp Tyr Thr Glu Tyr Asn
65                  70                  75                  80
Gln Lys Phe Lys Asp Lys Ala Thr Leu Thr Ala Asp Lys Ser Ser Ser
                85                  90                  95
Thr Ala Tyr Met Gln Leu Ser Ser Leu Thr Ser Glu Asp Ser Ala Val
            100                 105                 110
Tyr Tyr Cys Ala Arg Arg Asp Ile Thr Thr Phe Tyr Trp Gly Gln Gly
        115                 120                 125
Thr Thr Leu Thr Val Ser Ser Ala Lys Thr Thr Ala Pro Ser Val Tyr
130                 135                 140
Pro Leu Ala Pro Val Cys Gly Asp Thr Thr Gly Ser Ser Val Thr Leu
145                 150                 155                 160
```

Gly Cys Leu Val Lys Gly Tyr Phe Pro Glu Pro Val Thr Leu Thr Trp
                165                 170                 175

Asn Ser Gly Ser Leu Ser Ser Gly Val His Thr Phe Pro Ala Val Leu
            180                 185                 190

Gln Ser Asp Leu Tyr Thr Leu Ser Ser Val Thr Val Thr Ser Ser
        195                 200                 205

Thr Trp Pro Ser Gln Ser Ile Thr Cys Asn Val Ala His Pro Ala Ser
    210                 215                 220

Ser Thr Lys Val Asp Lys Lys Ile Glu Pro Arg Gly Pro Thr Ile Lys
225                 230                 235                 240

Pro Cys Pro Pro Cys Lys Cys Pro Ala Pro Asn Leu Leu Gly Gly Pro
                245                 250                 255

Ser Val Phe Ile Phe Pro Pro Lys Ile Lys Asp Val Leu Met Ile Ser
            260                 265                 270

Leu Ser Pro Ile Val Thr Cys Glu Asn Pro Tyr His Ala Arg Arg Gly
        275                 280                 285

Ile Lys Glu His Val Ile Thr Cys Val Val Asp Val Ser Glu Asp
    290                 295                 300

Asp Pro Asp Val Gln Ile Ser Trp Phe Val Asn Asn Val Glu Val His
305                 310                 315                 320

Thr Ala Gln Thr Gln Thr His Arg Glu Asp Tyr Asn Ser Thr Leu Arg
                325                 330                 335

Val Val Ser Ala Leu Pro Ile Gln His Gln Asp Trp Met Ser Gly Lys
            340                 345                 350

Glu Phe Lys Cys Lys Val Asn Asn Lys Asp Leu Pro Ala Pro Ile Glu
        355                 360                 365

Arg Thr Ile Ser Lys Pro Lys Gly Ser Val Arg Ala Pro Gln Val Tyr
    370                 375                 380

Val Leu Pro Pro Pro Glu Glu Glu Met Thr Lys Lys Gln Val Thr Leu
385                 390                 395                 400

Thr Cys Met Val Thr Asp Phe Met Pro Glu Asp Ile Tyr Val Glu Trp
                405                 410                 415

Thr Asn Asn Gly Lys Thr Glu Leu Asn Tyr Lys Asn Thr Glu Pro Val
            420                 425                 430

Leu Asp Ser Asp Gly Ser Tyr Phe Met Tyr Ser Lys Leu Arg Val Glu
        435                 440                 445

Lys Lys Asn Trp Val Glu Arg Asn Ser Tyr Ser Cys Ser Val Val His
    450                 455                 460

Glu Gly Leu His Asn His His Thr Thr Lys Ser Phe Ser Arg Thr Pro
465                 470                 475                 480

Gly Lys

<210> SEQ ID NO 36
<211> LENGTH: 488
<212> TYPE: PRT
<213> ORGANISM: Artificial Sequence
<220> FEATURE:
<223> OTHER INFORMATION: anti-CD20 heavy chain fused to EBNA3C-5H11
      epitope

<400> SEQUENCE: 36

Met Ala Val Leu Val Leu Phe Leu Cys Leu Val Ala Phe Pro Ser Cys
1               5                   10                  15

Val Leu Ser Gln Val Gln Leu Arg Gln Pro Gly Ala Glu Leu Val Lys
            20                  25                  30

Pro Gly Ala Ser Val Lys Met Ser Cys Lys Ala Ser Gly Tyr Thr Phe
            35                  40                  45

Thr Ser Tyr Asn Met His Trp Val Lys Gln Thr Pro Gly Gln Gly Leu
    50                  55                  60

Glu Trp Ile Gly Ala Ile Tyr Pro Gly Asn Gly Asp Thr Ser Tyr Asn
65                  70                  75                  80

Gln Lys Phe Lys Gly Lys Ala Thr Leu Thr Ala Asp Lys Ser Ser Ser
                85                  90                  95

Thr Ala Tyr Met Gln Leu Ser Ser Leu Thr Ser Glu Asp Ser Ala Val
                100                 105                 110

Tyr Tyr Cys Ala Arg Ser His Tyr Gly Ser Asn Tyr Val Asp Tyr Phe
                115                 120                 125

Asp Tyr Trp Gly Gln Gly Thr Thr Leu Thr Val Ser Ser Ala Lys Thr
            130                 135                 140

Thr Ala Pro Ser Val Tyr Pro Leu Ala Pro Val Cys Gly Asp Thr Thr
145                 150                 155                 160

Gly Ser Ser Val Thr Leu Gly Cys Leu Val Lys Gly Tyr Phe Pro Glu
                165                 170                 175

Pro Val Thr Leu Thr Trp Asn Ser Gly Ser Leu Ser Ser Gly Val His
            180                 185                 190

Thr Phe Pro Ala Val Leu Gln Ser Asp Leu Tyr Thr Leu Ser Ser Ser
        195                 200                 205

Val Thr Val Thr Ser Ser Thr Trp Pro Ser Gln Ser Ile Thr Cys Asn
    210                 215                 220

Val Ala His Pro Ala Ser Ser Thr Lys Val Asp Lys Lys Ile Glu Pro
225                 230                 235                 240

Arg Gly Pro Thr Ile Lys Pro Cys Pro Pro Cys Lys Cys Pro Ala Pro
                245                 250                 255

Asn Leu Leu Gly Gly Pro Ser Val Phe Ile Phe Pro Pro Lys Ile Lys
                260                 265                 270

Asp Val Leu Met Ile Ser Leu Ser Pro Ile Val Thr Cys Glu Asn Pro
            275                 280                 285

Tyr His Ala Arg Arg Gly Ile Lys Glu His Val Ile Thr Cys Val Val
            290                 295                 300

Val Asp Val Ser Glu Asp Asp Pro Asp Val Gln Ile Ser Trp Phe Val
305                 310                 315                 320

Asn Asn Val Glu Val His Thr Ala Gln Thr Gln Thr His Arg Glu Asp
                325                 330                 335

Tyr Asn Ser Thr Leu Arg Val Val Ser Ala Leu Pro Ile Gln His Gln
                340                 345                 350

Asp Trp Met Ser Gly Lys Glu Phe Lys Cys Lys Val Asn Asn Lys Asp
            355                 360                 365

Leu Pro Ala Pro Ile Glu Arg Thr Ile Ser Lys Pro Lys Gly Ser Val
    370                 375                 380

Arg Ala Pro Gln Val Tyr Val Leu Pro Pro Glu Glu Glu Met Thr
385                 390                 395                 400

Lys Lys Gln Val Thr Leu Thr Cys Met Val Thr Asp Phe Met Pro Glu
                405                 410                 415

Asp Ile Tyr Val Glu Trp Thr Asn Asn Gly Lys Thr Glu Leu Asn Tyr
            420                 425                 430

Lys Asn Thr Glu Pro Val Leu Asp Ser Asp Gly Ser Tyr Phe Met Tyr
        435                 440                 445

```
Ser Lys Leu Arg Val Glu Lys Lys Asn Trp Val Glu Arg Asn Ser Tyr
    450                 455                 460

Ser Cys Ser Val Val His Glu Gly Leu His Asn His His Thr Thr Lys
465                 470                 475                 480

Ser Phe Ser Arg Thr Pro Gly Lys
            485

<210> SEQ ID NO 37
<211> LENGTH: 372
<212> TYPE: DNA
<213> ORGANISM: Mus musculus

<400> SEQUENCE: 37
caggtgcagc tgcagcagtc tggggctgag ctggtgaggc ctgggtcctc agtgaagatt      60
tcctgcaagg cttctggcta tgcattcagt agctactgga tgaactgggt gaagcagagg     120
cctggacagg gtcttgagtg gattggacag atttggcctg agatggtga tactaactac      180 aatgaaagt tcaagggtaa agccactctg actgcagacg aatcctccag cacagcctac      240
atgcaactca gcagcctagc atctgaggac tctgcggtct atttctgtgc aagacgggag     300
actacgacgg taggccgtta ttactatgct atggactact ggggtcaagg aacctcagtc     360
accgtctcct ca                                                         372

<210> SEQ ID NO 38
<211> LENGTH: 336
<212> TYPE: DNA
<213> ORGANISM: Mus musculus

<400> SEQUENCE: 38
gatatcttgc tcacccaaac tccagcttct ttggctgtgt ctctagggca gagggccacc      60
atctcctgca aggccagcca agtgttgat tatgatggtg atagttattt gaactggtac      120
caacagattc caggacagcc acccaaactc ctcatctatg atgcatccaa tctagtttct     180
gggatcccac ccaggtttag tggcagtggg tctgggacag acttcaccct caacatccat     240
cctgtggaga aggtggatgc tgcaacctat cactgtcagc aaagtactga ggatccgtgg     300
acgttcggtg gaggcaccaa gctggaaatc aaacgg                              336

<210> SEQ ID NO 39
<211> LENGTH: 348
<212> TYPE: DNA
<213> ORGANISM: Mus musculus

<400> SEQUENCE: 39
caggtccagc tgcaggagtc aggggctgaa ctgtcaaaac ctggggcctc agtgaagatg      60
tcctgcaagg cttctggcta cacctttact agctactggc tgcactggat aaaacagagg     120
cctggacagg gtctggaatg gattggatac attaatccta ggaatgatta tactgagtac     180
aatcagaact tcaaggacaa ggccacattg actgcagaca atcctccag cacagcctac      240 atgcaactga gcagcctgac atctgaggac tctgcagtct attactgtgc aagaagggat     300
attactacgt tctactgggg ccaaggcacc actctcacag tctcctcg                  348

<210> SEQ ID NO 40
<211> LENGTH: 300
<212> TYPE: DNA
<213> ORGANISM: Mus musculus

<400> SEQUENCE: 40
```

-continued

```
gatatccagc tgacccagtc tccatcatct ctggctgtgt ctgcaggaga aaacgtcact    60
atgagctgta agtccagtca aagtgtttta tacagtgcaa atcacaagaa ctacttggcc   120
tggtaccagc agaaaccagg gcagtctcct aaactgctga tctactgggc atccactagg   180
gaatctggtg tccctgatcg cttcacaggc agcggatctg ggacagattt tactcttacc   240
atcagcagag tacaagttga agacctggca atttattatt gtcaccaata cctctcctcg   300
```

<210> SEQ ID NO 41
<211> LENGTH: 366
<212> TYPE: DNA
<213> ORGANISM: Mus musculus

<400> SEQUENCE: 41

```
caggtgcaac tgcggcagcc tggggctgag ctggtgaagc ctggggcctc agtgaagatg    60
tcctgcaagg cttctggcta cacatttacc agttacaata tgcactgggt aaagcagaca   120
cctggacagg gcctggaatg gattggagct atttatccag gaaatggtga tacttcctac   180
aatcagaagt tcaaaggcaa ggccacattg actgcagaca atcctccag cacagcctac    240 atgcagctca gcagtctgac atctgaggac tctgcggtct attactgtgc aagatcgcac   300
tacggtagta actacgtaga ctactttgac tactggggcc aaggcaccac tctcacagtc   360
tcctca                                                              366
```

<210> SEQ ID NO 42
<211> LENGTH: 321
<212> TYPE: DNA
<213> ORGANISM: Mus musculus

<400> SEQUENCE: 42

```
caaattgttc tctcccagtc tccagcaatc ctttctgcat ctccagggga gaaggtcaca    60
atgacttgca gggccagctc aagtttaagt ttcatgcact ggtaccagca gaagccagga   120
tcctccccca aaccctggat ttatgccaca tccaacctgg cttctggagt ccctgctcgc   180
ttcagtggca gtgggtctgg gacctcttac tctctcacaa tcagcagagt ggaggctgaa   240
gatgctgcca cttatttctg ccatcagtgg agtagtaacc cgctcacgtt cggtgctggg   300
acaaagctgg aactcaaacg t                                             321
```

<210> SEQ ID NO 43
<211> LENGTH: 14
<212> TYPE: PRT
<213> ORGANISM: Human herpesvirus 4

<400> SEQUENCE: 43

```
Val Val Arg Met Phe Met Arg Glu Arg Gln Leu Pro Gln Ser
1               5                   10
```

B-CELL RECEPTOR COMPLEX BINDING PROTEINS CONTAINING T-CELL EPITOPES

CROSS-REFERENCE TO RELATED APPLICATIONS

This application is a divisional of U.S. patent application Ser. No. 14/386,275, filed Sep. 18, 2014, which is the U.S. National Phase of PCT/EP2013/055690, filed Mar. 19, 2013, which claims priority from European Patent Application No. 12160165.2, filed Mar. 19, 2012. The contents of these applications are incorporated herein by reference in their entirety.

The present invention relates to a polypeptide comprising a) a binding peptide binding to at least one protein selected from the group consisting of CD22, CD19, CD20, and CD21, and b) an immunogenic peptide comprising at least one T-cell epitope for use in vaccination of a subject against B-cell hyperproliferation or for use in the modulation of the immune response in a subject. The present invention further relates to a polynucleotide and a vector encoding said polypeptide and a host cell comprising the same. It also relates to a method for the stimulation of antigen-specific T-cells, comprising a) contacting antigen presenting cells (APC) with a polypeptide, the polynucleotide, or the vector of the invention, b) contacting said APC with T-cells, and c) thereby stimulating antigen-specific T-cells specific for said at least one T-cell epitope; to a method for immunizing a subject against B-cell hyperproliferation, to a method for immunizing a subject against an infectious agent, and to a method for inducing tolerance in a subject.

By immunization, a subject's immune system becomes fortified against an antigen. Especially the adaptive immune system, i.e. the part of the immune system that confers the capability of an individual's immune system to recognize, remember, and cope with potential pathogens, has been of strong medical interest (Kaech et al. (2002), Nature Reviews Immunology 2(4):251-62; Pulendran and Ahmed (2006), Cell 124(4):849-63). On the one hand, it has been extensively exploited in vaccination to confer immunity to otherwise potentially deadly disease. It has also been used with variable success to eliminate cancer cells through recognition of tumor antigens. On the other hand, attenuation of the adaptive immune system is of interest in diseases where a strong immune response is inappropriate, like e.g. in allergy, asthma, or autoimmune disease.

Despite the overall success of vaccination, there are several disease-causing agents, like viruses (e.g. human immunodeficiency virus, Epstein-Barr virus), Bacteria (e.g. *Staphylococcus* spec., Borellia spec.), eukaryotic pathogens (e.g. *Trypanosoma* spec.), but also cancer cells, that have escaped from becoming amenable for vaccination. The reasons for this are complex and depend to a large extent on the nature of the specific agent, but also on the physiological state of the individual to be vaccinated. For some disease-causing agents, methods to fortify the immune response during vaccination, like the use of virus-like particles instead of soluble antigen, inclusion of adjuvants, use of live vaccines, and the like, have been devised. It has also been proposed to boost the immune response by delivering suitable epitopes, which are typically peptides, to the professional antigen presenting cells, i.e. macrophages, dendritic cells, and B-cell s.

The principal role of B-cells in the immune system is the production of antigen-specific antibodies upon their activation. Activation requires that the B-cell-receptor (BCR) on the surface of the B-cell becomes bound to its cognate antigen. This activation of the BCR leads to activation of the B-cell, which undergoes maturation and clonal expansion, after which part of the cells produced this way becomes plasma cells producing antibodies specific for said antigen. The BCR mediates this activation; it consists of a membrane-bound antibody molecule specifically able to recognize one antigenic structure, along with several co-receptors, including CD21 and CD19. Two other surface molecules of the B-cell, CD20 and CD22, are known to—at least temporarily—interact with the BCR and act as positive and negative regulators, respectively. Thus, they can be considered as being members of the BCR complex (BCRC) in a wider sense. Common to all four molecules is their internalization into cytoplasmic vesicles and their fusion with the endosome upon ligand binding.

Another important branch of the adaptive immune system are epitope-specific T-cells. In humans, these cells have a T-cell-receptor on their surface, the recognition domain of which is specific for a defined complex between an antigenic peptide (T-cell epitope) and a major histocompatibility complex (MHC) protein. If the T-cell-receptor is engaged in a cognate interaction, the T-cell becomes activated, multiplies, and performs its activatory or inhibitory task in the immune response.

The MHC molecules come in two forms: MHC class I are expressed on the surface of every human cell and present, essentially randomly, peptides derived from proteins present in the cell's cytosol; they, thus, give a continuous overview of the protein repertoire of the cell and allow for recognition of non-normal protein expression, e.g. during viral infection of the cell or in carcinogenesis. In order to recognize MHC class I molecule—peptide complexes, the T-cell receptor requires the CD8 surface protein as a co-receptor. There is thus a subclass of T-cells expressing the CD8 co-receptor, named CD8+-T-cells; their main but not exclusive function is to eliminate body cells presenting peptides that indicate potential pathogenic processes in said cell, e.g. virus infection, which is why they are also called cytotoxic T-cells.

MHC class II are expressed only on professional antigen presenting cells (APCs). On these, peptides are presented that are derived from proteins that were ingested by the APCs, mainly by endocytosis. Recognition of MHC class II requires the coreceptor CD4, which is expressed only on the surface of CD4+ T-cells. The primary role of these T-cells, also called T-helper cells, is the activation of CD8+-T-cells, macrophages, and B-cells. Delivery of suitable epitopes to APCs thus leads to presentation of these epitopes via MHC class II to helper T-cells, which in turn activates these T-cells and leads to the activation of the other branches of the immune system. Importantly, experimental evidence exists that co-engagement of the CD19/CD21 complex results in more rapid and efficient production of antigenic peptide/class II complexes as compared with engagement of the B cell receptor alone by the antigen (Fearon D T et al. (2000), Annu Rev Immunol 18:393-422).

Methods used so far to deliver epitopes to APCs have included incubation of APCs with soluble antigens, infection with live attenuated micro-organisms, infection with viral vectors derived from vaccinia or other viruses, and injection of DNA vaccines. Results with these methods were, however, not satisfactory in all cases.

Also, depletion or inhibition of APCs, especially B-cells, has been used to attenuate the adaptive immune response in diseases where there is an overreaction (e.g. allergy) or misdirected reaction (e.g. autoimmune disease). However, with the current treatments available, these diseases in many cases cannot be treated satisfactorily.

There is thus still an existing need for improved vaccines and other immune modulators. The technical problem underlying the invention can be seen as the provision of means and methods which allow for improved vaccination and immune modulation. The technical problem is solved by the embodiments characterized in the claims and herein below.

Therefore, the present invention relates to a polypeptide comprising a) a binding peptide binding to at least one protein selected from the group consisting of CD21, CD19 CD20, and CD22, and b) an immunogenic peptide comprising at least one T-cell epitope for the use in modulation of the immune response in a subject.

As used in this specification, the term "polypeptide" relates to any chemical molecule comprising at least a binding peptide and at least one immunogenic peptide as specified herein below. It is to be understood that the chemical linkage between the binding peptide and the immunogenic peptide(s) need not necessarily be a peptide bond. It is also envisaged by the present invention that the chemical bond between the binding peptide and the immunogenic peptide(s) is an ester bond, a disulfide bond, or any other suitable covalent chemical bond known to the skilled artisan. Also envisaged are non-covalent bonds with a dissociation constant so low that the immunogenic peptide(s) will only dissociate to a negligible extent from the binding peptide. Preferably, the dissociation constant for said non-covalent bond is less than $10^{-5}$ mol/l (as it is the case with the Strep-Tag: Strep-Tactin binding), less than $10^{-6}$ mol/l (as it is the case in the Strep-TagII: Strep-Tactin binding), less than $10^{-8}$ mol/l, less than $10^{-10}$ mol/l, or less than $10^{-12}$ mol/l (as it is the case for the Streptavidin: Biotin binding). Methods of determining dissociation constants are well known to the skilled artisan and include, e.g., spectroscopic titration methods, surface plasmon resonance measurements, equilibrium dialysis and the like. Preferably, the chemical linkage between the binding peptide and the immunogenic peptide(s) is a peptide bond, i.e. the polypeptide is a fusion polypeptide comprising or consisting of the binding peptide and the immunogenic peptide of the present invention. Preferably, the polypeptide does not comprise one or more peptide sequences known to inhibit antigen presentation. Moreover, preferably, the polypeptide does not comprise genetic material, i.e. polynucleotides. In a preferred embodiment, the polypeptide consists of the components as described herein.

The term "binding peptide" as used herein relates to any peptide binding to at least one protein of the B-cell receptor complex (BCRC), wherein the proteins of the BCRC, preferably, are CD21, CD19 CD20, and CD22, with an affinity that permits internalization of said binding peptide by a B-cell. Preferably, the dissociation constant for the binding of said binding peptide to said protein of the B-cell receptor complex of less than $10^{-5}$ mol/l, less than $10^{-6}$ mol/l, less than $10^{-7}$ mol/l, less than $10^{-8}$ mol/l, or less than $10^{-9}$ mol/l. Preferably, the binding peptide is a peptide from the N-terminus of the Epstein-Barr virus (EBV, also referred to as Human Herpesvius 4) glycoprotein gp350/220 (gp350, gene: SEQ ID NO: 1, Genbank Acc No: NC_009334.1 GI:139424470, protein product SEQ ID NO: 2, Genbank Acc No: YP_001129462.1 GI:139424497), more preferably the binding peptide comprises the first 470 amino acids of the EBV gp350 or another CD21-binding peptide of EBV gp350. In another preferred embodiment, the binding peptide is an antibody binding to at least one of the B-cell receptor complex proteins (BCRC proteins) specified above.

Preferred binding peptides are:
- a mouse anti-human CD21 antibody, comprising a heavy chain (SEQ ID NO: 25) encoded by Genbank Acc No: GQ850526.1 GI: 282721923, SEQ ID No. 13, and comprising a light chain (SEQ ID NO: 26) encoded by Genbank Acc No: GQ850527.1 GI: 282721925, SEQ ID No. 14;
- a mouse anti-human CD19 antibody, comprising a heavy chain variable fragment encoded by Genbank Acc No: X99230.1 GI: 1435158, SEQ ID NO: 37 (e.g. the heavy chain of SEQ ID NO: 27, encoded by SEQ ID No. 15), and comprising a light chain variable fragment encoded by Genbank Acc No: X99232.1 GI: 1435165, SEQ ID NO: 38 (e.g. the light chain of SEQ ID NO: 28, encoded by SEQ ID No. 16);
- a mouse anti-human CD22 antibody, comprising a heavy chain variable fragment encoded by Genbank Acc No: 577347 GI: 998423, SEQ ID NO: 39 (e.g. the heavy chain of SEQ ID NO: 29, encoded by SEQ ID No. 17) and comprising a light chain variable fragment encoded by Genbank Acc No: 577340 GI: 998421, SEQ ID NO: 40 (e.g. the light chain of SEQ ID NO: 30, encoded by SEQ ID No. 18);
- a mouse anti-human CD20 antibody, comprising a heavy chain variable fragment encoded by Genbank Acc No: AY058907.1 GI: 16902039, SEQ ID NO:41 (e.g. the heavy chain of SEQ ID NO: 31 encoded by SEQ ID NO: 19) and comprising a light chain variable fragment encoded by Genbank Acc No: AY058906.1 GI: 16902037, SEQ ID NO: 42 (e.g. the light chain of SEQ ID NO: 32 encoded by SEQ ID NO: 20).

As used herein, the term "antibody" relates to a soluble immunoglobulin from any of the classes IgA, IgD, IgE, IgG, or IgM. Antibodies against the BCRC proteins can be prepared by well known methods using a purified protein or a suitable fragment derived therefrom as an antigen. A fragment which is suitable as an antigen may be identified by antigenicity determining algorithms well known in the art. Such fragments may be obtained either from the polypeptide of the invention by proteolytic digestion or may be a synthetic peptide. Preferably, the peptide suitable as an antigen is located at the exterior of the B-cell in its natural context. Preferably, the antibody of the present invention is a monoclonal antibody, a polyclonal antibody, a human or humanized antibody or primatized, chimerized or fragment thereof. More preferably, the antibody is a single chain antibody. Also comprised as antibodies of the present invention are a bispecific antibody, a synthetic antibody, an antibody fragment, such as Fab, Fv or scFv fragments etc., or a chemically modified derivative of any of these. Preferably, the antibody of the present invention shall specifically bind (i.e. does not cross react with other polypeptides or peptides) to the BCRC protein of the invention. Specific binding can be tested by various well known techniques. Antibodies or fragments thereof can be obtained by using methods which are described, e.g., in Harlow and Lane "Antibodies, A Laboratory Manual", CSH Press, Cold Spring Harbor, 1988. Monoclonal antibodies can be prepared by the techniques originally described in Köhler and Milstein (1975), Nature 256, 495; and Galfré (1981), Meth. Enzymol. 73, 3, which comprise the fusion of mouse myeloma cells to spleen cells derived from immunized mammals.

Preferably, the binding peptide is contiguous in amino acid sequence with the immunogenic peptide, i.e. the binding peptide and the immunogenic peptide form a fusion polypeptide. More preferably, the fusion polypeptide comprises an immunogenic peptide fused to a heavy chain or a light chain of an antibody. Most preferably, the fusion polypeptide comprises an immunogenic peptide from EBV EBNA3C fused to a heavy chain of a mouse antibody binding to a BCRC protein, e.g. the fusion protein of SEQ ID NO: 33 (anti-CD21 heavy chain fused to EBNA3C-5H11 epitope, encoded by SEQ ID NO: 21), SEQ ID NO: 34 (anti-CD19 heavy chain fused to EBNA3C-5H11 epitope, encoded by SEQ ID NO: 22), SEQ ID NO: 35 (anti-CD22 heavy chain fused to EBNA3C-5H11 epitope, encoded by SEQ ID NO: 23), or SEQ ID NO: 36 (anti-CD20 heavy chain fused to EBNA3C-5H11 epitope, encoded by SEQ ID NO: 24). It is, however, also envisaged by the present invention that, preferably, the binding peptide is contiguous in amino acid sequence with an adapter molecule binding the immunogenic peptide as described herein above. It is clear for the person skilled in the art that in such case the immunogenic peptide preferably comprises an adapter molecule suited to bind, covalently or non-covalently, to the adapter molecule fused to the binding peptide, e.g., preferably, the binding peptide is fused to a Strep-Tag and the immunogenic peptide is fused to Strep-Tactin.

The term "CD21" as used herein relates to the human cluster of differentiation protein 21, also known as complement receptor 2 (CR2) (Transcript variant 1: SEQ ID NO: 3, Genbank Acc No: NM_001006658.2 GI:260099695, protein product SEQ ID NO: 4, Genbank Acc No: NP_001006659.1 GI:54792123; Transcript variant 2: SEQ ID NO: 5, Genbank Acc. NM_001877.4 GI:260099700, protein product SEQ ID NO: 6, Genbank Acc No: NP_001868.2 GI:42544177). The term "CD19" relates to the human cluster of differentiation protein 19 (transcript SEQ ID NO: 7, Genbank Acc No: NM_001178098.1 GI:296010920; protein product SEQ ID NO: 8, Genbank Acc No: NP_001171569.1 GI:296010921). The term "CD20" relates to the human cluster of differentiation protein 20 (transcript SEQ ID NO: 9, Genbank Acc No: NM_152866.2 GI:68348720; protein product SEQ ID NO: 10, Genbank Acc No: NP_068769.2 GI:23110987). The term "CD22" relates to the human cluster of differentiation protein 22 (Transcript SEQ ID NO: 11, Genbank Acc No: NM_001771.3 GI:297374826, protein product SEQ ID NO: 12, Genbank Acc No: NP_001762.2 GI:157168355). It is envisaged by the present invention that the terms for the BCRC proteins CD21, CD19, CD 20, and CD22 shall also include homologs, orthologs, and naturally occurring variants (e.g. variants translated from splice variants) of the respective proteins in mammals.

The term "immunogenic peptide" as used herein relates to a peptide comprising at least one T-cell epitope. A T-cell epitope, as is known to the one skilled in the art, is a contiguous sequence of amino acids comprised in a peptide, which can be bound to a major histocompatibility complex (MHC) class I or class II molecule to be presented on the surface of a cell (MHC-I) or of a professional antigen presenting cell (MHC-II). The skilled artisan knows how to predict immunogenic peptides presented on MHC-I or MHC-II (Nielsen et al., (2004), Bioinformatics, 20 (9), 1388-1397), Bordner (2010), PLoS ONE 5(12): e14383) and how to evaluate binding of specific peptides (e.g. Bernardeau et al., (2011), J Immunol Methods, 371(1-2):97-105). Preferably, the T-cell epitope is an MHC-II epitope. Preferably, the T-cell epitope is an epitope derived from a tumor antigen, i.e. an amino acid sequence comprised in a protein expressed essentially only in or on a tumor cell. In a preferred embodiment, the T-cell epitope is an epitope derived from a B-cell lymphoma tumor antigen. More preferably, the T-cell epitope is an epitope derived from a latent gene product of EBV. Most preferably, the T-cell epitope is an amino acid sequence comprised in one of the latent gene products of EBV known or suspected to contribute to cell transformation, i.e. one of the EBV EBNA2, LMP1, EBNA3A, -B and -C proteins (Long et al. (2011), Curr Opin Immunol 23(2):258-64). In a preferred embodiment, the T-cell epitope is a strong T-cell epitope as detailed herein below.

The term "modulation of the immune response", as used in this specification, relates to inducing a change in the response of a subject's adaptive immune system by applying a polypeptide of the present invention. The modulation may be an activation, i.e. lead to an enhanced response to the T-cell epitope(s); or the modulation may be a repression, i.e. lead to a decreased response, e.g. tolerance, to the T-cell epitope(s). The modulation of immune response, preferably, effects amelioration of a disorder or disease or of symptoms accompanied therewith to a significant extent in a subject, or, also preferably, modulation of immune response effects retaining health with respect to disease or disorder for a certain period of time in a subject. Said effect of modulation of immune response as used herein also includes an entire restoration of the health with respect to the disease or disorder. It is to be understood that modulation of immune response as used in accordance with the present invention may not be effective in all subjects to be treated. However, the term shall require that a statistically significant portion of subjects suffering from a disease or disorder can be successfully treated or that a statistically significant portion of subjects of a cohort or population are effectively prevented from suffering from a disease or disorder or its accompanying symptoms. Whether a portion is statistically significant can be determined without further ado by the person skilled in the art using various well known statistic evaluation tools, e.g., determination of confidence intervals, p-value determination, Student's t-test, Mann-Whitney test etc. Preferred confidence intervals are at least 90%, at least 95%, at least 97%, at least 98% or at least 99%. The p-values are, preferably, 0.1, 0.05, 0.01, 0.005, or 0.0001. Preferably, the modulation of immune response shall be effective for at least 60%, at least 70%, at least 80%, or at least 90% of the subjects of a given cohort or population. Preferably, the modulation of the immune response is a vaccination against an infectious agent, vaccination against B-cell hyperproliferation, or induction of tolerance to an antigen causing autoimmune disease.

The term "infectious agent", as used herein, preferably relates to a microorganism causing disease in a subject. Preferably, the infectious agent is a bacterium, an eukaryotic infectious agent, e.g. a *Plasmodium* spp., more preferably a virus, e.g. a Hepatitis virus or Human Immunodeficiency Virus (HIV). In a preferred embodiment, the infectious agent is an agent causing chronic disease. More preferably, the infectious agent is an agent causing chronic and/or persisting infection. Still more preferably, the infectious agent is an agent causing chronic and/or persisting infection by modulation of least one antigenic determinant of said infectious agent. Most preferably, at least five, at least ten, at least fifteen, at least twenty modulated forms of the aforesaid antigenic determinants are known, preferably known to occur in a body of a subject. In a further preferred embodiment, the aforesaid modulated antigenic determinant is a polypeptide.

As used herein, the term "B-cell hyperproliferation" relates to an increased proliferation of B-cells as compared to normal. Preferably, B-cell hyperproliferation is EBV-associated diseases including infectious mononucleosis or post-transplant lymphoproliferative disorder (PTLD), or B-cell lymphoma.

As used herein, the term "inducing tolerance" relates to inducing a decreased response to an immunogenic peptide in a subject. Preferably, tolerance is induced in subjects suffering from or being at risk to suffer from an autoimmune disease. Also preferably, tolerance is induced to immunogenic peptides, the immune response against which is known to aggravate said autoimmune disease. Preferred autoimmune diseases are Multiple Sclerosis, Rheumatoid Arthritis, or Autoimmune Thyroiditis, or other autoimmune diseases for which immunoreactive T cell epitopes have been identified.

In further preferred embodiments, the present invention relates to a pool of polypeptides as defined herein below, a pool of polynucleotides as defined herein below, and to a pool of vectors as defined herein below.

The kind of modulation achieved by application of the polypeptide of the present invention depends on several factors: The type of APC has a marked influence on the outcome of the immune response; resting B lymphocytes typically induce tolerance whereas dendritic cells and activated B blasts such as immunoblasts induce activation. Therefore, targeting of activated B cells such as B cell lymphoma leads to T cell recognition and eventually to their elimination. In contrast targeting of resting B cells with an auto antigen leads to its tolerance. The dose of delivered antigens also plays an important role; very low and high amounts of antigens tend to induce tolerance, intermediate amounts lead to T cell activation. Furthermore, the immunostimulatory effects of antibodies or polypeptides that target CD19, CD21 or CD20 or in contrast the B immunosuppressive effects of antibodies directed towards CD22 will also influence the outcome of the antigen delivery.

The term "subject" relates to an animal, preferably a mammalian organism, with the capacity to generate an immune response to molecules foreign to the organism and comprising at least one BCRC protein. More preferably, the subject is a cattle, pig, sheep, horse, cat dog, mouse, or rat, most preferably a human being.

The definitions made above apply mutatis mutandis to the following:

The present invention also relates to a polynucleotide encoding a binding peptide covalently connected to the immunogenic peptide or with an adapter binding the immunogenic peptide.

The term "polynucleotide" as used in accordance with the present invention, preferably, relates to a polynucleotide comprising a nucleic acid sequence which encodes a fusion polypeptide comprising a binding peptide and an immunogenic peptide as specified herein above, or which encodes a fusion polypeptide comprising a binding peptide and an adapter peptide as specified herein above. Suitable assays for measuring the activities of the binding peptide and the immunogenic peptide mentioned before are described in the accompanying examples or in (Adhikary et al. (2006), J. Exp. Med. 203(4):995-1006; Busse et al. (2010), J. Virology 84(2):1139-47; Gurer et al. (2008), Blood 112(4):1231-9). A polynucleotide encoding a fusion polypeptide comprising the aforementioned peptides has been obtained in accordance with the present invention by cloning immunogenic peptides into polypeptides specifically binding proteins of the BCRC using well known techniques.

Thus, the polynucleotide, preferably, comprises the nucleic acid sequence shown in SEQ ID NO: 21-24 encoding the polypeptide having an amino acid sequence as shown in SEQ ID NO: 33-36. It is to be understood that a polypeptide having an amino acid sequence as shown in SEQ ID NO: 21-24 may be also encoded due to the degenerated genetic code by other polynucleotides as well.

Moreover, the term "polynucleotide" as used in accordance with the present invention further encompasses variants of the aforementioned specific polynucleotides. The polynucleotide variants, preferably, comprise a nucleic acid sequence characterized in that the sequence can be derived from the aforementioned specific nucleic acid sequences shown in SEQ ID NO: 21-24 by at least one nucleotide substitution, addition and/or deletion whereby the variant nucleic acid sequence shall still encode a polypeptide comprising the activities as specified above. Variants include polynucleotides comprising nucleic acid sequences which are at least 70%, at least 75%, at least 80%, at least 85%, at least 90%, at least 95%, at least 98% or at least 99% identical to the nucleic acid sequences shown in SEQ ID NO: 21-24. Moreover, also encompassed are polynucleotides which comprise nucleic acid sequences encoding amino acid sequences which are at least 70%, at least 75%, at least 80%, at least 85%, at least 90%, at least 95%, at least 98% or at least 99% identical to the amino acid sequences shown in SEQ ID NO: 33-36. The percent identity values are, preferably, calculated over the entire amino acid or nucleic acid sequence region. A series of programs based on a variety of algorithms is available to the skilled worker for comparing different sequences. In this context, the algorithms of Needleman and Wunsch or Smith and Waterman give particularly reliable results. To carry out the sequence alignments, the program PileUp (J. Mol. Evolution., 25, 351-360, 1987, Higgins et al., CABIOS, 5 1989: 151-153) or the programs Gap and BestFit [Needleman and Wunsch (J. Mol. Biol. 48; 443-453 (1970)) and Smith and Waterman (Adv. Appl. Math. 2; 482-489 (1981))], which are part of the GCG software packet [Genetics Computer Group, 575 Science Drive, Madison, Wis., USA 53711 (1991)], are to be used. The sequence identity values recited above in percent (%) are to be determined, preferably, using the program GAP over the entire sequence region with the following settings: Gap Weight: 50, Length Weight: 3, Average Match: 10.000 and Average Mismatch: 0.000, which, unless otherwise specified, shall always be used as standard settings for sequence alignments.

A polynucleotide comprising a fragment of any of the aforementioned nucleic acid sequences is also encompassed as a polynucleotide of the present invention. The fragment shall encode a polypeptide which still has the activity as specified above. Accordingly, the polypeptide may comprise or consist of the peptides of the present invention conferring the said biological activities. A fragment as meant herein, preferably, comprises at least 50, at least 100, at least 250 or at least 500 consecutive nucleotides of the aforementioned nucleic acid sequence or encodes an amino acid sequence comprising at least 20, at least 30, at least 50, at least 80, at least 100 or at least 150 consecutive amino acids of the aforementioned amino acid sequence.

The polynucleotides of the present invention either essentially consist of the aforementioned nucleic acid sequences or comprise the aforementioned nucleic acid sequences. Thus, they may contain further nucleic acid sequences as well. Specifically, the polynucleotides of the present invention may encode fusion proteins wherein one partner of the fusion protein is a polypeptide being encoded by a nucleic acid sequence recited above. Such fusion proteins may comprise as additional part other polypeptides for monitoring expression (e.g., green, yellow, blue or red fluorescent proteins, alkaline phosphatase and the like) or so called "tags" which may serve as a detectable marker or as an auxiliary measure for purification purposes. Tags for the different purposes are well known in the art and comprise FLAG-tags, 6-histidine-tags, MYC-tags and the like.

The polynucleotide of the present invention shall be provided, preferably, either as an isolated polynucleotide (i.e. isolated from its natural context) or in genetically modified form. The polynucleotide, preferably, is DNA including cDNA or RNA. The term encompasses single as well as double stranded polynucleotides. Moreover, comprised are also chemically modified polynucleotides including naturally occurring modified polynucleotides such as glycosylated or methylated polynucleotides or artificial modified one such as biotinylated polynucleotides.

The present invention further relates to a vector comprising the polynucleotide of the present invention.

The term "vector", preferably, encompasses phage, plasmid, viral or retroviral vectors as well as artificial chromosomes, such as bacterial or yeast artificial chromosomes. Moreover, the term also relates to targeting constructs which allow for random or site-directed integration of the targeting construct into genomic DNA. Such target constructs, preferably, comprise DNA of sufficient length for either homologous or heterologous recombination as described in detail below. The vector encompassing the polynucleotides of the present invention, preferably, further comprises selectable markers for propagation and/or selection in a host. The vector may be incorporated into a host cell by various techniques well known in the art. For example, a plasmid vector can be introduced in a precipitate such as a calcium phosphate precipitate or rubidium chloride precipitate, or in a complex with a charged lipid or in carbon-based clusters, such as fullerens. Alternatively, a plasmid vector may be introduced by heat shock or electroporation techniques. Should the vector be a virus, it may be packaged in vitro using an appropriate packaging cell line prior to application to host cells. Retroviral vectors may be replication competent or replication defective. In the latter case, viral propagation generally will occur only in complementing host/ cells.

More preferably, in the vector of the invention the polynucleotide is operatively linked to expression control sequences allowing expression in prokaryotic or eukaryotic cells or isolated fractions thereof. Expression of said polynucleotide comprises transcription of the polynucleotide, preferably into a translatable mRNA. Regulatory elements ensuring expression in eukaryotic cells, preferably mammalian cells, are well known in the art. They, preferably, comprise regulatory sequences ensuring initiation of transcription and, optionally, poly-A signals ensuring termination of transcription and stabilization of the transcript. Additional regulatory elements may include transcriptional as well as translational enhancers. Possible regulatory elements permitting expression in prokaryotic host cells comprise, e.g., the lac, trp or tac promoter in E. coli, and examples for regulatory elements permitting expression in eukaryotic host cells are the AOX1 or GAL1 promoter in yeast or the CMV-, SV40-, RSV-promoter (Rous sarcoma virus), CMV-enhancer, SV40-enhancer or a globin intron in mammalian and other animal cells. Moreover, inducible expression control sequences may be used in an expression vector encompassed by the present invention. Such inducible vectors may comprise tet or lac operator sequences or sequences inducible by heat shock or other environmental factors. Suitable expression control sequences are well known in the art. Beside elements which are responsible for the initiation of transcription such regulatory elements may also comprise transcription termination signals, such as the SV40-poly-A site or the tk-poly-A site, downstream of the polynucleotide. In this context, suitable expression vectors are known in the art such as Okayama-Berg cDNA expression vector pcDV1 (Pharmacia), pBluescript (Stratagene), pCDM8, pRc/CMV, pcDNA1, pcDNA3 (InVitrogene) or pSPORT1 (GIBCO BRL). Preferably, said vector is an expression vector and a gene transfer or targeting vector. Expression vectors derived from viruses such as retroviruses, vaccinia virus, adeno-associated virus, herpes viruses, or bovine papilloma virus, may be used for delivery of the polynucleotides or vector of the invention into targeted cell population. Methods which are well known to those skilled in the art can be used to construct recombinant viral vectors; see, for example, the techniques described in Sambrook, Molecular Cloning A Laboratory Manual, Cold Spring Harbor Laboratory (1989) N.Y. and Ausubel, Current Protocols in Molecular Biology, Green Publishing Associates and Wiley Interscience, N.Y. (1994).

Preferably, the vector is a vector mediating expression of the polynucleotide of the present invention in a host cell. The skilled artisan knows how to select combinations of vectors and host cells for propagation of a vector and/or for expression of a protein encoded by the vector.

Furthermore, the present invention relates to a host cell comprising the polynucleotide or the vector of the present invention.

A "host cell", as used herein, relates to a bacterial, archaeal, or eukaryotic cell with the capacity to propagate the vector of the present invention and/or to produce a polypeptide encoded on the vector or the polynucleotide of the invention. Preferably, the host cell is a bacterial cell from the species Escherichia coli, a lepidopteran, a mouse, rat, or a human cell. Preferably, the host cell is a cell cultivated in vitro, more preferably a 293HEK cell. Also preferably, the host cell is an APC, more preferably a B-cell, most preferably an activated B-cell from a lymph node, a lymphoblastoid cell, a resting B-cell, or a neoplastic B cell, e.g. from a lymphoma.

The present invention contemplates a method for the stimulation of antigen-specific T-cells, comprising a) contacting antigen presenting cells (APC) with a polypeptide, the polynucleotide, or the vector of the present invention, b) contacting said APC with T-cells, and c) thereby stimulating antigen-specific T-cells specific for said at least one T-cell epitope.

The method of the present invention, preferably, is an in vitro method. Moreover, it may comprise steps in addition to those explicitly mentioned above. For example, further steps may relate, e.g., to isolating the antigen presenting cells (APC) for step a), or inclusion of T-cell stimulatory agents in step b).

The term "antigen", as used herein, relates to the protein chosen as the source of the T-cell epitope of the present invention. The term "antigen specific T-cells" relates to T-cells presenting on their surface T-cell receptor molecules specifically recognizing, i.e. binding to, the T-cell epitope of the present invention presented in the context of an MHC molecule. Preferably, the MHC molecule is an MHC class II molecule; thus, preferably, the T-cell is a CD4+ T-cell.

The term "contacting" as used in the context of the methods of the present invention is understood by the skilled person. Preferably, the term relates to bringing a polypeptide, a polynucleotide, a vector, or a cell of the present invention in physical contact with a subject or, preferably, a cell, i.e. allowing the aforementioned components to interact.

As used herein, the term "antigen presenting cell" or "APC" relates to a B-cell or a follicular dendritic cell expressing at least one of the BCRC proteins on its surface. Preferably, the APC is a B-cell, more preferably an activated B-cell from a lymph node, a lymphoblastoid cell, a resting B-cell, or a neoplastic B cell, e.g. from a lymphoma.

Furthermore encompassed by the present invention is a method for immunizing a subject against an infectious agent, comprising a) contacting said subject with a pool of polypeptides, polynucleotides, or vectors of the present invention, and b) thereby immunizing said subject against an infectious agent.

As used herein, the term "pool of polypeptides" relates to a collection of polypeptides according to the present invention comprising at least two, at least three, at least four, at least five, at least ten, at least 20, at least 50, at least 100 different immunogenic peptides selected from a library of immunogenic peptides found in patients with a long-standing infection with a specific infectious agent. The skilled artisan knows how to establish said library of immunogenic peptides (Reineke, U., et al. (2002) J. Immunol. Methods. 267(1):37-51; Milosevic, S., et al. (2006), J. Virol. 80(21): 10357-10364; Pedroza-Roldan, C., et al. (2009), 47:270-282). The terms "pool of polynucleotides" and "pool of vectors" are to be understood mutatis mutandis.

The present invention relates to a method for immunizing a subject against B-cell hyperproliferation, comprising a) contacting said subject with a polypeptide comprising a strong T-cell epitope as an immunogenic peptide, with a polynucleotide of the present invention comprising a sequence encoding a strong T-cell epitope, or with a vector of the present invention comprising a sequence encoding a strong T-cell epitope, and b) thereby immunizing said subject against B-cell hyperproliferation.

The term "strong T-cell epitope" relates to a T-cell epitope for which the probability that T-cells recognizing said T-cell epitope are present in a subject is high. Preferably, T-cells recognizing the strong T-cell epitope are present at a high frequency in a subject. Preferably, the T-cell epitopes are selected from the proteins of viruses commonly infecting said subject, or against which said subject has been vaccinated. More preferably, the strong T-cell epitopes are selected from viral proteins used for immunization. Most preferred strong T-cell epitopes are, for example, from EBV latent antigens such as the EBNA-3C 3H10 peptide (VVRMFMRERQLPQS, SEQ ID NO: 43).

The present invention also relates to a method for inducing tolerance in a subject, comprising a) contacting said subject with a tolerance-inducing polypeptide, with a polynucleotide encoding a tolerance-inducing polypeptide, or with a vector encoding a tolerance-inducing polypeptide, and b) thereby inducing tolerance in a subject.

The term "tolerance-inducing polypeptide", as used herein, relates to a polypeptide of the present invention inducing a decreased response to an immunogenic peptide in a subject. Preferably, the tolerance-inducing polypeptide comprises a binding peptide recognizing CD22 as a binding peptide, more preferably, the tolerance-inducing polypeptide is an anti-CD22 antibody fused to an immunogenic peptide.

All references cited in this specification are herewith incorporated by reference with respect to their entire disclosure content and the disclosure content specifically mentioned in this specification.

FIGURE LEGENDS

FIG. 1: T cell assay performed with EBV-transformed B cells (LCLs) used as antigen-presenting cells, pulsed with various amounts of antibodies fused with the 5H11 epitope from the EBV EBNA3C protein or with their respective heavy chain (HC). Antibodies tested are specific for CD21, CD19 and CD22. Positive controls include cells incubated with 5H11 peptide epitope, negative controls include anti-CD19, anti-CD21 or anti-CD22 antibodies devoid of antigens. Results are given in picograms IFN-gamma per ml.

Figure 2:
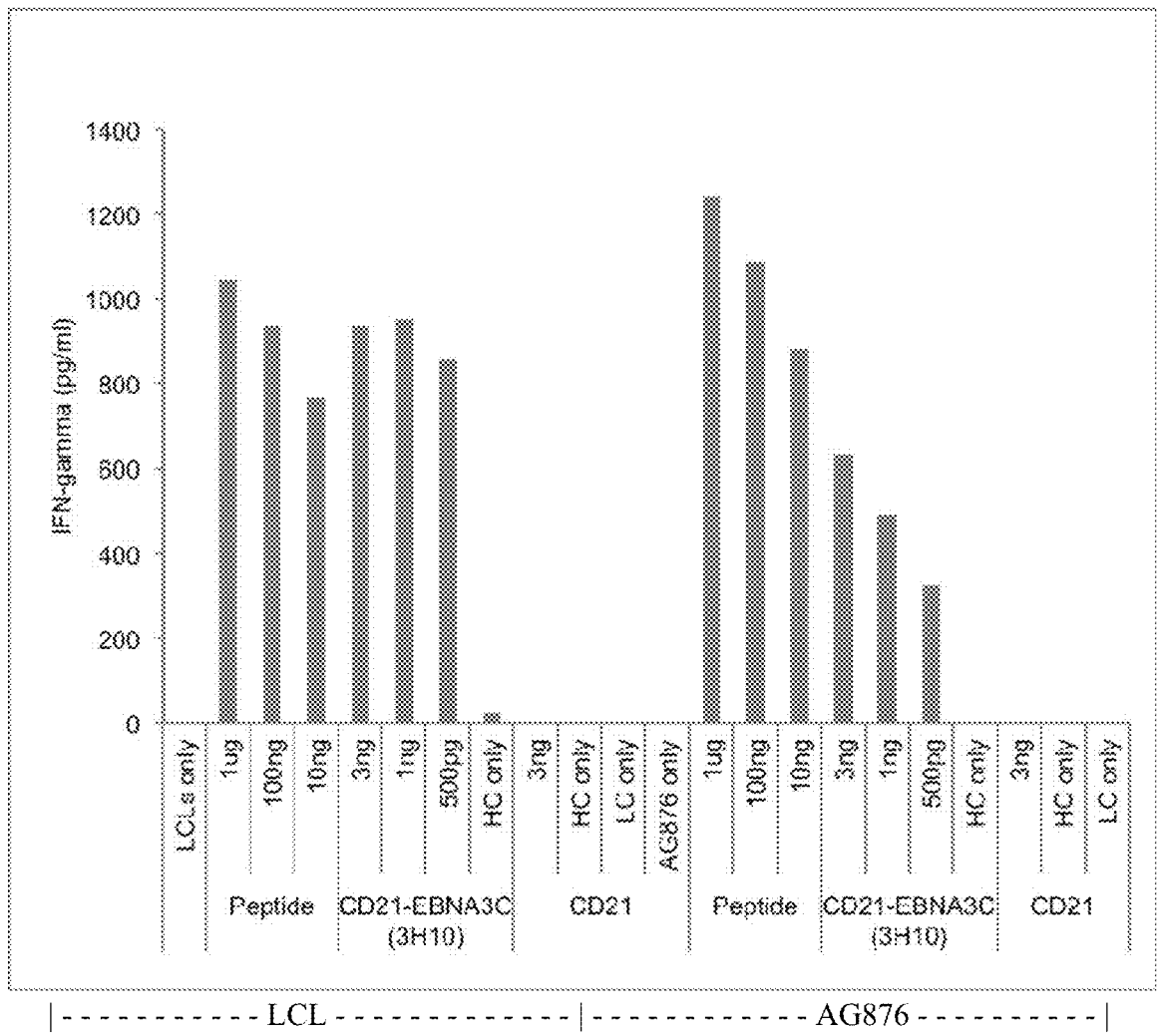

FIG. 2: T cell assay performed either with EBV-transformed B cells (LCLs) or the Burkitt's lymphoma cell line AG876 used as antigen-presenting cells, and pulsed with various amounts of CD21-specific antibodies fused with the 3H10 epitope from the EBV EBNA3C protein. Positive controls include cells incubated with 3H10 peptide epitope, negative controls anti-CD21 antibodies devoid of 3H10 or 3H10 anti-CD21 fusion proteins devoid of light chain. Results are given in picograms IFN-gamma per ml.

Figure 3:
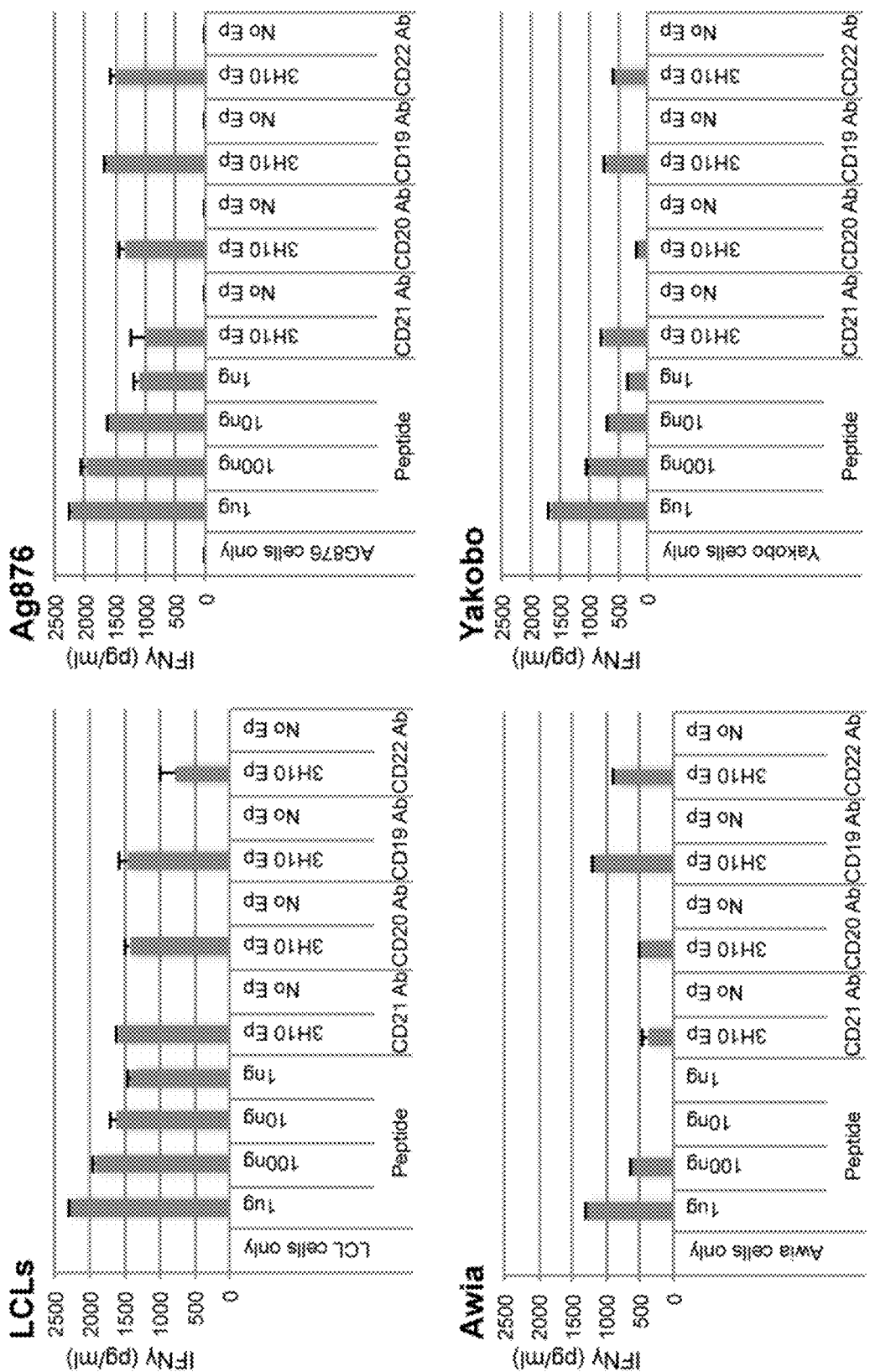

FIG. 3: Treatment of EBV-transformed B cells (LCLs) and Burkitt's Lymphoma cell lines with polypeptides according to the invention comprising EBNA3C-3H10 leads to antigen presentation and efficient T cell activation. B cells were treated for 24h with 1 ng B-cell targeted antibodies (αCD-21, -20, -19, and -22) loaded with EBNA3C epitope. Positive controls included cells pulsed with increasing amounts (1 ng-1 μg) of 3H10 peptide alone, and negative controls included either untreated cells, or cells pulsed with antibodies not containing the EBNA3C-3H10 epitope. Following treatment, B cells were mixed with EBN3C-3H10-specific T cell clones at a ratio of 1:2. After 24h, secretion of IFNγ was measured by ELISA as an indicator of T cell activation. Results are given in pg/ml.

Figure 4:
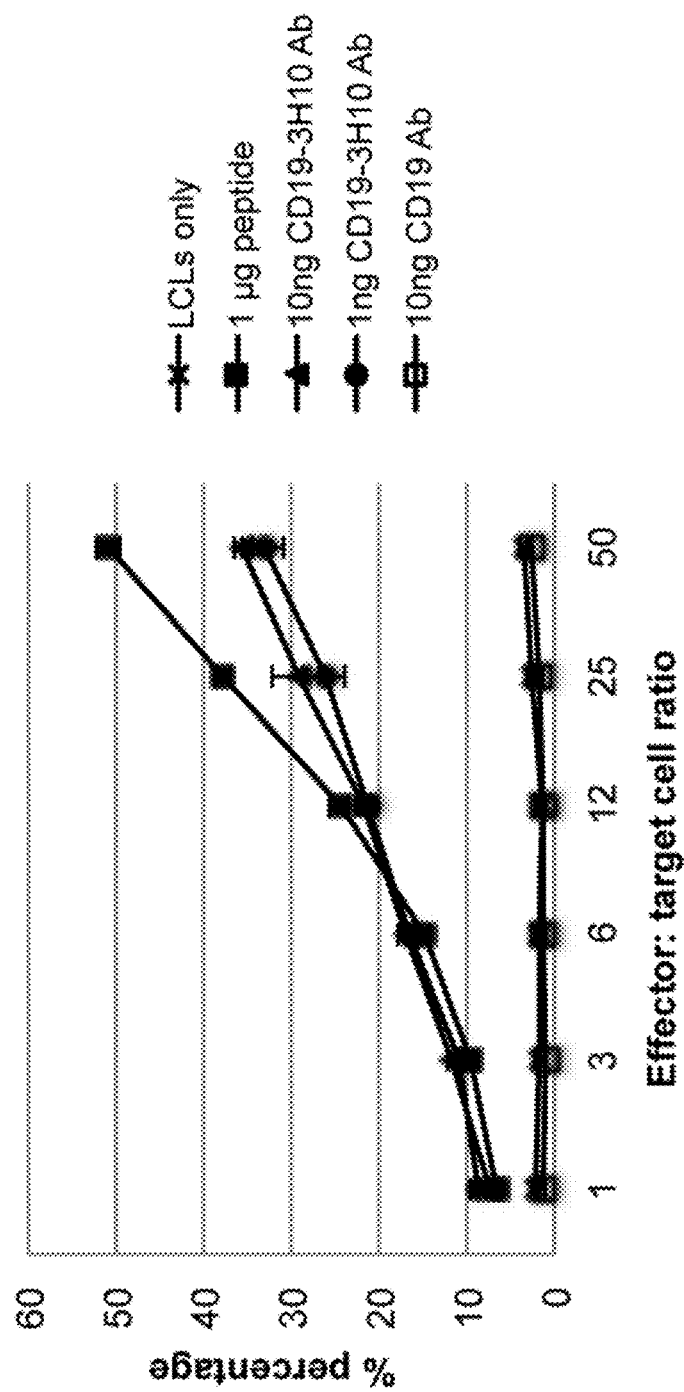

FIG. 4: Antigen presentation by polypeptides according to the invention comprising EBNA3C-3H10 results in peptide-specific cell killing by CD4+ T cells. LCLs were treated with EBNA3C-3H10-loaded αCD19 antibody (CD19-3H10 Ab; 1 ng and 10 ng), αCD19 antibody containing no epitope (CD19 Ab), or EBNA3C peptide, or were left untreated. These target cells were then labeled with $^{51}$Cr and co-incubated for 4h with EBNA3C-3H10-specific effector T cells at an increasing effector:target ratio (1:1, 3:1, 6:1, 12:1, 25:1, 50:1). A $^{51}$Cr-release assay was performed to determine the % lysis of the target LCL population as a measure of specific cell killing.

Figure 5:
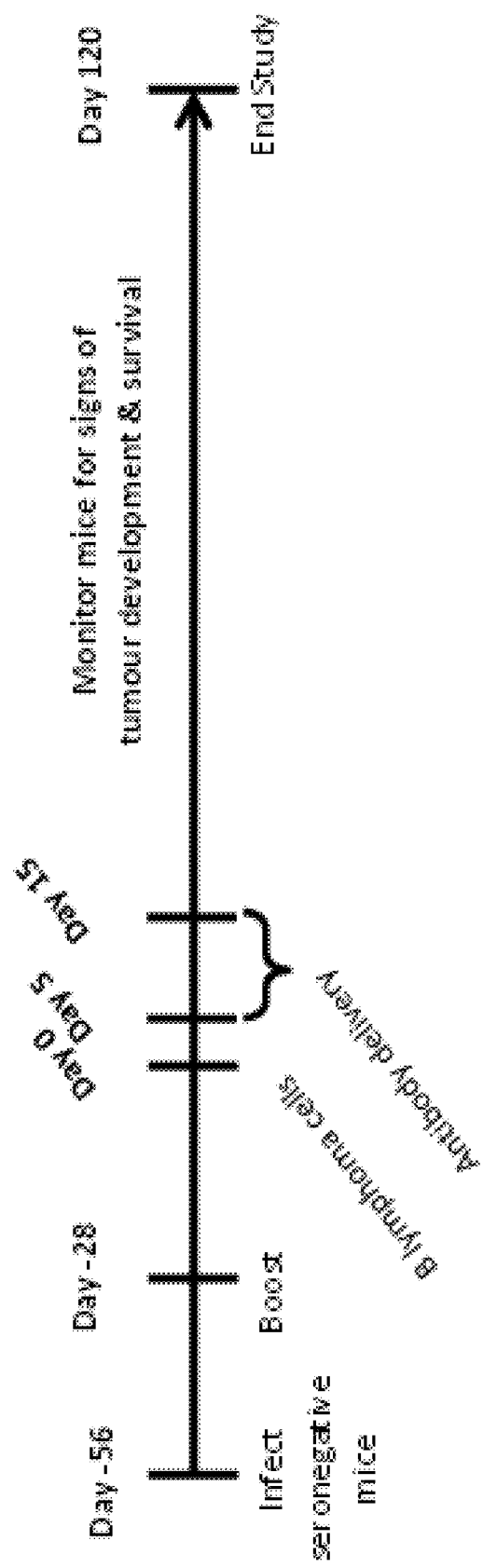

FIG. 5: General schedule of MCMV infection, lymphoma cell delivery and antibody treatment for mouse experiments of Example 5.

The following Examples shall merely illustrate the invention. They shall not be construed, whatsoever, to limit the scope of the invention.

EXAMPLE 1

Antibodies against CD21, CD19 and CD22 were fused with an antigenic epitope (5H11) from the Epstein-Barr virus latent antigen EBNA3C. The fusion proteins were used to introduce the epitope into the endosome of B cells transformed by the Epstein-Barr virus (lymphoblastoid cell lines, LCLs). The pulsed B cells were then co-cultured with a T cell clone that is specific for the EBNA3C 5H11 epitope. T cell activation was assessed by measuring interferon-γ release in the supernatant.

LCLs directly incubated with the 5H11 epitope were used as positive controls. Antibody-5H11 fusion proteins devoid of light chains were used as negative controls, as were antibodies not fused with the epitopes. 1 ng of CD21-5H11 fusion proteins which carry 20 pg of 5H11 elicited an immune response comparable to the one obtained with 1 µg of peptide (FIG. 1). Therefore, the efficiency of antigen presentation on activated B cells was 50.000 times higher after fusion with CD21 antibody than with the epitope alone. Similar results were obtained with the CD19, CD20, and CD22-specific antibodies. It is important to note that untreated EBV immortalized B cells cannot present 5H11 on the class II pathway.

EXAMPLE 2

LCLs and AG876, a Burkitt's lymphoma cell line, were used as antigen-presenting B cells and their respective abilities to present the 3H10 epitope from the EBNA3C protein fused to CD21-specific antibodies was determined by an interferon-γ release assay. 3H10 peptides alone provided a positive control, non-functional fusion proteins devoid of heavy or light chains, mock-treated antigen-presenting cells were taken as negative controls.

Both LCLs and AG876 presented 3H10 epitopes with a similar efficiency (FIG. 2). The AG876 presented 3H10 after incubation with the CD21 antibody-3H10 fusion protein less efficiently than LCLs but remained approximately 100 times more efficient than unconjugated 3H10. This relative decreased efficiency is consistent with defective antigen processing machinery in Burkitt's lymphoma cells. Nevertheless, the CD21 antibody-3H10 fusion protein elicited a potent immune response against the tumor cells.

EXAMPLE 2.1: FURTHER EVALUATING POLYPEPTIDES ACCORDING TO THE INVENTION IN EBV-TRANSFORMED B CELLS AND VARIOUS BURKITT'S LYMPHOMA CELLS LINES

A panel of antibodies loaded with various EBV epitopes has been generated. These have been evaluated for their ability to present antigen to peptide-specific T cells and to activate these T cells. In FIG. 3 is shown one example of treatment with a polypeptide according to the invention comprising an epitope from the EBNA3C protein. We were able to show that treatment with these polypeptides according to the invention results in specific T cell activation in LCLs and in several Burkitt's lymphoma cell lines.

EXAMPLE 2.2 DETERMINING THE POTENTIAL FOR T CELLS ACTIVATED BY TREATMENT WITH POLYPEPTIDES ACCORDING TO THE INVENTION TO KILL THEIR TARGET CELLS

Since polypeptides according to the invention can efficiently activate peptide-specific T cells, we wanted to determine whether these activated T cells are able to specifically kill the B cells presenting the epitopes from the immunogenic peptides. Here we performed $^{51}$Cr-release assays to demonstrate that the activated T cells can indeed kill their targets. FIG. 4 shows one example of this in LCLs.

EXAMPLE 2.3: IN VIVO STUDIES IN A MOUSE LYMPHOMA MODEL

A panel of polypeptides according to the invention in the form of "armed antibodies" containing T cell epitopes from common mouse pathogens are generated. B cell surface receptors CD-19, -20, -21 and -22, are targeted and the antibodies are coupled to the pp89 peptide, an immunodominant T cell epitope from the IE1 protein of mouse cytomegalovirus (MCMV). These antibodies are studied in the A20 model of mouse lymphoma. Injection of the A20 cell line into MCMV-positive BALB/c mice results in the development of disease that resembles human diffuse large B cell lymphoma (DLBCL).

The serostatus of the animals to MCMV is assessed by serology prior to the commencement of the study. Seronegative animals are infected with MCMV in order to ensure seroconversion and priming of T cells against the MCMV pp89 peptide. All animals are re-infected with the virus 4 weeks prior to i.v. challenge with A20 lymphoma cells (FIG. 5). At days 5 and 15 following lymphoma cell delivery, animals are treated with the recombinant AgAbs containing pp89 peptides. Mice are subsequently monitored for survival and tumour development for 120 days following lymphoma cell challenge. Mice are sacrificed when external signs of suffering are present (such as reduced mobility and altered behaviour), as per the guidelines recommended by the Society of Laboratory Animal Science (GV-SOLAS), or if no adverse symptoms appear, at 120 days following injection of cells. Refer to FIG. 5 for a schematic representation of this experimental schedule.

Molecular resonance imaging (MRI) is used in order to monitor tumour development at two time-points during the course of the study. Mill allows to both visualize the tumours and to perform volumetric analysis of the tumours. Imaging of all mice is performed when signs of tumour development are evident in the untreated group, and again prior to sacrifice. In addition, anatomical and histological examinations are performed upon sacrifice of the mice.

Using the experimental schedule outlined in FIG. 5, a panel of antibodies and treatment regimes is investigated. Firstly, antibodies against the full panel of B cell surface receptors, CD19, -20, -21 and -22 are tested, using antibody and adjuvant (Poly I:C) co-treatment. Peptide-loaded and unloaded antibodies are compared in targeting these surface receptors. Tumour growth and animal survival are monitored as markers of treatment efficacy, and are compared relative to untreated control animals and animals without lymphoma. Further experiments include: i) determination of the most effective dose of antibody treatment; and ii) an evaluation of the efficacy of treatment with armed antibodies and CD20/rituximab co-injection. Indeed, antibodies directed against CD21 or CD19 have been found to evince low cytotoxic properties that could be instead provided by anti-CD20 antibodies and therefore combine two different angles of attack against the lymphoma cells.

Once a panel of antibodies has been tested in the A20 lymphoma model, studies are extended to other lymphoma models. This includes the BCL1 model in which BCL1 cells can induce a DLBCL-like or CLL-like lymphoma, depending on the route of inoculation (i.p. or i.v, respectively), and a Burkitt's lymphoma-like model using cells from B6-myc transgenic mice.

EXAMPLE 3

Presentation of microbial antigens at the surface of B lymphocyte cells elicits recognition and destruction through T cells specific to these antigens. These T cells are present in most individuals who were previously infected by common viruses, such as herpesviruses. Individuals with a chronic Hepatitis C or HIV infection carry an increased proportion of activated B cells that can efficiently present antigens (Moir and Fauci, 2009, Nat Rev Immunol; Sugalski, Rodriguez, Moir, Anthony, 2010, J. Immunology). These infectious agents have an intrinsic ability to modify their surface antigens and subsequently they are able to evolve faster than the host's immune system can adapt. As a result, infected patients cannot clear their infections.

To overcome this problem, a library of polypeptides is generated, comprising anti-CD21 antibodies coupled to a library of Hepatitis C antigens that are found in patients with a long-standing infection, which covers the spectrum of viral antigens that appear in the course of infection and include all stages of virus evolution. This antibody library is administered to patients with a recently acquired Hepatitis C and thus primes the patient's immune system against all possible virus variants and therefore enables their elimination.

The same method is applied to patients recently infected with HIV, using a library of HIV antigens that are found in patients with a long-standing infection, which covers the spectrum of viral antigens that appear in the course of infection and include all stages of virus evolution.

EXAMPLE 4

An antibody fusion protein is created, comprising an anti-CD21 antibody fused to an immunodominant peptide from a common viral or bacterial pathogen, for example EBNA3C from EBV, and produced according to conventional methods. The antibody fusion proteins are administered to patients suffering from B-cell lymphoma, where they are taken up by Lymphoma cells. The Lymphoma cells present the T-cell epitopes comprised in the EBNA3C peptide and thus activate EBNA3C-specific T-cells, which in turn eliminate the presenting Lymphoma cells. CD4+ T cells can also act as 'cytotoxic' T cells to orchestrate the killing of target cells. There is also the possibility of cross-presentation to CD8+ T cells.

EXAMPLE 5

An antibody fusion protein is created, comprising an anti-CD22 antibody fused to myelin basic protein (MBP). The fusion protein is applied to patients at a high dose. Thus, tolerance to MBP is induced and thus progression of Multiple Sclerosis is reduced.

The invention claimed is:

1. A method for stimulating antigen-specific T-cells to kill antigen presenting cells (APC) in a subject having an immune response to a T-cell epitope, comprising:
   (a) administering to the subject a polypeptide comprising:
      (i) a binding peptide that binds to at least one protein selected from the group consisting of CD22, CD 19, CD20, and CD21; and
      (ii) an immunogenic peptide comprising the T-cell epitope;
   (b) contacting the polypeptide with an APC of the subject; and
   (c) contacting the APC with T-cells, thereby stimulating the T-cells to kill the APC;
   wherein the immunogenic peptide comprises at least one T-cell epitope from a tumor antigen, and/or at least one T-cell epitope from a protein of a virus commonly infecting the subject or against which the subject has been vaccinated.

2. The method of claim 1, wherein the binding peptide is an antibody.

3. The method of claim 1, wherein the immunogenic peptide comprises at least one T-cell epitope from a latent gene of Epstein-Barr Virus (EBV).

4. The method of claim 1, wherein the modulation of the immune response is an activation.

5. The method of claim 1, wherein the binding peptide is an antibody directed to CD21 or a peptide comprising the CD21-binding peptide of EBV gp350.

6. The method of claim 1, wherein the modulation of the immune response is a repression.

7. The method of claim 1, wherein the binding peptide is a single-chain antibody.

8. The method of claim 1, wherein at least a part of the binding peptide is contiguous in amino acid sequence with the immunogenic peptide or with an adapter binding the immunogenic peptide.

9. The method of claim 1, wherein the APC are B-cells.

10. The method of claim 1, wherein the APC are lymphoblastoid cell lines (LCL).

11. The method of claim 1, wherein the T-cell epitope is a T-cell epitope for which the probability that T-cells present in a subject recognize the T-cell epitope is high.

12. The method of claim 1, wherein the T-cell epitope is from a protein of a virus commonly infecting a subject or against which a subject has been vaccinated.

13. The method of claim 1, wherein the stimulating of step (c) further comprises generating activated T-cells from the T-cells and killing the APC by the activated T-cells.

14. A method of treating B-cell hyperproliferation in a subject suffering therefrom, comprising:
  (a) contacting the subject with a polypeptide comprising:
    (i) a binding peptide that binds to at least one protein selected from the group consisting of CD22, CD19, CD20, and CD21; and
    (ii) an immunogenic peptide comprising at least one T-cell epitope, thereby treating said B-cell hyperproliferation in said subject;
  wherein the immunogenic peptide comprises at least one T-cell epitope from a tumor antigen, and/or at least one T-cell epitope from a protein of virus commonly infecting the subject or against which the subject has been vaccinated.

15. The method of claim 14, wherein the T-cell epitope is a T-cell epitope for which the probability that T-cells present in a subject recognize the T-cell epitope is high.

16. The method of claim 14, wherein the T-cell epitope is from a protein of a virus commonly infecting a subject or against which a subject has been vaccinated.

17. The method of claim 14, wherein the B-cell hyperproliferation is an EBV-associated disease.

18. The method of claim 17, wherein the EBV-associated disease is infectious mononucleosis, post-transplant lymphoproliferative disorder (PTLD), or B-cell lymphoma.

* * * * *